US006232340B1

(12) United States Patent
Zhang et al.

(10) Patent No.: US 6,232,340 B1
(45) Date of Patent: *May 15, 2001

(54) VANADIUM COMPLEXES AND DERIVATIVES THEREOF AND METHODS RELATED THERETO

(75) Inventors: Zaihui Zhang, Richmond; Philip M. Toleikis, Vancouver; Pierre M. Lemieux, Montreal, all of (CA)

(73) Assignee: Angiotech Pharmaceuticals, Inc., Columbia (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/064,707

(22) Filed: Apr. 22, 1998

Related U.S. Application Data

(60) Provisional application No. 60/064,081, filed on Nov. 3, 1997, provisional application No. 60/044,793, filed on Feb. 24, 1997, and provisional application No. 60/060,981, filed on Oct. 3, 1997.

(51) Int. Cl.[7] ........................ A61K 31/28; A61K 31/555; C07F 5/02; C07F 9/80; C07D 305/00

(52) U.S. Cl. .......................... 514/492; 514/184; 514/185; 514/186; 514/187; 514/188; 546/2; 546/6; 546/10; 549/206; 549/210; 549/212

(58) Field of Search .............................. 556/42; 514/492, 514/184, 185, 186, 187, 188; 546/2, 6, 10; 549/206, 210, 212

(56) References Cited

U.S. PATENT DOCUMENTS

| | | | |
|---|---|---|---|
| 5,023,358 | 6/1991 | Lazaro et al. | 556/42 |
| 5,266,565 | 11/1993 | Lacoste et al. | 514/114 |
| 5,278,154 | 1/1994 | Lacoste et al. | 514/114 |
| 5,298,525 | 3/1994 | Yoon et al. | 514/460 |
| 5,300,496 | 4/1994 | McNeill et al. | 514/186 |
| 5,470,873 | 11/1995 | Yoon | 514/460 |
| 5,508,458 | 4/1996 | Zhao | 556/45 |
| 5,583,242 | 12/1996 | Schieven | 556/44 |
| 5,620,967 | 4/1997 | McNeill et al. | 514/186 |
| 5,866,563 * | 2/1999 | McNeil et al. | 514/186 |
| 5,871,779 * | 2/1999 | Cruz | 424/646 |

FOREIGN PATENT DOCUMENTS

| | | |
|---|---|---|
| WO 93/06811 | 4/1993 | (WO) . |
| WO 95/20390 | 8/1995 | (WO) . |

OTHER PUBLICATIONS

Yu. A. Bankovskii et al., "Chelates of 5–Amylthio– and 5,7–Diamylthio–8–hydroxyquinolines," *Russian Journal of Inorganic Chemistry*, 39(5), pp. 763–764, 1994.

T. Walter Duma and Robert D. Hancock, "The Affinity of the Vanadyl(IV) Ion for Nitrogen Donor Ligands," *J. Coord. Chem.*, vol. 31, pp. 135–146, 1994.

Bankovskii et al, "CA121:239365", 1994.*

Amos and Sawyer, "Nuclear Magnetic Resonance Studies of 8–Quinolinol Complexes of Molybdenum(VI, V) and of Vandium(V), as Models for Molybdenum–Flavin Interactions," *Inorganic Chemistry 13*(1): 78–83, 1974.

Bechmann et al., "EPR–Untersuchungen an Vanadylkomplexen (EPR Examination of Vanadyl Complexes)," *Z. Anorg. Allg. Chem. 544*: 215–224, 1987 (+English Translation).

Blair et al., "The Chemistry of some 8–Hydroxyquinoline Complexes of Vanadium," *J. Inorg. Nucl. Chem. 5*: 316–331, 1958.

Caravan et al., "Reaction Chemistry of BMOV, Bis(maltolato)oxovanadium(IV)–A Potent Insulin Mimetic Agent," *J. Am. Chem. Soc. 117*(51): 12759–12770, 1995.

Chauhan and Kakkar, "3–Hydroxyflavone as a Reagent for the Microdetermination of Vanadium," *Annali di Chimica 81*:179–183, 1991.

Helper and Riechel, "Identification Of the Oxidation Product of a Binuclear Mixed–valence Vanadium(IV, V) 8–Quino–linol Complex," *Inorganic Chimica Acta 54*: L255–L257, 1981.

Kohara et al., "Spectrophotometric determination of vanadium(V) by solvent extraction with 3–hydroxyflavone," *Japan Analyst 16*: 315–322, 1967. (+English Translation).

Stewart and Porte, "Electron Paramagnetic Resonance Spectra of Some Oxovandium(IV) Chelates," *J. Chem. Soc., Dalton Trans 15*: 1661–1666, 1972.

Wang et al., "Complexes of vanadium(V), molybdenum(VI) and tungsten(VI) with quercetin," *Inorganic Chem*. vol. 112: p. 899, Abstract No. 90318t, 1990. (+Wang et al., "Investigation on the Complexes of V(V), Mo(VI) and W(VI) with Quercetin," *Chinese Journal of Applied Chemistry 6*(4): 65–68, 1989.)

Weidmann et al., "K–Edge X–Ray Absorption Spectra of Biomimetic Oxovanadium Coordination Compounds," *Chemical Physics 136*: 405–412, 1989.

* cited by examiner

*Primary Examiner*—Deborah C. Lambkin
(74) *Attorney, Agent, or Firm*—Seed Intellectual Property Law Group PLLC

(57) ABSTRACT

Organovanadium complexes, and more specifically hydroxyoxovanadium(V), $\mu$-oxo dimeric oxovanadium(V) and cis-dioxovanadium(V) complexes, are provided. The complexes may be formulated into a pharmaceutical composition. The complexes and/or compositions may be used in the treatment of a variety of disease states, including use as anti-proliferative and/or anti-metastatic agents and/or to treat drug resistant tumors and/or to methods of reducing the ability of tumors to metastasize and/or for the treatment of diabetes, arthritis, multiple sclerosis, diseases involving passageways of the body, and autoimmune diseases including but not limited to psoriasis and lupus.

47 Claims, 9 Drawing Sheets

Figure 1. Effect of daily b.i.d. dosing of OHBEOV (s.c.) on weight in mice

Figure 3. H460 (human lung cancer) tumor weights in mice treated with BEOV (RED) or OHBEOV (OX) (600 μg/day (1), 800 μg/day (2), 1000 μg/day (3))

Values are mean and std. error of mean.
N=5 mice/group. One data point consists of the mean weight of two tumors grown in a mouse.
Treatment (9 days b.i.d., s.c.) was begun on day 11 following tumor inoculation.

Figure 4. Mean tumor weight versus tumor vanadium level in H460 tumor-bearing mice treated with OHBEOV (600, 800, or 1000 μg/day)

Figure 5. Plasma leukocyte count in H460 tumor-bearing mice treated with OHBEOV (600 μg, 800 μg or 1000 μg/day) b.i.d. for 9 days Figure 8. H460 (Human Lung Cancer) Tumor Volumes in SCID/RAG-2 Mice treated with 500 μg s.c. OHBEOV or $O[BEOV]_2$ b.i.d. for 9 days Values are mean +/- S.E.M.
Each point represents the average volume of 2 tumors in each animal. N=5 animals/group
(one animal died on day 8 (OHBEOV))

Dosing by s.c. administration b.i.d. for 9 days.
Values are mean and s.e.m.
N=5 (each data point consists of the average wt. of two tumors in each animal.)
H460 tumors grown in SKID/RAG-2 mice

VANADIUM COMPLEXES AND DERIVATIVES THEREOF AND METHODS RELATED THERETO

CROSS-REFERENCE TO RELATED APPLICATIONS

This application claims the priority benefit of U.S. Provisional Patent Application Nos. 60/064,081 filed Nov. 3, 1997; 60/060,981 filed Oct. 3, 1997; and 60/044,793 filed Apr. 24, 1997, where these three provisional applications are incorporated herein by reference in their entireties.

TECHNICAL FIELD

This invention relates to vanadium(V) complexes, more specifically to hydroxyoxovanadium(V), p-oxo dimeric oxovanadium(V) and cis-dioxovanadium(V) complexes, to methods for synthesizing such complexes and to the use of such complexes as therapeutic agents.

BACKGROUND OF THE INVENTION

Vanadium complexes have been reported to have therapeutic properties. See, e.g., C. E. Heylinger et al., *Science* 227:1474, 1985; Y. Shechter, *Diabetes* 39:1, 1990; C. Orvig et al., *Metal Ions in Biol. Syst.* 31:575, 1995); U.S. Pat. No. 5,527,790 by McNeill et al.; PCT published application WO 93/06811; C. Djordjevic, *Metal Ions Biol. Syst.* 31:595, 1995; T. F. Cruz et al., *Mol. Cell. Biochem.* 153:161, 1995; H. Thompson et al., *Carcinogenesis* 5:849, 1984; C. Djordjevic et al., *J. Inorg. Biochem.* 25:51, 1985; PCT published application WO 95/19177; U.S. Pat. Nos. 5,583,242 and 5,565,491; P. Caravan et al., *J. Am. Chem. Soc.* 117:12759, 1995; Y. Sun et al., *Inorg. Chem.* 35:1667, 1996; and PCT published application WO 95/20390.

However, there remains a need in the art therapeutic agents having enhanced efficacy, stability, and/or ease of synthesis, etc. The present invention is directed to meeting this need and provides additional related advantages as disclosed herein.

SUMMARY OF THE INVENTION

The present invention is directed to vanadium(V) complexes, including pharmaceutically acceptable salts thereof, of the formula:

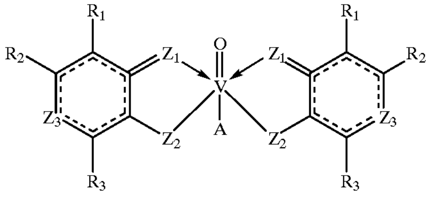

wherein, $Z_1$ is independently selected from O and $NR_4$;

$Z_2$ is independently selected from O and $NR_5$;

$Z_3$ is independently selected from O, $NR_6$ and $C(R_7)_2$;

$R_1$, $R_2$, $R_3$, $R_4$, $R_5$, $R_6$ and $R_7$ are each independently selected from H, $C_1$–$C_{10}$alkyl, substituted $C_1$–$C_{10}$alkyl, $C_7$–$C_{15}$aralkyl, substituted $C_7$–$C_{15}$aralkyl, $C_7$–$C_{15}$alkylaryl, substituted $C_7$–$C_{15}$alkylaryl, $C_6$–$C_{10}$aryl, and substituted $C_6$–$C_{10}$aryl, such that independently $R_1$ and $R_2$, and $R_1$ and $R_4$, may together form a $C_7$–$C_{15}$alkylaryl, substituted $C_7$–$C_{15}$alkylaryl, $C_6$–$C_{10}$aryl, and substituted $C_6$–$C_{10}$aryl, wherein a substituted alkyl, aralkyl, alkylaryl or aryl contains at least one substituent selected from hydroxyl, fluoro, bromo, chloro, and iodo;

A is selected from —OH, =O and

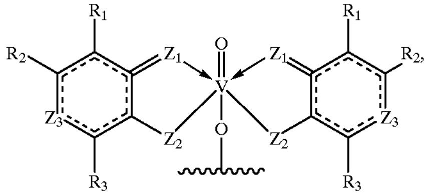

wherein $Z_1$, $Z_2$, $Z_3$, $R_1$, $R_2$, $R_3$, $R_4$, $R_5$, $R_6$ and $R_7$ are each defined as above; and a ring which includes $Z_3$ also contains two normalized bonds. The compounds of the present invention include pharmaceutically acceptable solvates or hydrates thereof. The present invention is further directed to compositions containing the above-listed vanadium complexes. An exemplary composition of the invention is a pharmaceutical composition containing one or more vanadium(V) complex as set forth above in admixture with a pharmaceutically acceptable carrier, diluent or excipient.

In another embodiment, the present invention is directed to a method of providing therapeutic treatment to an animal subject in need thereof. According to the inventive method, a therapeutically effective amount of one or more of the vanadium (V) complexs as identified above is administered to a subject in need thereof. Examples of such therapeutic treatments include treatment of proliferative disorders, bone destruction, metastases, drug resistant tumors, arthritis, psoriasis, multiple sclerosis, diseases involving a passageway of the subject's body, diabetes, diseases of the eye, diabetes-related metabolic complications, such as retinopathy, nephropathy and vasculopathy, hypertension, obesity, chronic inflammatory autoimmune disease, cardiovascular disease, lupus, bacterial infections, joint prostheses failure, periodontal disease, Inflammatory Bowel Disease (IBD), and treatment or prevention of surgical adhesions.

DETAILED DESCRIPTION OF THE INVENTION

Figure 1:
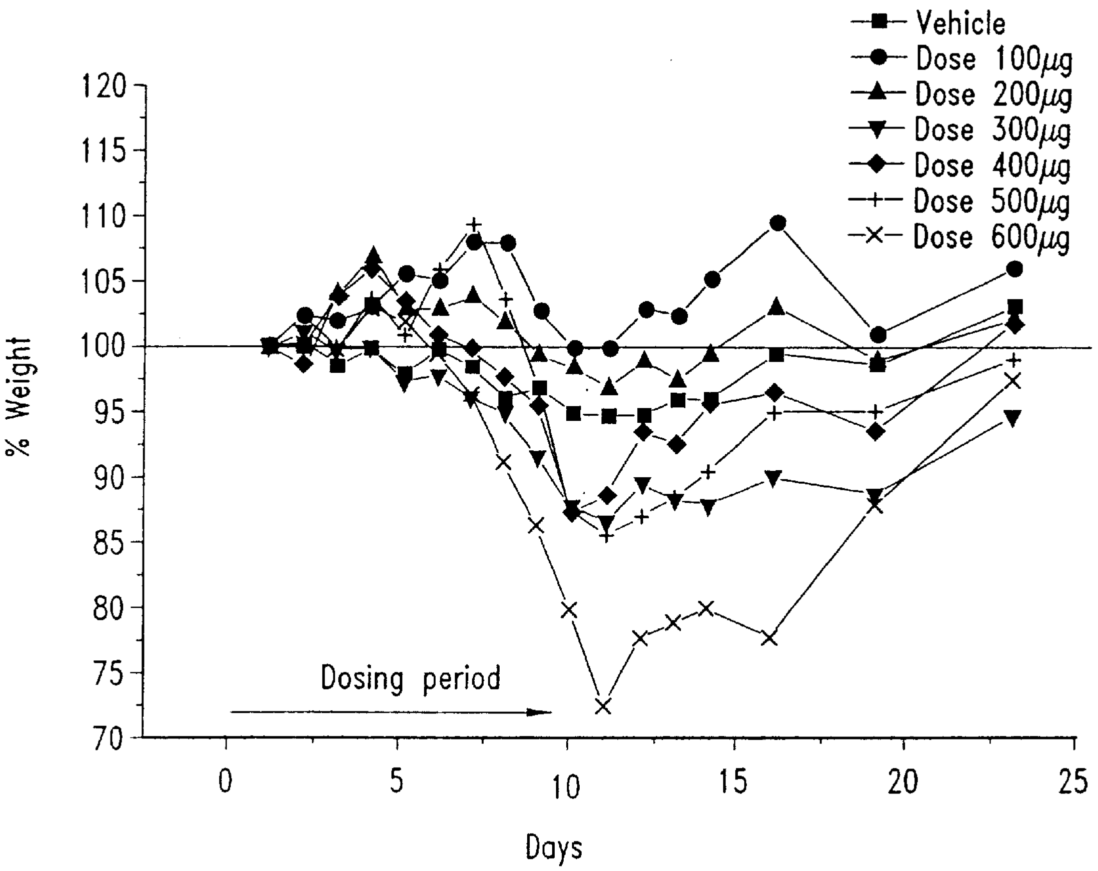
FIG. 1 is a graph showing gross toxicity of various doses (200–600 μg/dose) of OHBEOV as indicated by body weight changes in DBA-2 mice administered the complex through s.c. injection twice daily for 9 days followed by an observation period of 14 days.

The present invention is directed to vanadium(V) complexes, including pharmaceutically acceptable salts thereof, of the formula:

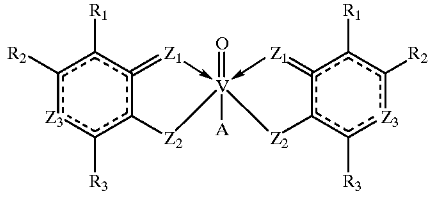

wherein, $Z_1$ is independently selected from O and $NR_4$;

$Z_2$ is independently selected from O and $NR_5$;

$Z_3$ is independently selected from O, NR and $C(R_7)_2$;

$R_1$, $R_2$, $R_3$, $R_4$, $R_5$, $R_6$ and $R_7$ are each independently selected from H, $C_1$–$C_{10}$alkyl, substituted $C_1$–$C_{10}$alkyl, $C_1$–$C_{15}$aralkyl, substituted $C_1$–$C_{15}$aralkyl, $C_7$–$C_{15}$alkylaryl, substituted $C_7$–$C_{15}$alkylaryl, $C_6$–$C_{10}$aryl, and substituted $C_6$–$C_{10}$aryl, such that independently $R_1$ and $R_2$, and $R_1$ and $R_4$, may together form a $C_7$–$C_{15}$alkylaryl, substituted $C_7$–$C_{15}$alkylaryl, $C_6$–$C_{10}$aryl, and substituted $C_6$–$C_{10}$aryl, wherein a substituted alkyl, aralkyl, alkylaryl or aryl contains at least one substituent selected from hydroxyl, fluoro, bromo, chloro, and iodo;

A is selected from —OH, ═O and

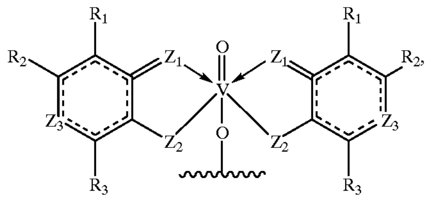

wherein $Z_1$, $Z_2$, $Z_3$, $R_1$, $R_2$, $R_3$, $R_4$, $R_5$, $R_6$ and $R_7$ are each defined as above; and a ring which includes $Z_3$ also contains two normalized bonds.

In preferred embodiments, $R_3$ is $C_2$–$C_{10}$alkyl, more preferably $C_2$–$C_5$alkyl. $R_3$ is preferably not methyl.

In a preferred embodiment, the present invention is directed to p-oxo dimeric oxovanadium(V) complexes, including pharmaceutically acceptable salts thereof, of the formula (I):

(I)

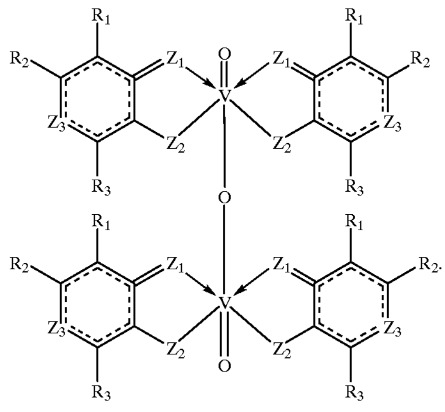

In another preferred embodiment, the invention is directed to hydroxyoxovanadium(V) complexes, including pharmaceutically acceptable salts thereof, of the formula (II):

(II)

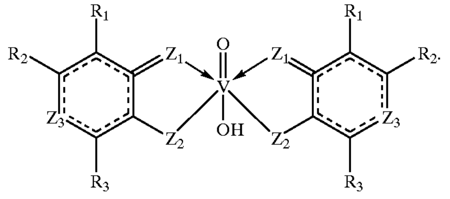

In another preferred embodiment, the present invention is directed to cis-dioxovanadium(V) complexes, and pharmaceutically acceptable salts thereof, of the formula (III):

(III)

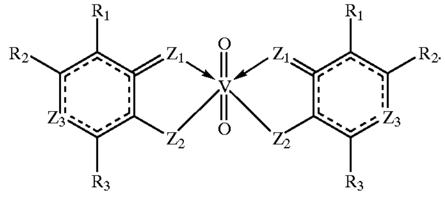

In each of formulas (I), (II) and (III), $Z_1$ is independently selected from O and $NR_4$;

$Z_2$ is independently selected from O and $NR_5$;

$Z_3$ is independently selected from O, $NR_6$ and $C(R7)_2$;

$R_1$, $R_2$, $R_3$, $R_4$, $R_5$, $R_6$ and $R_7$ are each independently selected from H, $C_1$–$C_{10}$alkyl, substituted $C_1$–$C_{10}$alkyl, $C_7$–$C_{15}$aralkyl, substituted $C_7$–$C_{15}$aralkyl, $C_7$–$C_{15}$alkylaryl, substituted $C_7$–$C_{15}$alkylaryl, $C_6$–$C_{10}$aryl, and substituted $C_6$–$C_{10}$aryl, such that independently $R_1$ and $R_2$, and $R_1$ and $R_4$, may together form a $C_7$–$C_{15}$alkylaryl, substituted $C_7$–$C_{15}$alkylaryl, $C_6$–$C_{10}$aryl, and substituted $C_6$–$C_{10}$aryl, wherein a substituted alkyl, aralkyl, alkylaryl or aryl contains at least one substituent selected from hydroxyl, fluoro, bromo, chloro, and iodo; and the rings which include $Z_3$ contain two normalized bonds.

Exemplary groups which may be chelants of the vanadium centers in a μ-oxo dimeric oxovanadium(V) complex or a hydroxyoxovanadium(V) complex or a cis-dioxovanadium(V) complex (hereinafter "vanadium (V) complex") of the invention include, without limitation, maltol (i.e., 2-methyl-3-hydroxy-4-pyrone), 3-hydroxyflavone, morin, quercetin, fisetin, and myricetin.

Preferred complexes of formulas (I), (II) and (III) have an α-hydroxypyrone chelant. An ac-hydroxypyrone chelant has the formula

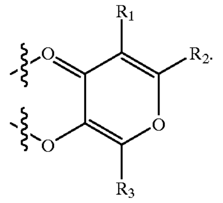

An especially preferred chelant is 2-ethyl-3-hydroxy-4-pyrone (BEOV) which, in a vanadium (V) complex of the invention of formulas (I), (II) and (III), provides a specific complex represented by the following formulas (Ia), (IIa) and (IIIa), respectively:

(Ia)

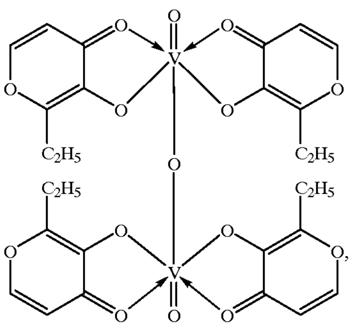

(IIa)

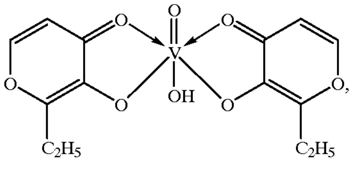

and (IIIa)

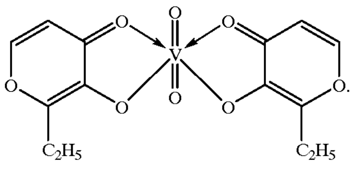

Many of the chelants in the vanadium (V) complexes of the present invention are commercially available. For example, 2-ethyl-3-hydroxy-4-pyrone is commercially available from Aldrich Chemical Co., Milwaukee, Wis., among other chemical suppliers.

Preferred vanadium (V) compounds of the invention include, without limitation: ethoxybis(2-ethyl-3-hydroxy-4-pyronato)oxovanadium(V), [VO(ETO)(EMA)$_2$]; hydroxybis(kojato)oxovanadium(V), [OHBKjOV]; μ-oxobis[bis-(kojato)oxovanadium(V)], [O(BKj)$_2$]; ethoxybis(kojato)oxovanadium(V), [VO(EtO)(Kj)$_2$]; sodium cis-bis(kojato)dioxovanadate(V), [NaBKO$_2$V]; μ-oxobis[bis(1,2-dimethyl-3-hydroxy-4-pyridinonato) oxovanadium(V)], [O(VO(Dpp)$_2$)$_2$]; μ-oxobis[bis(2-methyl-3-hydroxy-4-pyridinonato)oxovanadium(V)], [O(VO(Mpp)$_2$)$_2$]; μ-oxo[bis(1,2-dimethyl-3-hydroxy-4-pyridinonato)oxovanadium(V)], [O(VO(Dpp)$_2$)$_2$]; bis(1,2-dimethyl-3-hydroxy-4-pyridinonato) ethoxyoxovanadium (V), [VO(EtO)(Dpp)$_2$]; sodium cis-bis(1,2-dimethyl-3-hydroxy-4-pyridinonato)dioxovanadate(V), [NaVO$_2$(Dpp)$_2$]; μ-oxo[bis(2-methyl-3-hydroxy-4-pyridinonato) oxovanadium(V)], [O(VO(Mpp)$_2$)$_2$]; bis(1,2-dimethyl-3-hydroxy-4-pyridinonato)hydroxy-oxovanadium(V), [VO(OH)(Dpp)$_2$]; hydroxybis(2-methyl-3-hydroxy-4-pyridinonato)-oxovanadium(V), [VO(OH)(Mpp)$_2$]; μ-oxobis[bis(6-hydroxymethyl-3-hydroxy-1-methyl-4-pyridinonato)oxovanadium(V)], [O(VO(Hmp)$_2$)$_2$]; μ-oxobis[bis(6-hydroxymethyl-3-hydroxy-4-pyridinonato)-oxovanadium(V)], [O(VO(Hpp)$_2$)$_2$]; μ-oxo[bis(6-hydroxymethyl-3-hydroxy-1-methyl-4-pyridinonato) oxovanadium(V)], [O(VO(Hmp)$_2$)$_2$]; μ-oxo[bis(6-hydroxymethyl-3-hydroxy-4-pyridinonato)oxo-vanadium (V)], [O(VO(Hpp)$_2$)$_2$]; bis(6-hydroxymethyl-3-hydroxy-1-methyl-4-pyridinonato)hydroxyoxovanadium(V), [VO(OH)(Hmp)$_2$]; bis(6-hydroxymethyl-3-hydroxy-4-pyridinonato)-oxovanadium(V), [VO(OH)(Hpp)$_2$]; hydroxybis(8-quinolinato)oxovanadium(V), [VO(Oh)Q$_2$]; μ-oxobis[bis(8-quinolinolato)-oxovanadium(V)], [O(Voq$_2$)$_2$]; ethoxybis(8-quinolinolato)oxovanadium(V), [VO(OEt)Q$_2$]; eodium bis (8-quinolinolato)dioxovanadate(V), [NaVO$_2$Q$_2$]; hydroxybis(3-hydroxyflavonato)oxovanadium(V), [VO(OH)(Fl)$_2$]; and μ-oxobis[bis(3-hydroxyflavonato) oxovanadium(V)], [O(VO(Fl)$_2$)$_2$].

The synthesis of the μ-oxo dimeric complexes of formula (I) can be achieved by conventional metallation or trans-metallation techniques, e.g., by mixing in solution a soluble vanadium salt with the chelant or a salt or a weaker complex thereof, or by an oxidation process with an oxidant, e.g., hydrogen peroxide, from the corresponding vanadium(IV) complex.

The synthesis of the hydroxyoxovanadium(V) complexes of formula (II) can be achieved by metallation techniques under acidic conditions, e.g., by a mixture in solution of a soluble vanadium salt with the chelant or a salt, or by an oxidation process with an oxidant, e.g., hydrogen peroxide, from the corresponding vanadium(IV) complex.

The synthesis of the cis-dioxovanadium(V) complexes of formula (III) can be achieved by base treatment of the corresponding complex of formulas (I) or (II), or by oxidation with molecular oxygen of the corresponding vanadium (IV) complex. Each of these routes is shown schematically in the Scheme below, wherein the chelant is BEOV:

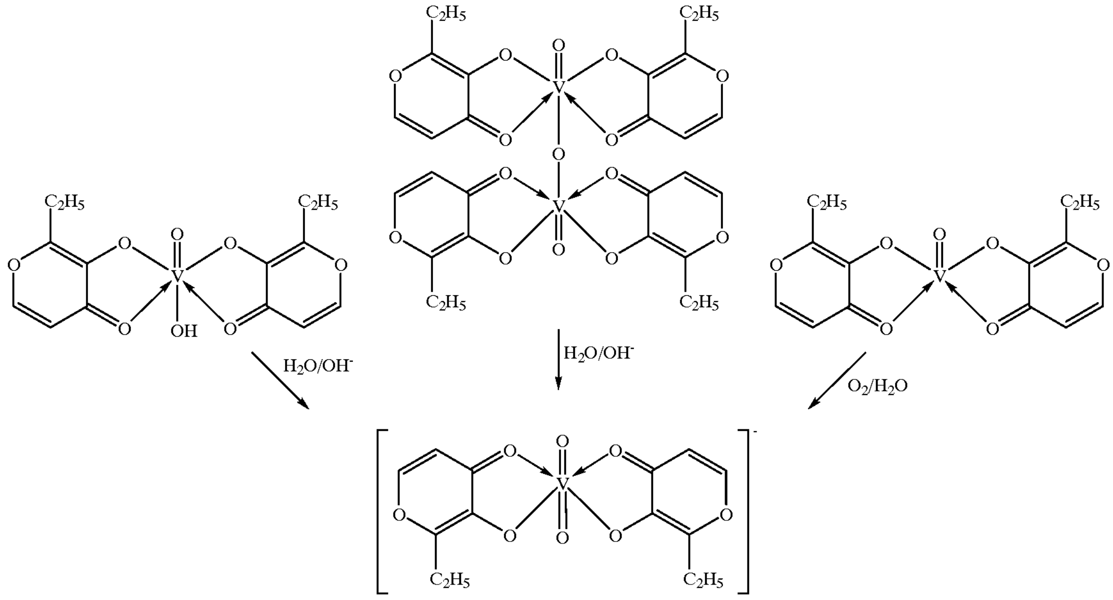

As shown in the above scheme, the cis-dioxovanadium (V) complexes of formula (III) are negatively charged, and thus are associated with a counterion. Suitable counterions are metal ions, e.g., alkaline and alkaline earth metal ions. Preferred metal ions are sodium and potassium. The counterion may be an organic cation, where a suitable organic counterion is an ammonium ion. The counterion is preferably a pharmaceutically acceptable inorganic counterion. Sodium and potassium are suitable pharmaecutically acceptable inorganic counterions.

Another aspect of the invention is a composition comprising at least one vanadium (V) complex of the present invention (including a vanadium complex of any of formulas (I), (II) or (III)) in admixture with a carrier, adjuvant or vehicle. The composition is preferably formulated as a pharmaceutical or veterinary composition comprising a pharmaceutically or veterinarily acceptable carrier, excipient or diluent, and optionally, one or more other biologically active ingredients.

In one embodiment, the present invention provides compositions which include a vanadium(V) complex of the invention in admixture or otherwise in association with one or more inert carriers, as well as optional ingredients if desired. These compositions are useful as, for example, assay standards, convenient means of making bulk shipments, or pharmaceutical compositions. An assayable amount of a complex of the invention is an amount which is readily measurable by standard assay procedures and techniques as are well known and appreciated by those skilled in the art. Assayable amounts of a complex of the invention will generally vary from about 0.001 wt % to about 75 wt % of the entire weight of the composition. Inert carriers include any material which does not degrade or otherwise covalently react with a complex of the invention. Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers.

Thus, the present invention provides a pharmaceutical or veterinary composition (hereinafter, simply referred to as a pharmaceutical composition) containing a vanadium(V) complex as described above, in admixture with a pharmaceutically acceptable carrier, diluent or excipient. The invention further provides a pharmaceutical composition containing an effective amount of a vanadium(V) complex as described above, in association with a pharmaceutically acceptable carrier, diluent or excipient.

The pharmaceutical compositions of the present invention may be in any form which allows for the composition to be administered to a patient. For example, the composition may be in the form of a solid, liquid or gas (aerosol). Typical routes of administration include, without limitation, oral, topical, parenteral, sublingual, rectal, vaginal, and intranasal. The term parenteral as used herein includes subcutaneous injections, intravenous, intramuscular, intrastemal injection or infusion techniques. Pharmaceutical composition of the invention are formulated so as to allow the active ingredients contained therein to be bioavailable upon administration of the composition to a patient. Compositions that will be administered to a patient take the form of one or more dosage units, where for example, a tablet may be a single dosage unit, and a container of vanadium(V) complex in aerosol form may hold a plurality of dosage units.

Materials used in preparing the pharmaceutical compositions should be pharmaceutically pure and non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes a vanadium(V) complex as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, emulsion or suspension. The liquid may be for oral administration or for delivery by injection, as two examples When intended for oral administration, preferred compositions contain, in addition to at least one complex of the present invention, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more adjuvants. Suitable adjuvants include sterile diluents such as water for injection, saline solution, preferably physiological saline, Ringer's solution, isotonic sodium chloride, as well as fixed oils such as synthetic mono or diglycerides which may serve as the solvent or suspending medium. Polyethylene glycols, glycerin, propylene glycol or other hydric or non-hydric solvents may also be present. In addition or alternatively, antibacterial agents such as benzyl alcohol or methyl paraben may be included. In general however, the compositions preferably do not contain hydric organic compounds, i.e., organic alcohols such as polyethyleneglycols, benzyl alcohol, etc. because organic alcohols may react with the vanadium complexes of the invention.

Antioxidants may be included as an adjuvant in a composition of the invention, however their presence is not preferred because antioxidants may discourage the formation or maintenance of the vanadium(V) state of the complexes of the invention. Antioxidants that could, but are preferably not present include ascorbic acid and sodium bisulfite. Buffers such as acetates, citrates or phosphates and agents for the adjustment of tonicity such as sodium chloride or dextrose are preferred adjuvants. While the compositions of the invention may contain chelating agents such as ethylenediaminetetraacetic acid, the inclusion of chelating agents in the compositions of the invention is not preferred because the chelating agents may react with the vanadium complexes of the invention. The parenteral preparation can be enclosed in ampoules, disposable syringes or multiple dose vials made of glass or plastic. Physiological saline is a preferred adjuvant. An injectable pharmaceutical composition is preferably sterile.

A liquid compositions intended for either parenteral or oral administration should contain an amount of an inventive complex such that a suitable dosage will be obtained. Typically, this amount is at least 0.01% of a complex of the invention in the composition. When intended for oral administration, this amount may be varied to be between 0.1 and about 70% of the weight of the composition. Preferred oral compositions contain between about 4% and about 50% of the active vanadium(V) complex. Preferred compositions and preparations according to the present invention are prepared so that a parenteral dosage unit contains between 0.01 to 1% by weight of active complex.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the inventive complex of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable non-irritating excipient. Such bases include, without limitation, lanolin, cocoa butter and polyethylene glycol.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule.

The composition in solid or liquid form may include an agent which binds to the vanadium(V) complex and thereby assists in the delivery of the active components. Suitable agents which may act in this capacity include a monoclonal or polyclonal antibody, a protein or a liposome.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of complexes of the invention may be delivered in single phase, bi-phasic, or tri-phasic systems in order to deliver the active ingredient(s). Delivery of the aerosol includes the necessary container, activators, valves, subcontainers, and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in the treatment of asthma, allergy, inflammation (including arthritis) or thrombosis.

The pharmaceutical compositions may be prepared by methodology well known in the pharmaceutical art.

A composition intended to be administered by injection can be prepared by combining the vanadium(V) complex with water so as to form a solution. A surfactant may be added to facilitate the formation of a homogeneous solution or suspension. Surfactants are compounds that non-covalently interact with a vanadium(V) complex of the invention so as to facilitate dissolution or homogeneous suspension of the vanadium(V) complex in the aqueous delivery system.

The invention also provides a method of treating an animal subject in need thereof. The animal is preferably warm-blooded. Preferred warm-blooded animals are mammals. Preferred mammals are humans. Livestock, including horses, cows, pigs and fowl are other preferred warm-blooded animal subjects. The method includes the step of administering to the subject a therapeutically effective amount of at least one of the complexes or compositions of the present invention. The treatment may be directed at any one or more of the following conditions: proliferative disorders; bone destruction; metastases; drug resistant tumors; arthritis; psoriasis; multiple sclerosis; a disease involving a passageway of the subject's body; diabetes; a disease of the eye; a diabetes-related metabolic complication selected from retinopathy, nephropathy and vasculopathy; hypertension; obesity; chronic inflammatory autoimmune disease; cardiovascular disease; and lupus.

Thus, for example, the invention provides a method of treating a proliferative disorder, wherein a patient (subject) in need thereof is administered an effective amount of a vanadium(V) complex of the invention, optionally in combination with a pharmaceutically acceptable carrier, excipient or diluent.

As an example of the novel class of vanadium complexes covered in this application, the inventors have synthesized and characterized bis(2-ethyl-3-hydroxy-4 -pyronato) hydroxyoxovanadium(V). This complex has been formulated in isotonic phosphate buffered saline at a maximum solubility of 6 mg/mL and found to be stable over a 24 hr period as measured spectrophotometrically. Thus this class of complexes exhibits improved formulation characteristics over other previously described organovanadium complexes.

Gross toxicity of complexes of the invention has been evaluated in vivo. Maximum tolerated dose studies have been conducted as measured through changes in body weight, leukocyte count, plasma glucose levels and visual inspection of organs upon autopsy using a dose schedule appropriate for tumor efficacy studies. The findings show this complex to have a relatively low toxicity profile as demonstrated by less than 15% weight loss during a treatment protocol and dose level used to demonstrate a significant degree of tumor efficacy. Furthermore, following this treatment protocol in tumor-bearing animals, no significant changes in plasma leukocyte count occurred suggesting no effect of this complex on the immune response system.

In separate experiments measuring plasma glucose levels following acute and b.i.d. dosing to measure the insulinmimetic effects of the complex, it was noted that although plasma glucose levels decreased following dosing, these levels remained within a normoglycemic range (4 mM) and returned to pre-dosing levels within 1 hr following both single and multiple b.i.d. dosing. Thus, while these complexes exhibit insulin mimetic properties, the intact glucoregulatory mechanisms in non-diabetic animals appears to prevent severe hypoglycemia even at anti-cancer chemotherapeutic doses.

The anti-proliferative potential of this complex has been evaluated in two separate solid tumor models in mice. As an initial experiment, the complex was shown to exhibit significant dose-dependent anti-tumor activity against a xenograft model of human lung cancer with a final tumor size reduction of approximately 70%. Furthermore to verify these results, the experiment was repeated using a murine solid tumor model of erythroleukemia and a xenograft model of human lung cancer at the maximum tolerated dose (500 ug/day b.i.d., s.c. for 9 days) and significant tumor efficacy was demonstrated in both models through measurement of tumor sizes on a daily basis using calipers and through tumor weights taken at the termination of the experiment. Furthermore, vanadium levels were measured in tumors following a tumor efficacy protocol and the dose of the drug strongly correlated with the tumor size and vanadium concentration confirming a dose-dependent effect of this complex in tumors.

The following examples are offered by way of illustration, not limitation.

EXAMPLES

Example 1

Synthesis of Bis(2-ethyl-3-hydroxy-4-pyronato) hydroxyoxovanadium(V), [OHBEOV]

Synthesis of bis(2-ethyl-3-hydroxy-4-pyronato) oxovanadium(IV) (BEOV): Vanadyl sulfate trihydrate (25.05 g, 11.54 mmol, Aldrich) dissolved in 25 mL of hot sterile water was slowly added to a boiling solution of 2-ethyl-3-hydroxy-4-pyrone (33.04 g, 23.58 mmol, Aldrich) dissolved in 125 mL of sterile water with stirring. Potassium hydroxide (13.44 g, 24.00 mmol, Fisher) dissolved in 20 mL of sterile water was slowly added to maintain an alkaline pH of the solution. The resulting mixture was refluxed for 1 hour and the solid obtained was collected by filtration after the mixture was cooled to about 70° C., washed twice with sterile water for irrigation and ethyl ether, and dried in vacuo for 24 hours. This procedure yielded 31.89 g of product (80% based on V). m.p. 225° C. (decomp.). This complex was characterized by the following:

Elemental analysis for $C_{14}H_{15}O_8V$: % Calculated (found): C 48.71 (49.03), H 4.09 (4.09).

Infrared spectrum ($cm^{-1}$, KBr pellet): $v_{C=O\ and\ vC=C}$: 1601, 1547, 1469, 1453; $v_{V=O}$: 993.

Mass Spectrum (+LSIMS, m/e): 346 ($VOL_2$+1), 329 ($VL_2$).

Synthesis of bis(2-ethyl-3-hydroxy-4-pyronato) hydroxyoxovanadium(V) (OHBEOV): BEOV (0.505 g, 0.0015 mole) was suspended in 5 mL of deionized water. Hydrogen peroxide (30%, 1 mL, Fisher) was slowly added to this suspension with vigorous stirring and a black solid was obtained. During this step, a lot of heat was given off and another 20 mL of deionized water was added to the mixture. The suspension was kept stirring at room temperature for one hour. The solid was collected by filtration and dried in vacuo for 16 hours. The yield was 36% based on V. This complex was characterized by the following:

Elemental analysis for $C_{14}H_{15}O_8V$: % Calculated (found): C 46.42 (46.64), H 4.17 (4.10). $^1H$ NMR spectrum (ppm, in $CD_3OD$): 1.30 (t, J=8 Hz, 6H, 2—$CH_3$), 2.90 (q, J=8 Hz, 4H, 2—$CH_2$—), 6.55 (d, J=4 Hz, 2H), 8.20 (d, J=4 Hz, 2H).

Infrared spectrum ($cm^{-1}$, KBr pellet): $v_{C=O\ and\ vC=C}$: 1611, 1572, 1553, 1478; $v_{V=O}$: 968.

Mass Spectrum (—ES, m/e): 360.9 $(M-1)^-$.

Example 2

Synthesis of bis(2-ethyl-3-hydroxy-4-pyronato) hydroxyoxovanadium(V), [OHBEOV]

A solution of sodium orthovanadate (1.05 g, 5.71 mmol) in 10 mL of deionized water was added to a warm solution (30–40° C.) of 2-ethyl-3-hydroxy-4-pyrone (1.63 g, 11.6 mmol) in 25 mL of 1M acetic acid with stirring. The black solid precipitated was collected immediately by filtration, washed twice with deionized water and dried in vacuo overnight. This procedure yielded 1.37 g of product (66%). The complex was characterized as follows:

$^1H$ NMR spectrum (ppm, in $CD_3OD$): 1.30 (t, J=8 Hz, 6H, 2—$CH_3$), 2.90(q, J=8 Hz, 4H, 2—$CH_2$—), 6.55(d, J=4 Hz, 2H), 8.20 (d, J=4 Hz, 2H).

Infrared spectrum ($cm^{-1}$, KBr pellet): $v_{C=O}$ and $v_{C=C}$: 1611, 1574, 1555, 1477; $v_{V=O}$: 968.

Example 3

Synthesis of μ-Oxobis[bis(2-ethyl-3-hydroxy-4-pyronato)oxovanadium(V)], [$O(BEOV)_2$]

A suspension of ammonium metavanadate (41.4 g, 0.35 mol) in 400 mL 0.2N NaOH is added to a hot solution (60° C.) of 2-ethyl-3-hydroxy-4-pyrone (100 g, 0.71 mol) in 2 L of 1M acetic acid with stirring. This mixture is kept stirring at 60° C. for 2 hours. The temperature is reduced to 25° C. and stirred for 2 hours. The black solid obtained is collected by filtration, washed with distilled water and dried in vacuo overnight. The yield of this reaction is 92% (114 g). This complex was characterized as follows:

Elemental analysis for $C_{28}H_{28}O_{15}V_2$: % calculated (found) C 47.61 (47.50), H 4.00 (3.98).

$^1H$ NMR spectrum (ppm, in $CD_3OD$): 1.30 (t, J=8 Hz, 6H, 2—$CH_3$), 2.90 (q, J=8 Hz, 4H, 2—$CH_2$—), 6.55 (d, J=4 Hz, 2H), 8.20 (d, J=4 Hz, 2H).

Infrared spectrum ($cm^{-1}$, KBr pellet): $v_{C=O}$ and $v_{C=C}$: 1613, 1575, 1532, 1475; $v_{V=O}$: 962.

Mass Spectrum (+LSIMS, m/e): 708 $(M+2)^+$.

Example 4

Synthesis of Ethoxybis(3-hydroxyflavonato) oxovanadium(V) [$Vo(EtO)(Fl)_2$]

3-Hydroxyflavone (1 g, 4.2 mmol) is dissolved in 30 mL 95% ethanol. Ammonium metavanadate (0.245 g, 2.1 mmol) is dissolved in 10 mL deionized water. The ammonium metavandate solution is slowly added to the soltuion of 3-hydroxyflavone with stirring. The pH is adjusted to 3 with the addition of 3N HCl and the solution is refluxed for 1 hour. The brown solid is collected by vacuum filtration and dried in vacuo overnight. The product is characterized as follows: C,H Analysis for $C_{32}H_{23}O_8V$ (Calcd/Found) C 65.54/65.43 H 3.95/3.79. Mass spectrometry (m/e, +LSIMS): 542 ($VOL_2$+1) 525 ($VL_2$) 762 ($VL_3$). IR ($cm^{-1}$, KBr pellet) $v_{V=O}$ 967.

Example 5

Synthesis of Ethoxybis(2-ethyl-3-hydroxy-4-pyronato)oxovanadium(V), [$VO(ETO)(EMA)_2$]

A suspension of $O(BEOV)_2$ (1.00 g, 1.42 mmol) in 50 mL ethanol (anhydrous) is stirred at room temperature for 72 hours. The solution is filtered to remove any remaining $O(BEOV)_2$. The filtrate is reduced in volume to approximately 10 mL and cooled at 4° C. for several hours. The solid is collected by vacuum filtration and dried in vacuo. The yield is 60%. The product is characterized as follows: C,H Analysis for $C_{16}H_{19}O_8V$ (Calcd/Found) C 49.24/48.93 H 4.91/4.88. Mass spectrometry (m/e, +LSIMS): 346 ($VOL_2$+1) 329 ($VL_2$). IR ($cm^{-1}$, KBr pellet) $v_{C=O}$ and $v_{C=C}$: 1611, 1574, 1512, 1478 $v_{V=O}$ 967.

Example 6

Synthesis of Hydroxybis(kojato)oxovanadium(V), [OHBKOV]

Synthesis of bis(kojato)oxovanadium(IV) (BKOV): Vanadyl sulfate trihydrate (1 mole) dissolved in hot sterile water is slowly added to a boiling solution of kojic acid (2 moles) dissolved in sterile water. Potassium hydroxide (2 moles) dissolved in sterile water is slowly added to maintain the pH of the solution in alkaline. The resulting mixture is refluxed for 1 hour and the solid obtained is collected by filtration after the mixture is cooled, washed with sterile water and ethyl ether, and dried in vacuo for 24 hours.

Synthesis of hydroxybis(kojato)oxovanadium(V) (OHBKOV): BKOV (1 mole) obtained from the above step is suspended in deionized water. Hydrogen peroxide (30%, 4–6 moles) is slowly added to this suspension with vigorous stirring and a solid is obtained. The suspension is kept stirring at room temperature for one hour.

The solid is collected by filtration and dried in vacuo overnight.

Example 7

Synthesis of Hydroxybis(kojato)oxovanadium(V), [OHBKOV]

A solution of sodium orthovanadate (1 mole) in deionized water is added to a solution of kojic acid (2 moles) in 0.005M HCl with stirring and the pH of the solution is maintained between 2–3 at all times by the addition of HCl. The solid precipitated is collected immediately by filtration, washed with deionized water and dried in vacuo overnight.

Example 8

Synthesis of μ-oxobis[bis(kojato)oxovanadium(V)], [$O(BKOV)_2$]

A suspension of ammonium metavanadate (1 mole) in deionized water is added to a hot solution (60–70° C.) of kojic acid (2 moles) in 1M acetic acid with stirring. This mixture is kept stirring at 70° C. for 3 hours. The solid obtained is collected by filtration, washed with hot water and dried in vacuo overnight.

Example 9

Synthesis of Ethoxybis(kojato)oxovanadium(V), [$VO(ETO)(KJ)_2$]

A suspension of $O(BKOV)_2$ in absolute ethanol is heated to 50–60° C. with stirring for about 1 hour. The volume of the solvent is reduced under reduced pressure and the residue is cooled in a −20° C. freezer overnight. The dark red solid precipitated upon cooling is collected by filtration, washed with cooled ethanol and water, and dried in vacuo overnight.

Example 10

Synthesis of Sodium Cis-bis(kojato)dioxovanadate (V), [$NABKO_2V$]

One equivalent of sodium orthovanadate dissolved in distilled water is slowly added to a solution of 2 equivalents of kojic acid dissolved in phosphate buffer (pH 7.4). A yellow solution is immediately obtained and it is kept stirring in air for an hour. The yellow solid crystallized upon cooling is collected by filtration, and dried in vacuum overnight.

Example 11

Synthesis of μ-oxobis[bis(1,2-dimethyl-3-hydroxy-4-pyridinonato)oxovanadium(V)], $[O(VO(DPP)_2)_2]$ Synthesis of 1,2-dimethyl-3-hydroxy-4-pyridinone (Hdpp): A solution of 40% methylamine in water is added to a solution of maltol dissolved in hot distilled water. The pH of this solution is adjusted to 9.8 by the addition of HCl solution. The mixture is kept under reflux overnight and then decolorized with activated charcoal. The solvent is removed under reduced pressure. The white product is obtained upon recrystallization from hot water.

Synthesis of μ-oxobis[bis(1,2-dimethyl-3-hydroxy-4-pyridinonato)-oxovanadium(V)]: Ammonium metavanadate (1 mole) dissolved in hot distilled water is added to a hot solution of 1,2-dimethyl-3-hydroxy-4-pyridinone (2 moles) dissolved in 1M acetic acid with stirring. This mixture is kept stirring at 70° C. for 3 hours. The solid obtained is collected by filtration, washed with hot water and dried in vacuo overnight.

Example 12

Synthesis of μ-Oxobis[bis(2-methyl-3-hydroxy-4-pyridinonato)oxovanadium(V)], $[O(VO(MPP)_2)_2]$ Synthesis of 2-methyl-3-hydroxy-4-pyridinone (Hmpp): An ammonia solution is added to a solution of maltol dissolved in hot distilled water. The pH of this solution is adjusted to 9.8 by the addition of HCl solution. The mixture is kept under reflux overnight and then decolorized with activated charcoal. The solvent is removed under reduced pressure. The white product is obtained upon recrystallization from hot water.

Synthesis of μ-oxobis[bis(2-methyl-3-hydroxy-4-pyridinonato)oxo-vanadium(V)]: Ammonium metavanadate (1 mole) dissolved in hot distilled water is added to a hot solution of 2-methyl-3-hydroxy-4-pyridinone (2 moles) dissolved in 1M acetic acid with stirring. This mixture is kept stirring at 70° C. for 3 hours. The solid obtained is collected by filtration, washed with hot water and dried in vacuo overnight.

Example 13

Synthesis of μ-Oxo[bis(1,2-dimethyl-3-hydroxy-4-pyridinonato)oxovanadium(V)], $[O(VO(DPP)_2)_2]$ An aqueous solution of methylamine (40%) is added to a mixture of sodium orthovanadate (1 mole) and maltol (2 moles) dissolved in hot distilled water with stirring. The pH of this solution is adjusted to about 9.8 with HCl solution. This mixture is kept under reflux and stirring overnight. The pH of this solution is adjusted again to 4–5 with HCl and the mixture is kept stirring at 70° C. for another 3 hours. The solid obtained is collected by filtration, washed with hot water and dried in vacuo overnight.

Example 14

Synthesis of Bis(1,2-dimethyl-3-hydroxy-4-pyridinonato) ethoxyoxovanadium(V), $[VO(ETO)(DPP)_2]$ A suspension of $O(VO(Dpp)_2)_2$ in absolute ethanol is heated to 50–60° C. with stirring for about 1 hour. The volume of the solvent is reduced under reduced pressure and the residue is cooled in a −20° C. freezer overnight. The dark red solid precipitated upon cooling is collected by filtration, washed with cooled ethanol and water, and dried in vacuo overnight.

Example 15

Synthesis of Sodium Cis-bis(1,2-dimethyl-3-hydroxy-4-pyridinonato)dioxovanadate(V), $[NaVO_2(DPP)_2]$ One equivalent of sodium orthovanadate dissolved in distilled water is slowly added to a solution of 2 equivalent of 1,2-dimethyl-3-hydroxy-4-pyridinone dissolved in phosphate buffer (pH 7.4). A yellow solution is immediately obtained and it is kept stirring in air for an hour. The yellow solid crystallized upon cooling is collected by filtration, and dried in vacuo overnight.

Example 16

Synthesis of μ-Oxo[bis(2-methyl-3-hydroxy-4-pyridinonato)oxovanadium(V)], $[O(VO(MPP)_2)_2]$ An aqueous solution of ammonia is added to a mixture of sodium orthovanadate (1 mole) and maltol (2 moles) dissolved in hot distilled water with stirring. The pH of this solution is adjusted to about 9.8 with HCl solution. This mixture is kept under reflux and stirring overnight. The pH of this solution is adjusted again to 4–5 with HCl and the mixture is kept stirring at 70° C. for another 3 hours. The solid obtained is collected by filtration, washed with hot water and dried in vacuo overnight.

Example 17

Synthesis of Bis(1,2-dimethyl-3-hydroxy-4-pyridinonato)hydroxy-oxovanadium(V), $[VO(OH)(DPP)_2]$ Synthesis of 1,2-dimetyl-3-hydroxy-4-pyridinone (Hdpp): A solution of 40% methylamine in water is added to a solution of maltol dissolved in hot distilled water. The pH of this solution is adjusted to 9.8 by the addition of HCl solution. The mixture is kept under reflux overnight and then decolorized with activated charcoal. The solvent is removed under reduced pressure. The white product is obtained upon recrystallization from hot water.

Synthesis of bis(1,2-dimethyl-3-hydroxy-4-pyridinonato) hydroxy-oxovanadium(V): Sodium orthovanadate (1 mole) dissolved in distilled water is added to a solution of 1,2-dimethyl-3-hydroxy-4-pyridinone (2 moles) dissolved in 0.005M HCl with stirring and the pH of the solution is maintained between 2–3 at all times by the addition of HCl. The solid precipitate is collected immediately washed with hot water and dried in vacuo overnight.

Example 18

Synthesis of Hydroxybis(2-methyl-3-hydroxy-4-pyridinonato)oxovanadium(V), $[VO(OH)(MPP)_2]$ Synthesis of 2-methyl-3-hydroxy-4-pyridinone (Hmpp): An ammonia solution is added to a solution of maltol dissolved in hot distilled water. The pH of this solution is adjusted to 9.8 by the addition of HCl solution. The mixture is kept under reflux overnight and then decolorized with activated charcoal. The solvent is removed under reduced pressure. The white product is obtained upon recrystallization from hot water.

Synthesis of hydroxybis(2-methyl-3-hydroxy-4-pyridinonato)oxovanadium(V): Sodium orthovanadate (1 mole) dissolved in hot distilled water is added to a hot solution of 2-methyl-3-hydroxy-4-pyridinone (2 moles) dissolved in 0.005M HCl with stirring and the pH of the solution is maintained between 2–3 at all times by the addition of HCl. The solid obtained is collected by filtration immediately, washed with hot water and dried in vacuo overnight.

Example 19

Synthesis of $\mu$-Oxobis[bis(6-hydroxymethyl-3-hydroxy-1-methyl-4-pyridinonato)oxovanadium(V)], $[O(VO(HMP)_2)_2]$ Synthesis of 6-hydroxymethyl-3-hydroxy-1-methyl-4-pyridinone (Hhmp): A solution of 40% methylamine in water is added to a solution of kojic acid dissolved in hot distilled water. The pH of this solution is adjusted to 9.8 by the addition of HCl solution. The mixture is kept under reflux overnight and then decolorized with activated charcoal. The solvent is removed under reduced pressure. The white product is obtained upon recrystallization from hot water.

Synthesis of $\mu$-oxobis[bis(6-hydroxymethyl-3-hydroxy-1-methyl-4-pyridinonato)oxovanadium(V)]: Ammonium metavanadate (1 mole) dissolved in hot distilled water is added to a hot solution of 6-hydroxymethyl-3-hydroxy-1-methyl-4-pyridinone (2 moles) dissolved in 1M acetic acid with stirring. This mixture is kept stirring at 70° C. for 3 hours. The solid obtained is collected by filtration, washed with hot water and dried in vacuo overnight.

Example 20

Synthesis of $\mu$-Oxobis[bis(6-hydroxymethyl-3-hydroxy-4-pyridinonato)-oxovanadium(V)], $[O(VO(HPP)_2)_2]$ Synthesis of 6-hydroxymethyl-3-hydroxy-4-pyridinone (Hhpp): An ammonia solution is added to a solution of maltol dissolved in hot distilled water. The pH of this solution is adjusted to 9.8 by the addition of HCl solution. The mixture is kept under reflux overnight and then decolorized with activated charcoal. The solvent is removed under reduced pressure. The white product is obtained upon recrystallization from hot water.

Synthesis of $\mu$-oxobis[bis(6-hydroxymethyl-3-hydroxy-4-pyridinonato)-oxovanadium(V)]: Ammonium metavanadate (1 mole) dissolved in hot distilled water is added to a hot solution of 6-hydroxymethyl-3-hydroxy-4-pyridinone (2 moles) dissolved in 1M acetic acid with stirring. This mixture is kept stirring at 70° C. for 3 hours. The solid obtained is collected by filtration, washed with hot water and dried in vacuo overnight.

Example 21

Synthesis of $\mu$-Oxo[bis(6-hydroxymethyl-3-hydroxy-1-methyl-4-pyridinonato)oxovanadium(V)], $[O(VO(HMP)_2)_2]$ An aqueous solution of methylamine (40%) is added to a mixture of sodium orthovanadate (1 mole) and kojic acid (2 moles) dissolved in hot distilled water with stirring. The pH of this solution is adjusted to about 9.8 with HCl solution. This mixture is kept under reflux and stirring overnight. The pH of this solution is then adjusted to 4–5 with HCl and the mixture is kept stirring at 70° C. for 3 hours. The solid obtained is collected by filtration, washed with hot water and dried in vacuo overnight.

Example 22

Synthesis of 1-Oxo[bis(6-hydroxymethyl-3-hydroxy-4-pyridinonato) oxovanadium(V)], $[O(VO(HPP)_2)_2]$ An aqueous solution of ammonia is added to a mixture of ammonium metavanadate (1 mole) and kojic acid (2 moles) dissolved in hot distilled water with stirring. The pH of this solution is adjusted to about 9.8 with HCl solution. This mixture is kept under reflux and stirring overnight. The pH of this solution is adjusted again to 4–5 with HCl and the mixture is kept stirring at 70° C. for another 3 hours. The solid obtained is collected by filtration, washed with hot water and dried in vacuo overnight.

Example 23

Synthesis of bis(6-hydroxymethyl-3-hydroxy-1-methyl-4-pyridinonato)hydroxyoxovanadium(V), $[VO(OH)(HMP)_2]$ Synthesis of 6-hydroxymethyl-3-hydroxy-1-methyl-4-pyridinone (Hhmp): A solution of 40% methylamine in water is added to a solution of kojic acid dissolved in hot distilled water. The pH of this solution is adjusted to 9.8 by the addition of HCl solution. The mixture is kept under reflux overnight and then decolorized with activated charcoal. The solvent is removed under reduced pressure. The white product is obtained upon recrystallization from hot water.

Synthesis of bis(6-hydroxymethyl-3-hydroxy-1-methyl-4-pyridinonato)-hydroxyoxovanadium(V): Sodium orthovanadate (1 mole) dissolved in distilled water is added to a solution of 6-hydroxymethyl-3-hydroxy-1-methyl-4-pyridinone (2 moles) dissolved in 0.005M HCl with stirring and the pH of the solution is maintained between 2–3 at all times by the addition of HCl. The solid precipitated is collected immediately, washed with hot water and dried in vacuo overnight.

Example 24

Synthesis of Bis(6-hydroxymethyl-3-hydroxy-4-pyridinonato)-oxovanadium(V), $[VO(OH)(HPP)_2]$ Synthesis of 6-hydroxymethyl-3-hydroxy-4-pyridinone (Hhpp): An ammonia solution is added to a solution of maltol dissolved in hot distilled water. The pH of this solution is adjusted to 9.8 by the addition of HCl solution. The mixture is kept under reflux overnight and then decolorized with activated charcoal. The solvent is removed under reduced pressure. The white product is obtained upon recrystallization from hot water.

Synthesis of bis(6-hydroxymethyl-3-hydroxy-4-pyridinonatohydroxy-oxovanadium(V) Sodium orthovanadate (1 mole) dissolved in distilled water is added to a solution of 6-hydroxymethyl-3-hydroxy-4-pyridinone (2 moles) dissolved in 0.005M HCl with stirring and the pH of the solution is maintained between 2–3 at all times by the addition of HCl. The solid obtained is collected by filtration immediately, washed with hot water and dried in vacuo overnight.

Example 25

Synthesis of Hydroxybis(8-quinolinolato) oxovanadium(V), $[VO(OH)Q_2]$

According to a literature procedure (see, e.g., *Inorg. Chem.* 1974, 13, 78–83), ammonium metavanadate (1 mole)

dissolved in a weak NaOH solution is added slowly to a solution of 8-quinolinol (2 moles) in 1M acetic acid with stirring. A black precipitate is formed and this mixture is digested on a hot plate at low heat for 5 hours. The black solid is collected by filtration and dried at 120° C.

Example 26

Synthesis of μ-Oxobis[bis(8-quinolinolato) oxovanadium(V)], $[O(VOQ_2)_2]$

According to a literature procedure (see, e.g., *Inorg. Chem.* 1982, 21, 3310–3316), a suspension of bis(pentane-2,4-dionato)oxovanadium(IV) (1 mole) in acetone is gently heated with 8-quinolinol (2 moles) in air. The suspension is allowed to stir for 8 hours in an oxygen atmosphere; then the black solid is collected by filtration, washed with acetone and then dried in vacuo.

Example 27

Synthesis of Ethoxybis(8-quinolinolato) oxovanadium(V), $[VO(OET)Q_2]$

According to a literature procedure, (see, e.g., *Inorg. Chem.* 1982, 21, 3310–3316), $[O(VOQ_2)_2]$ is suspended in anhydrous ethanol and refluxed for 2 hours. The filtrate is separated from the suspension by vacuum filtration. The volume of the filtrate is reduced under vacuum and the remaining solution is evaporated resulting in the desired product.

Example 28

Synthesis of Potassium Cis-bis(2-ethyl-3-hydroxy-4-pyronato)dioxovanadate(V)

μ-Oxobis(2-ethyl-3-hydroxy-4-pyronato)oxovanadium (V) (5.10 g, 7.22 mmol) was suspended in 10 mL of deionized water. A solution of KOH (2N, 10 mL) was slowly added to this suspension with stirring and a clear yellow solution was obtained. The resulting solution was kept stirring at room temperature for 1 hour. The solvent was removed under reduced pressure and a greenish yellow solid obtained was dried in vacuo overnight. This procedure yielded 5.88 g of product (96%). The product was characterized as follows: m.p.: 160° C. (decomposes). C, H analysis for $C_{14}H_{14}O_8VK.1.25H_2O$ (calcd./found): $C_{39.79/39.74}$, H 3.93/3.64. Mass spectrum (m/e, +LISMS): 401 ($KVO_2L_2$+1), 384 ($KVOL_2$), 346 ($VOL_2$+1). Infrared spectrum ($cm^{-1}$, KBr pellet): $v_{C=O}$ and $v_{C=C}$: 1590, 1523, 1467; $v_{V=O}$: 901 and 890. $^1H$ NMR spectrum (ppm, in $D_2O$): 1.19 (6 H, t, J=7.5 Hz), 2.74 (4 H, q, J=7.5 Hz), 6.46 (2 H, d, J=6.0 Hz), 8.00 (2 H, d, J=6.0 Hz).

Example 29

Synthesis of Sodium Bis(8-quinolinolato) dioxovanadate(V), $[NAVO_2Q_2]$

According to literature procedure, (see, e.g., *Inorg. Chem.* 1982, 21, 3310–3316), a suspension of $O(VOQ_2)_2$ (prepared in Example 26) in a $DMF/H_2O$ solution of NaOH is gently heated with stirring for 1 hour. The color of the suspension changes from deep black to yellow. The suspension is filtered while warm, and the resulting solution is kept at 0° C. overnight. The solid obtained upon cooling is collected by filtration and dried in vacuo.

Example 30

Synthesis of Hydroxybis(3-hydroxyflavonato) oxovanadium(V), $[VO(OH)(FL)_2]$

Ammonium metavanadate (1 mole) dissolved in 1M acetic acid is slowly added to a solution of 3-hydroxyflavone (2 moles) dissolved in chloroform. The mixture is kept under reflux for about 1 hour. The organic layer is collected, dried over anhydrous $MgSO_4$. The solvent is removed under reduced pressure and the solid obtained is washed with water and chloroform, and then dried in vacuo overnight.

Example 31

Synthesis of μ-Oxobis[bis(3-hydroxyflavonato) oxovanadium(V)], $[O(VO(FL)_2)_2]$ A suspension of bis(pentane-2,4-dionato)oxovanadium (IV) ($VO(acac)_2$) (0.5 g, 2 mmol) in 20 mL acetone is gently heated with stirring. 3-hydroxyflavone (0.9 g, 4 mmol) is added to the suspension and stirred for 24 hours under a condensor apparatus to prevent solvent evaporation. The black solid is filtered by vacuum filtration and dried in vacuo overnight. The yield was 83.8%. The product is characterized as follows: C,H Analysis for $C_{60}H_{36}O_{15}V_2$ (Calcd/Found) $C_{65.68/65.24}$ H 3.30/3.30. IR ($cm^{-1}$, KBr pellet) $v_{V=O}$ 970.

Example 32

Synthesis of Ammonium Cis-bis(2-ethyl-3-hydroxy-4-pyronato)dioxovanadate(V)

To a suspension of ammonium metavanadate (5.52 g, 47.2 mmol) in 15 mL of deionized water was slowly added 2-ethyl-3-hydroxy-4(H)-pyran-4-one (13.42 g, 95.8 mmol). This mixture was kept stirring at room temperature for 4.5 hours. The resulting greenish yellow solid was isolated by filtration and dried in vacuo overnight. The yield was 67% based on V (11.97 g). The product was characterized as follows. m.p.: 120° C. (decomposes). C, H and N analysis for $C_{14}H_{18}NO_8V$ (Calcd/found): C 44.34/44.67, H 4.78/4.79, N 3.69/3.75. Mass Spectrometry (m/e, +LISMS): 397 ($NH_4VO_2L_2$+$NH_4$), 379 ($NH_4VO_2L_2$), 346 ($VOL_2$+1). IR ($cm^{-1}$, KBr pellet): $v_{C=O\ and\ C=C}$: 1589, 1525, 1466, 1454; $v_{V=O}$: 922 and 863. $^1H$ NMR Spectrum (ppm, $D_2O$): 1.19 (6 H, t, J=7.5 Hz), 2.74 (4 H, q, J=7.5 Hz), 6.46 (2 H, d, J=6.0 Hz), 8.00 (2 H, d, J=6.0 Hz).

Example 33

Maximum Tolerated Dose Study of OHBEOV Administered S.C.

A Maximum Tolerated Dose (M.T.D.) study was undertaken to determine a safe tolerable dose for administration of OHBEOV through a parenteral (s.c.) route of administration delivered twice daily (b.i.d.) for nine days in female mice (DBA-2). The protocol was as follows. 14 DBA-2 mice were randomly divided into groups of 2 for a total of 7 groups. Groups were treated as follows. Vehicle (sterile isotonic phosphate buffer, pH 7.2) was filtered through 0.22 pm sterile filter (Costar 140666). OHBEOV was dissolved with gentle heating and stirring for about 20 min. To a concentration of 2 mg/mL in vehicle and filtered through 0.22 pm sterile filter (Costar 140666).

Groups were as follows:

1) Vehicle control: 300 μl/dose for a total of 600 μl/day.
2) 50 μl of 2 mg/mL OHBEOV mixed with 250 μl vehicle to make 300 μl to be injected for a total of 200 μg/day.
3) 100 μl of 2 mg/mL OHBEOV mixed with 200 μl vehicle to make 300 μl to be injected for a total of 400 μg/day,
4) 150 μl of 2 mg/mL OHBEOV mixed with 150 μl vehicle to make 300 μl to be injected for a total of 600 μg/day.

5) 200 $\mu$l of 2 mg/mL OHBEOV mixed with 100 $\mu$l vehicle to make 300 $\mu$l to be injected for a total of 800 $\mu$g/day.

6) 250 $\mu$l of 2 mg/mL OHBEOV mixed with 50 $\mu$l vehicle to make 300 $\mu$l to be injected for a total of 1000 $\mu$g/day.

7) 300 $\mu$l of 2 mg/mL OHBEOV to be injected for a total of 1200 $\mu$g/day.

Mice were weighed as a group (N=2) prior to injection in the morning. Injections were s.c. in the neck region and were delivered twice daily between 8–9 a.m. and between 4–5 p.m. Treatment continued for a total of nine days. Groups were observed and weighed daily for 2 weeks following the final treatment and observed for behavioral signs of toxicity i.e. reduced preening, and mobility and organ failure, i.e., weight loss, death. Following this period, mice were terminated with carbon dioxide. Liver, spleen and kidney (and other organs) were weighed and kept for histology if appearance appeared abnormal.

Results:

Doses up to and including 500 $\mu$g (1000 $\mu$g/day) were well tolerated as shown by a less than 15% weight loss through the 9 day treatment and 14 day follow up period (FIG. 1). In fact, following termination of treatment, all animals regained their original weight. At the maximum dose of 600 $\mu$g one animal was terminated due to weight loss (25%). Upon necropsy, the only organ appearing to show alteration by visual inspection was the spleen which was enlarged. Spleen enlargement has also been noted following treatment with other vanadium complexes. In addition, some skin lesions were noted at the injection site at the higher doses.

Example 34

Maximum Tolerated Dose Study (I.V.) of OHBEOV

A Maximum Tolerated Dose (M.T.D.) study was undertaken to determine a safe tolerable dose for administration of OHBEOV through an intravenous route of administration delivered twice daily for nine days in female mice (DBA-2). The protocol was as follows. 8 DBA-2 female mice were randomly divided into groups of 2 for a total of 4 groups. Groups were treated as follows. Vehicle (sterile isotonic phosphate buffer, pH 7.2) was filtered through 0.22 $\mu$m sterile filter (Costar 140666). OHBEOV was dissolved with gentle heating and stirring to a concentration of 2 mg/mL in vehicle and filtered through 0.22 pm sterile filter (Costar 140666).

Groups were as follows:

1) Vehicle control: 300 $\mu$l/dose for a total of 600 $\mu$l/day.

2) 50 $\mu$l of 2 mg/mL OHBEOV mixed with 250 $\mu$l vehicle to make 300 $\mu$l to be injected for a total of 200 $\mu$g/day.

3) 100 $\mu$l of 2 mg/mL OHBEOV mixed with 200 $\mu$l vehicle to make 300 $\mu$l to be injected for a total of 400 $\mu$g/day.

4) 150 $\mu$l of 2 mg/mL OHBEOV mixed with 150 $\mu$l vehicle to make 300 $\mu$l to be injected for a total of 600 $\mu$g/day.

5) 200 $\mu$l of 2 mg/mL OHBEOV mixed with 100 $\mu$l vehicle to make 300 $\mu$l to be injected for a total of 800 $\mu$g/day.

Mice were weighed as a group (N=2) prior to injection in the morning. Injections were i.v. in the tail vein and were delivered b.i.d. between 8–9 a.m. and between 4–5 p.m. Treatment continued for a total of nine days. Groups were observed and weighed daily for 2 weeks following the final treatment and observed for behavioral signs of toxicity, i.e., reduced preening, and mobility and organ failure, i.e., weight loss, death. Following this period, mice were terminated with carbon dioxide. Liver, spleen and kidney (and other organs) weighed and kept for histology if appearance appeared abnormal.

Figure 2:
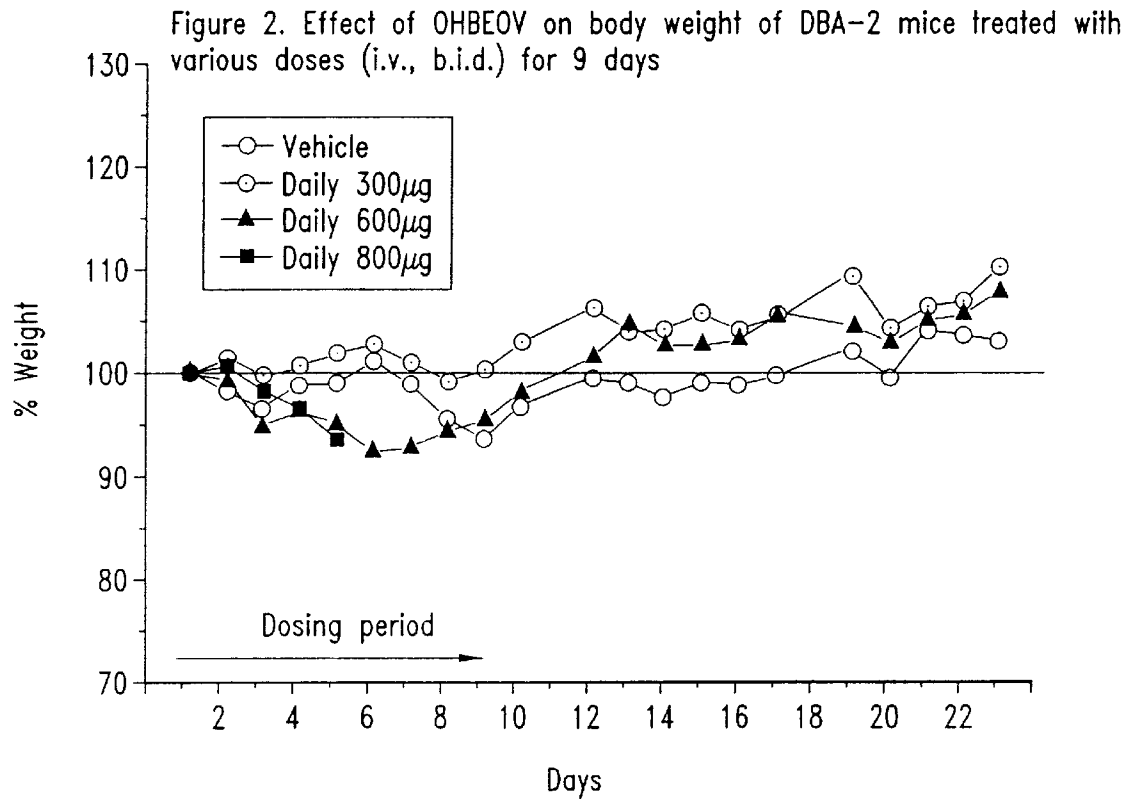
FIG. 2 is a graph showing gross toxicity of various doses (150–400 μg/dose) of OHBEOV as indicated by body weight changes in DBA-2 mice administered the complex through intravenous injection twice daily for 9 days followed by an observation period of 14 days.

Results:

Doses up to and including 300 $\mu$g (600 $\mu$g/day) were well tolerated as shown by a less than 15% weight loss through the 9 day treatment and 14 day follow up period (FIG. 2). In fact, following termination of treatment, all animals regained their original weight.

Example 35

Dose-response Efficacy Of OHBEOV Against H460 Human Non-small Cell Lung Cancer

A dose-response study was undertaken to determine the efficacy of OHBEOV using Scid/Rag-2 mice with implanted human H460 tumors (lung cancer). The purpose was to establish safe efficacious levels of s.c., b.i.d. administration of OHBEOV for 9 days. The protocol used is as follows. 20 female Scid/Rag-2 mice were randomly divided into 4 groups. Groups were treated as follows. H460 tumor cells were inoculated (50 $\mu$l $10^6$ cells bilaterally in the posterior dorsal region) as discussed earlier. On day 11 following tumor inoculation, the 9 day treatment began. Vehicle (isotonic phosphate buffer) filtered through 0.22 $\mu$m sterile filter (Costar 14066). OHBEOV was dissolved with gentle heating and stirring to a concentration of 2 mg/mL in vehicle and filtered through 0.22 $\mu$m sterile filter (Costar 140666).

The groups were as follows:

1) Vehicle control: isotonic phosphate buffer. 300 $\mu$l/dose, total of 600 $\mu$l/day.

2) 150 $\mu$l of 2 mg/mL OHBEOV mixed with 150 $\mu$l vehicle to make 300 $\mu$l to be injected for a total of 600 $\mu$g/day.

3) 200 $\mu$l of 2 mg/mL OHBEOV mixed with 100 $\mu$l vehicle to make 300 $\mu$l to be injected for a total of 800 $\mu$g/day.

4) 250 $\mu$l of 2 mg/mL OHBEOV mixed with 50 $\mu$l vehicle to make 300 $\mu$l to be injected for a total of 1000 $\mu$g/day.

Mice were weighed as a group prior to injection in the morning. Injections were s.c. in the neck region distal to the tumor sight and were delivered b.i.d. between 8–9 a.m. and between 4–5 p.m. Tumor volumes were estimated on a daily basis from measurements taken with calipers.

Treatment continued for a total of nine days. Mice were terminated on day 10 with carbon dioxide. Tumors were removed and weighed following blotting.

Figure 3:
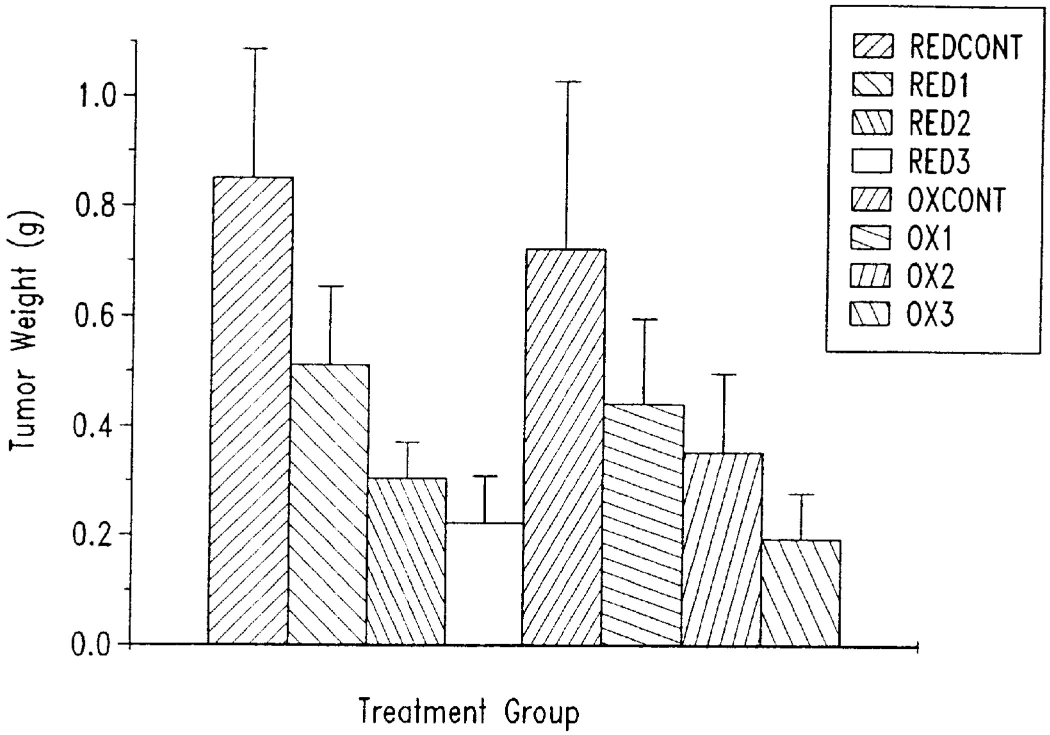
FIG. 3 is a graph showing tumor weights at the termination of a tumor efficacy study using a xenograft model of human lung cancer (H460) in immuno-compromised mice (SCID-RAG-2) treated by subcutaneous injection twice daily with various doses of BEOV or OHBEOV for nine days.
Figure 4:
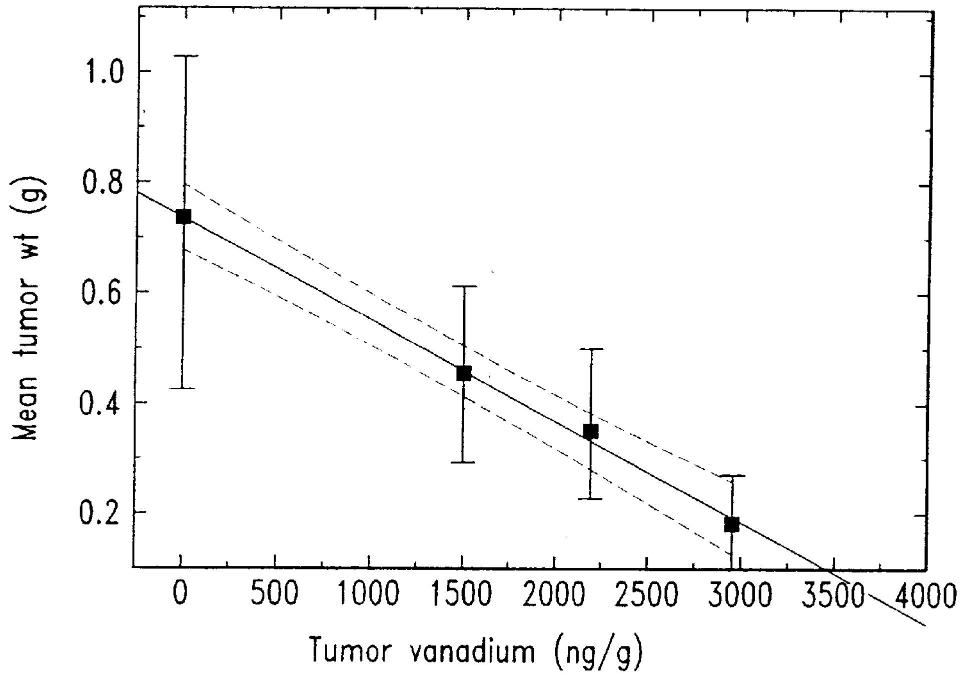
FIG. 4 is a graph relating tumor weights to concentration of vanadium measured at the end of a tumor efficacy study of OHBEOV against MDAY-D2 solid tumors.
Figure 5:
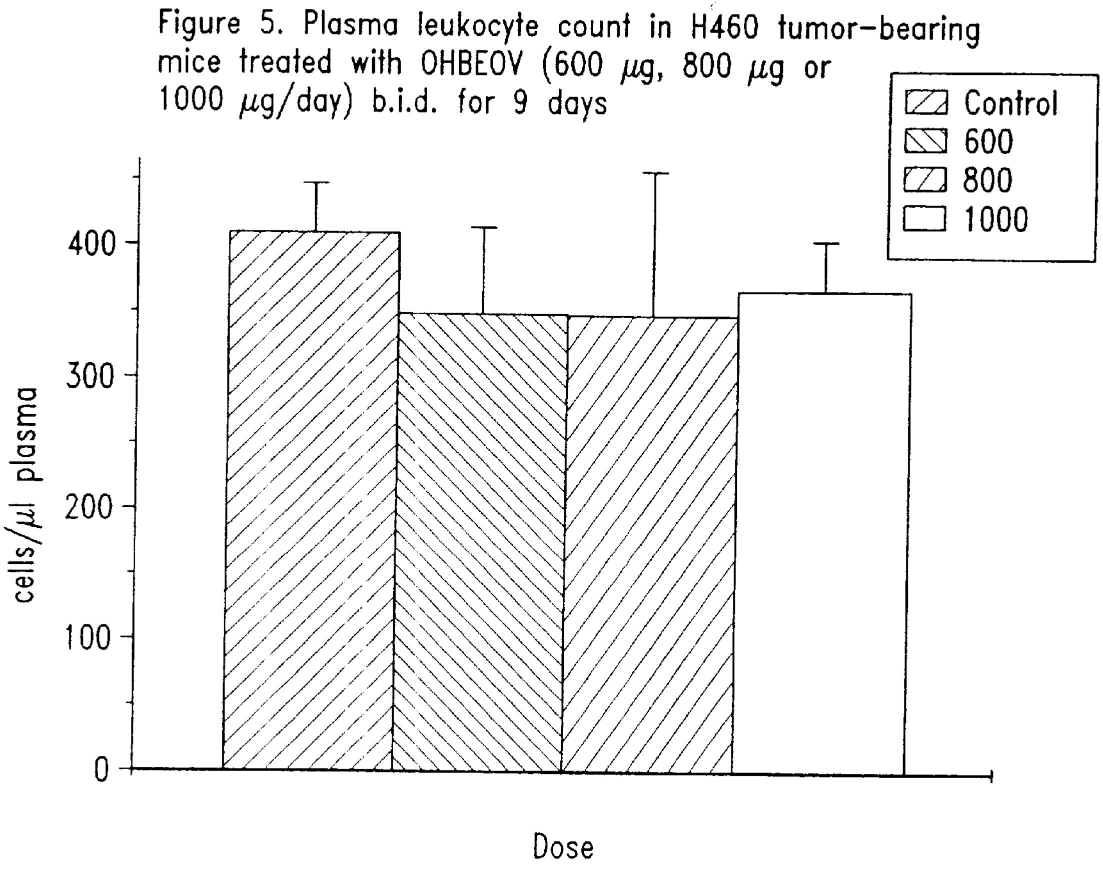
FIG. 5 is a graph depicting plasma leukocyte count following 9 day treatment of a xenograft model of lung cancer (H460) in immuno-compromised mice (SCID-RAG-2) with OHBEOV administered through s.c. injection twice daily at a total dose of 600–1000 μg/day.

Results and discussion:

Weights of tumors removed at the termination of the study (day 10) following treatment with OHBEOV showed a dose-response relationship between the daily dose of OHBEOV and mean tumor weight (FIG. 3). Determination of vanadium levels from tumors using atomic absorption spectroscopy confirmed that amount of vanadium in the tumors at the end of the study strongly correlated with mean tumor size and daily dose of drug (FIG. 4). Myelosuppression is often a dose limiting toxicity with many therapeutic agents. We therefore measured levels of leukocytes in the blood at the termination of the experiment. It was shown that there was no evidence of myelosuppression at any dose of OHBEOV tested (FIG. 5).

Example 36

Tumor Efficacy of OHBEOV on MDAY-D2 Tumors

A study was undertaken to determine the efficacy of OHBEOV using DBA-2 mice with implanted MDAY-D2

(murine lymphoma) tumor cells. The purpose was to confirm efficacious levels of s.c., b.i.d. administration of OHBEOV for 9 days at 500 μg/dose. The protocol used is as follows. 10 DBA-2 mice were randomly divided into 2 groups. Groups were treated as follows. MDAY-D2 tumor cells were inoculated (50 μl $10^6$ cells bilaterally in the posterior dorsal region) as discussed earlier. On day 11 following tumor inoculation, the 9 day treatment began. Vehicle (isotonic phosphate buffer) was filtered through 0.22 μm sterile filter (Costar 140666). OHBEOV was dissolved with gentle heating and stirring to a concentration of 2 mg/mL in vehicle and filtered through 0.22 Hm sterile filter (Costar 140666).

The groups were as follows:

1) Vehicle control: isotonic phosphate buffer. 300 μl/dose, total of 600 μl/day.

2) 250 μl of 2 mg/mL OHBEOV mixed with 50 μl vehicle to make 300 μl to be injected for a total of 1000 μg/day.

Mice were weighed as a group prior to injection in the morning. Injections were subcutaneous in the neck region distal to the tumor sight and were delivered b.i.d. between 8–9 a.m. and between 4–5 p.m. Tumor volumes were estimated on a daily basis from measurements taken with calipers. Treatment continued for a total of nine days. Mice were terminated on day 10 with carbon dioxide. Tumors were removed and weighed following blotting.

Figure 6:
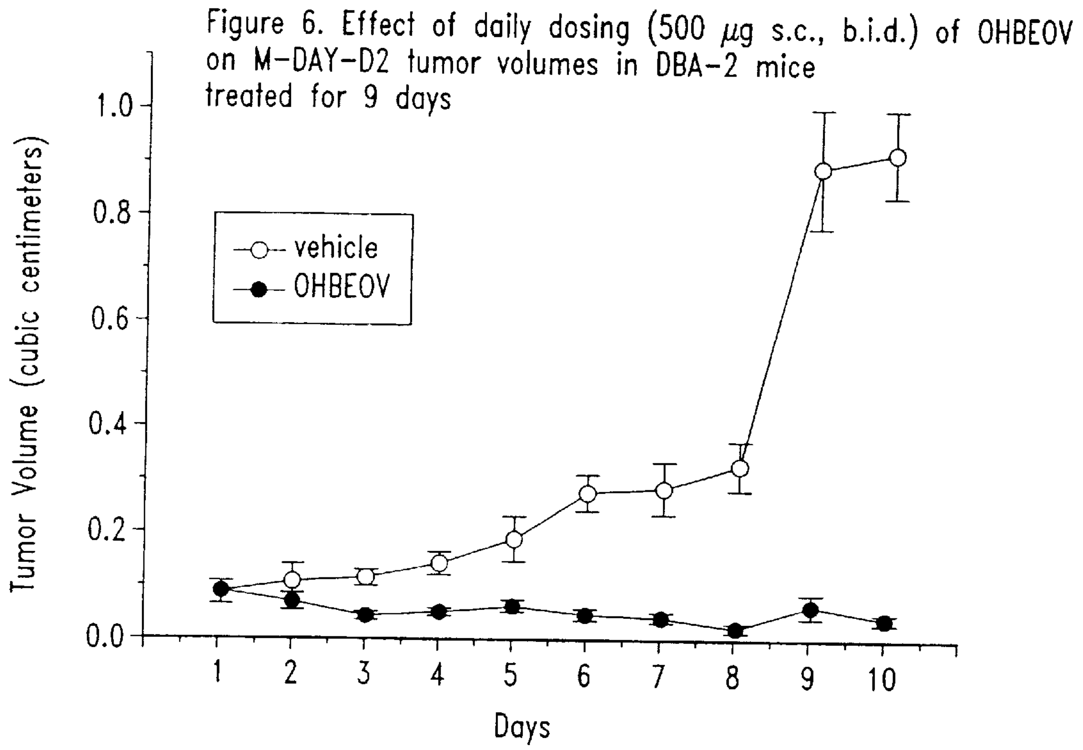
FIG. 6 is a graph showing tumor volumes derived from caliper measurements taken on a daily basis during a tumor efficacy study using a murine solid tumor model of erythroleukemia (MDAY-D2) in DBA-2 mice treated by s.c. injection twice daily with 500 μg/dose of OHBEOV for nine days.
Figure 7:
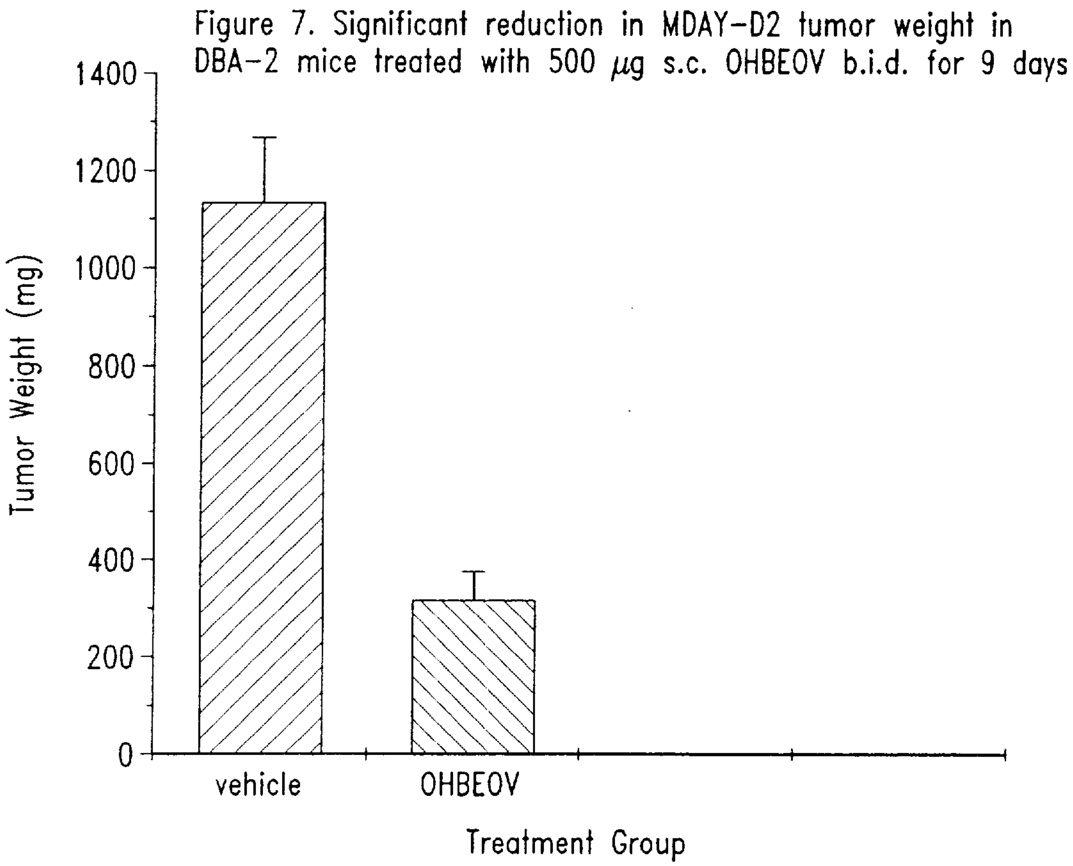
FIG. 7 is a graph showing tumor weights taken at the termination of a tumor efficacy study using a murine solid tumor model of murine lymphoma (MDAY-D2) in DBA-2 mice treated by s.c. injection twice daily with 500 ug/dose of OHBEOV for nine days.

Results and discussion:

Tumor volumes measured on a daily basis using calipers showed a significant reduction in tumor size of the treated versus control group (FIG. 6). Weights of tumors removed at the termination of the study (day 10) following treatment with OHBEOV showed a significant reduction of approximately 70% of tumor weight relative to control animals (FIG. 7).

Example 37

Efficacy of $O[BEOV]_2$ and OHBEOV on H460 (Human Non-small Cell Lung Cancer)

A study was undertaken to confirm the efficacy of OHBEOV and $O[BEOV]_2$ using SCID-RAG-2 female mice with implanted human H460 tumors (lung cancer). The purpose was to establish safe efficacious levels of s.c., b.i.d. administration of OHBEOV and $O[BEOV]_2$ for 9 days at 500 μg/dose. The protocol used was as follows. 15 SKID-RAG-2 mice were randomly divided into 3 groups. Groups were treated as follows. H460 tumor cells were inoculated (50 pl 10 6 cells bilaterally in the posterior dorsal region) as discussed earlier. On day 11 following tumor inoculation, the 9 day treatment began. Vehicle (isotonic phosphate buffer) was filtered through 0.22 pm sterile filter (Costar 140666). OHBEOV and $O[BEOV]_2$ were dissolved with gentle heating and stirring to a concentration of 2 mg/mL in vehicle and filtered through 0.22 μm sterile filter (Costar 140666).

The groups were as follows:

1) Vehicle control: isotonic phosphate buffer. 300 μl/dose, total of 600 μl/day.

2) 250 μl of 2 mg/mL OHBEOV mixed with 50 μl vehicle to make 300 μl to be injected for a total of 1000 μg/day.

3) 250 μl of 2 mg/mL $O[BEOV]_2$ mixed with 50 μl vehicle to make 300 μl to be injected for a total of 1000 μg/day.

Mice were weighed as a group prior to injection in the morning. Injections were subcutaneous in the neck region distal to the tumor sight and were delivered b.i.d. between 8–9 a.m. and between 4–5 p.m. Tumor volumes were estimated on a daily basis from measurements taken with calipers. Treatment continued for a total of nine days. Mice were terminated on day 10 with carbon dioxide. Tumors were removed and weighed following blotting.

Figure 8:
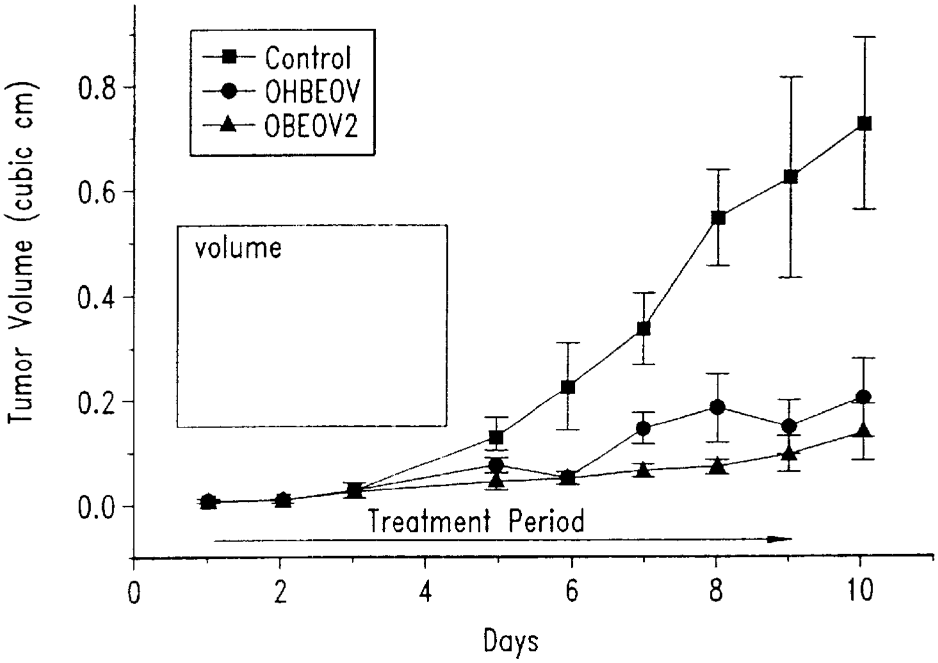
FIG. 8 is a graph showing tumor volumes derived from caliper measurements taken on a daily basis during a tumor efficacy study using a xenograft model of human lung cancer in immunocompromised (SCID-RAG-2) mice treated with OHBEOV or $O[BEOV]_2$ administered by s.c. injection twice daily for nine days.
Figure 9:
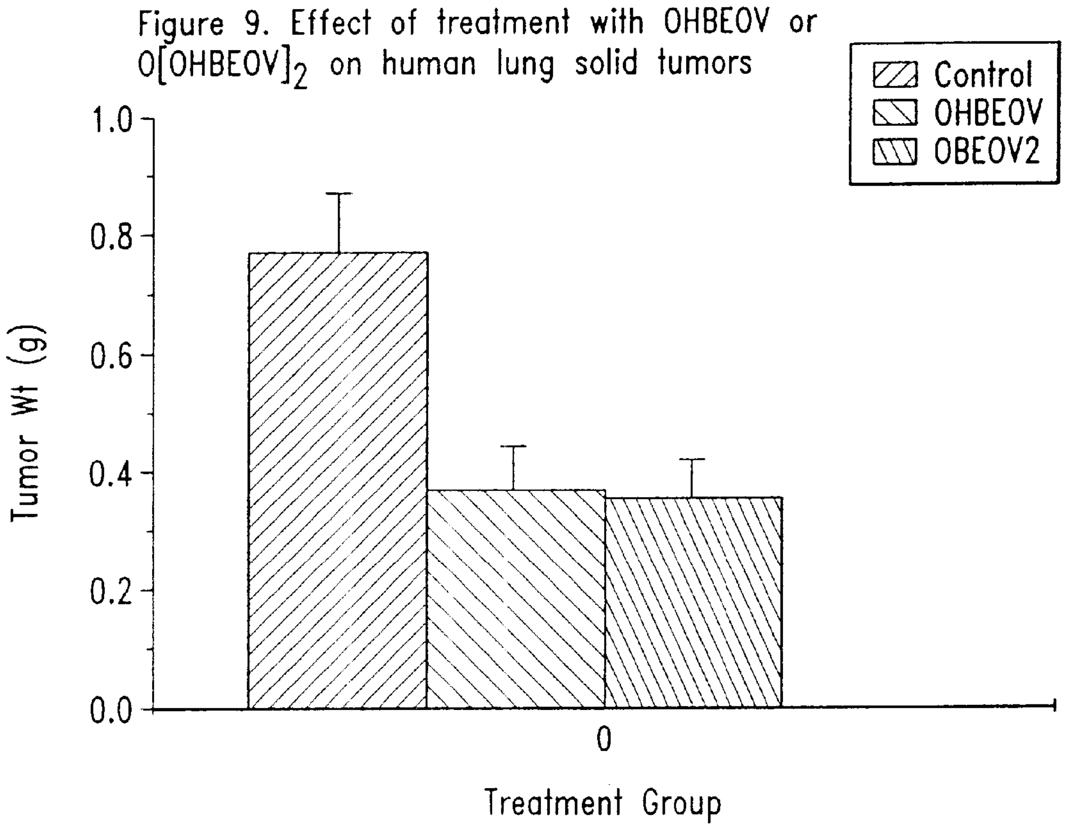
FIG. 9 is a graph showing tumor weights taken at the termination of a tumor efficacy study using a xenograft model of human lung cancer in immuno-compromised mice (SCID-RAG-2) treated with 500 μg/dose of OHBEOV or $O[BEOV]_2$ administered by s.c. injection twice daily for nine days.

Results and Discussion:

Tumor volumes measured on a daily basis using calipers showed a significant reduction in tumor size of the treated versus control group (FIG. 8). Weights of tumors removed at the termination of the study (day 10) following treatment with OHBEOV or $O[BEOV]_2$ showed a significant reduction of approximately 70% of tumor weight relative to control animals (FIG. 9).

Example 38

Experimental Protocol for Study of Vanadium Complexes on Bone Metastases

In all experiments 4-week old female nude mice receive MDA-231 cells (day 0) and subsequently were kept in an animal facility under standard conditions. Survival of mice was determined only in protocol 2.

Protocol 1: Effects of a Period of Treatment with Vanadium Complexes on Established Done Metastases.

Animals are inoculated with subconfluent MDA-231 breast cancer cells ($1\times10^5$ cells in 100 μl of phosphate buffered saline pH 7.2) in the left heart ventricle using a 27-gauge (day 0) under anesthesia with pentobarbital (0.05 mg/g) and examined for the development of osteolytic lesions by radiography at day 17. Animals showing distinct osteolytic lesions by radiography are divided in two groups. One group of mice receives PBS and another group of mice receives vanadium complexes (dose/mouse/day) s.c. once a day from day 17 to 28. At the end of the experiments, nude mice are examined again by radiography for osteolytic lesions bone metastases. Changes in numbers of osteolytic lesions are assessed by comparing the radiological films of each individual mouse taken at day 17 with those taken at day 28. Data are shown as:

$$\%\ \text{of increase} = \frac{\text{osteolytic metastasis \# at day 28} - \text{osteolytic metastasis \# at day 17}}{\text{osteolytic metastasis \# at day 17}} \times 100$$

Protocol 2: Effects of Continuous Treatment with Vanadium Complexes on the Development of New Bone Metastases.

From the same day as the inoculation of MDA-231 breast cancer cells (day 0), vanadium complexes (dose 1, 2, and 3 in pg/mouse/day) are injected s.c. once a day for 28 days. The control group receives PBS. Radiographs are taken at day 28 to assess the presence of osteolytic bone metastases. Mice are then kept untreated until they die. Survival of each animal is determined by the duration between day of cell inoculation and death.

Protocol 3: Effects of a Short Period of Prophylactic Treatment with Vanadium Complexes on the Development of New Bone Metastases.

Vanadium complexes are administered s.c. into female nude mice (3 week-old) once a day for 7 days before cell inoculation (day -7) and 7 days after inoculation. At this point, the administration of vanadium complexes is discontinued, and nude mice are then inoculated with MDA-231 breast cancer cells into the left ventricle (day 0). Radiographs of these animals are taken, and the mice are sacrificed for histological examination at day 28. Control mice receive PBS.

Radiographs and Measurement of Osteolytic Lesion Area:

Animals are radiographed in a prone position against film (X-O mat AR; Eastman Kodak Co.) and exposed at 35 KVP for 6 seconds using a Cabinet X-ray System-Faxitron Series (43855 A; Faxitron Corp., Buffalo Grove, Ill.). Films are developed using a Konica film processor. The area of osteolytic lesions is measured in both fore- and hindlimbs of all mice using an image analysis system in which radiographs are visualized using a fluorescent light box (Kaiser, Germany) and Macro TV Zoom lens 18–108 mm f2.5 (Olympus Corp., Japan) attached to a video camera (DXC-151; Sony Corp., Japan). Video images are captured using a frame grabber board (Targa+; Truevision, USA) with an IBM compatible 486/33 MHz computer. Quantitation of lesion area is performed using image analysis software (Jandel Video Analysis, Jandel Scientific, Corte Madera, Calif.).

Bone Histology and Histomorphometry:

Fore- and hindlimb long bones are removed from mice at the time of sacrifice, fixed in 10% buffered formalin, decalcified in 14% EDTA, and embedded in paraffin wax. Sections are cut using a standard microtome, placed on poly-L-lysine-coated glass slides and stained with hematoxylin, eosin, orange G, and phloxine. The following variables are measured in midsections of tibiae and femora, without knowledge of treatment groups, to assess tumor involvement: total bone area, total tumor area, and osteoclasts number expressed per millimeter of tumor/bone interface. Histomorphometric analysis is performed on an OsteoMeasure System (Osteometrics, Atlanta, Ga.) using an IBM compatible computer.

Example 39

Protocol to Study the Efficacy of Vanadium Complexes on Lung Metastases

Breast cancer MDA-231 cells are used to study the effects of the vanadium complexes on the formation of metastasis. Ten NIH Nu/Nu mice, six weeks of age (approximately) are injected by the i.v., s.c., or mammary fat pad routes with equivalent numbers of cells ($1\times10^5$ cells/animal). Animals are ear punched after injection for subsequent identification. Various doses and treatment schedules are applied to test the effect of short or continuous vanadium complex treatments on the development of established or new lung metastases. Primary tumor size is determined twice weekly by length x width measurement, and the animals are observed daily for general health. Animals with a primary tumor of 20 mm in any direction are sacrificed. At a predetermined time, based on the published literature, one or several animals of each experiment are sacrificed. The presence of metastases is determined by gross autopsy and examination of H&E stained sections of any suspicious organ and step sections of the lungs and draining lymph nodes. At any time during the experiment, animals suspected of being in distress are sacrificed.

Example 40

Protocol for Screening Assays to Determine the Mechanism of Action of Vanadium Complexes Mammalian cells carrying AP-1 or NF-KB reporter luciferase gene constructs are simultaneously submitted to growth factors and cytokines (EGF, TNF, IL-1B, PDGF, VEGF, IGF-1, etc.) and to various vanadium complexes. This protocol allows the identification of the signal transduction pathways that are affected by the vanadium complexes. Once a signal transduction pathway is identified as being a target, the vanadium complexes are screened to determine which one has the highest activity in that specific transduction pathway. Also, specific enzymatic assays (JNK, MAPK, p38) are carried out in parallel to validate the screening process. The enzymes chosen reflect indirectly AP-1 or NF-KB activities.

Example 41

The Effect of $O[BEOV]_2$ on Drug Resistant Cell Lines

Three ovarian cancer cell lines, which have increasing drug resistance (KB8, Kb8-5 and KB85-1 1) to the parent cell line, KB3-1, are used to determine the effect of $O(BEOV)_2$ on resistant cell lines in vitro. These drug resistant cell lines are resistant to colchicine, vinblastine and doxorubicin. All four cell lines are incubated in media (DMEM) containing 0 to 50 $\mu$M $O[BEOV]_2$ and after 24–72 hours the number of viable cells is determined.

Previous studies with other vanadium complexes revealed that agents such as orthovanadate were equally toxic to all the drug resistant cell lines.

Example 42

Cytotoxicity Assays

The relative cytotoxicity of vanadium complexes on tumor cell lines was measured using the MTT microculture tetrazolium colorimetric assay.

The relative cytotoxicity of a variety of vanadium complexes ($Na_3VO_4$, $VOSO_4$, BMOV, BEOV and Naglivan) was determined using the following tumor cell lines: P388 (WT) (murine leukemia), P388 (ADR) (murine leukemia), Lewis Lung (murine lung), MCF7 (WT) (human breast), MCF7 (ADR) (human breast), H460 (human non-small lung), K562 (human erythroleukemia), A431 (human epidermal), LS180 (human colon) and SK-OV-3 (human ovarian).

Cells were plated (number of cells/well was different from cell line to cell line depending on the dividing rate) in a 96-well microculture plate for 24 hours prior to treatment with the vanadium complexes. Serial concentrations of solutions of the test complexes (0.05 to 100 $\mu$M) were delivered to the corresponding wells and incubated up to 72 hours. A blank column (without cells) and a control column (with cells without vanadium) were also used. After the incubation period, an MTT dye solution was added to the wells for an additional 4-hour incubation time. The medium was removed and DMSO was added to each well. The absorbance of each well was read with a Titertek Multiskan (310C) spectrophotometer at 570 nm. The absorbance of each vanadium concentration relative to the control and the value of the 50% growth inhibition concentration ($IC_{50}$) was obtained from the percent control versus concentration plot. Each assay was repeated three times and the reported $IC_{50}$ values were the mean of these three runs.

This protocol can be used to assess the relative cytotoxicity of various vanadium complexes.

Example 43

The Effect of $O(BEOV)_2$ on Cellular Proliferation in vitro Is Determined Using Normal Non-Proliferating and Proliferating Cells To compare the anti-proliferative effects of $O[BEOV]_2$ with other vanadium complexes, the activity of $O[BEOV]_2$ in normal non-proliferating and proliferating cells is determined.

Chondrocytes are plated and maintained for 48 hours at both high cell density ($2\times10^6$ to $4\times10^6$ cells/per well on a six well plate) (non-proliferating) and low cell density ($5\times10^5$ to $1\times10^6$ cells/per well on a six well plate) (proliferating). For an additional 48 hours, the cells are incubated in media (HAMS F12) containing 0 to 50 $\mu$M O[BEOV]$_2$. The number of viable cells is then determined.

In previous studies, orthovanadate did not affect the non-proliferating cells although it was toxic to proliferating cells.

Example 44

Initial Assessement of Anti-diabetic Potential of O [BEOV]$_2$

Experiments to determine the pharmacological effectiveness of O[BEOV]$_2$ against diabetes are carried out as follows. Male Wistar rats are made diabetic by i.v. injection of streptozotocin (STZ) as a single dose of 60 mg/kg dissolved in 0.9% saline.

O[BEOV]$_2$ can be administered through several routes of administration. O[BEOV]$_2$ is given as a suspension in 1% methyl cellulose at a range of doses (approximately 15 mg/kg). Administration of O[BEOV]$_2$ can also given in separate experiments by oral administration in drinking water given ad libitum to rats at a concentration of between 0.2–2.0 mg/mL. O[BEOV]$_2$ can also be given through oral gavage at a dose of 100–200 $\mu$mol/kg. Blood glucose levels are measured at intervals using a test strip and glucometer obtained commercially.

Example 45

Treatment of Diabetes with O[BEOV]$_2$

Experiments to determine the long-term pharmacological effectiveness of O[BEOV]$_2$ against a model of type II diabetes are carried out as follows. Male (Wistar) rats are made diabetic by i.v. injection of streptozotocin (STZ) as a single dose of 60 mg/kg dissolved in 0.9% saline via the tail vein. Control groups are injected with saline vehicle only.

O[BEOV]$_2$ is administered to normal and STZ-treated rats via drinking water. Four groups are established as follows: control, diabetic, control-treated, diabetic-treated. The diabetic state is confirmed with a "Testape" at 3 days post-injection and later confirmed with a glucometer test. Blood glucose and insulin levels are measured through the course of the study. Treatment is started 1 week following STZ injection.

Treated animals receive 0.1–1.0 mmol/kg of the complex/day in drinking water over a 3 month period. Parameters measured at various time-points through the study include animal weight, blood glucose levels, food consumption, fluid consumption, glycosylated hemoglobin, plasma triglycerides and cholesterol levels. Secondary complications of diabetes included cataract development, neuropathy, and cardiomyopathy are assessed through standard procedures.

Example 46

Vanadium Treatment of Hypertension

Insulin resistant spontaneously hypertensive rats (SHR) are used as a model for treatment by O[BEOV]$_2$. These SHR spontaneously hypertensive rats are insulin resistant and hyperinsulinemic in comparison to their genetic controls, the Wistar Kyoto (WKY) strain. For the typical experiment, rats are obtained at 4 weeks of age and divided into 4 groups as follows: SHR (untreated), SHRVan (vanadium-treated), WKY (untreated), WKYVan (vanadium-treated). O[BEOV]$_2$ is administered (0.1–2.0 mg/mL) in drinking water given ad libitum to the SHRVan and WKYVan groups at 5 weeks of age on a constant basis. Following week 8, when hypertension is fully manifest in the SHR, weekly measurements of plasma insulin and systolic blood pressure (tail cuff method, or implanted arterial catheters) are taken in all groups. Weekly measurements of blood pressure are taken and blood samples collected for subsequent glucose and insulin analysis. As a part of this experiment, the effects of O[BEOV]$_2$ are assessed for its appetite suppression effects by measuring weight gain.

Example 48

The Effect of O[BEOV]$_2$ on Synoviocyte Proliferation

Incubating plated synoviocytes with O[BEOV]$_2$ for 24 hours assesses the effect of O[BEOV]$_2$ on synoviocyte proliferation. The number of viable cells is determined by the dye exclusion method.

It has been previously shown that other vanadium complexes, such as orthovanadate and vanadyl sulphate, inhibited synoviocyte proliferation and were cytotoxic to the cells.

Example 49

Treatment of Collagen Induced Arthritis (CIA) BY O[BEOV]$_2$

CIA in rats is a model of chronic inflammatory synovitis with pannus formation, neovascularization, and joint destruction similar to rheumatoid arthritis (RA). After immunization with native collagen type II (CII) in incomplete Freund's adjuvant, 90–100% of genetically susceptible rats reliably develop clinical arthritis within 10 to 14 days.

Arthritis is induced in syngeneic 8 week old female Louvain (LOU) rats by intradermal immunization under ether anaesthesia on Day 0 with 0.5 mg native chick collagen II (CII) (Genzyme, Boston, Mass.) solubilized in 0.1M acetic acid and emulsified in incomplete Freund's adjuvant (IFA) (Difco, Detr, Mich.) (D. E. Trentham et al., *J. Exp. Med.* 146:857–868, 1977). Onset of clinical arthritis typically develops in 90–100% of control rats 10–12 days post CII immunization.

On day 10 post immunization, arthritis-induced rats are randomized into two groups. Control rats (n=10) receive only an aqueous vehicle at a dose of 100 mg/kg/day s.c. The experimental group (n=10) receives an aqueous vehicle at 100 mg/kg/day s.c., as well as O[BEOV]$_2$ subcutaneously at the appropriate dose.

The severity of clinical arthritis in each limb is scored daily based on an objective integer scale of 0–4 (D. E. Trentham et al., *J. Exp. Med.* 146:857–868, 1977). A score of 0 indicates an unaffected limb, while a score of 4 represents fulminant erythema and edema involving distal digits. The arthritic index is defined as the sum of its four limb scores. Since CIA typically involves only the hind limbs, an arthritic index of 6 to 8 is considered to represent severe arthritis.

At the end of the study (Day 18-post arthritis onset), hind limb radiographs are obtained. An investigator blinded to the treatment protocol assigns a score to each limb, based on the degree of soft tissue swelling, joint space narrowing, periosteal new bone information, and the presence of erosions and ankylosis (0=normal; 3=maximal joint destruction). The radiographic index is defined as the sum of the limbs.

The humoral immunity is evaluated by collecting rat serum on Day 18 post arthritis onset for measuring anti-CII IgG by an enzyme linked immunosorbent assay (ELISA) (E. Brahn and D. E. Trentham, *Cell Immunol.* 86:421–428, 1984; E. Brahn and D. E. Trentham, *Cell Immunol.* 118:491–503, 1989). Antibody titers are normalized against a previously standardised curve and absorbance read at 490 nm at a serum dilution of 1:2500.

Synovium is selected from rats on Day 5 and Day 18-post arthritis onset to study joint morphology using electron microscopy. On Day 18-post arthritis onset, one ankle joint of each arthritic control and $O[BEOV]_2$-treated rat is removed, critical point dried, and gold sputter-coated for scanning electron microscopy to examine the trochlear surfaces. Conventional transmission electron microscopy is also performed on the articular cartilage of the trochlear surfaces of native, arthritic control, and $O[BEOV]_2$-treated animals.

Example 50

Prevention of Arthritis Onset by $O[BEOV]_2$ in the CIA Rat Model

The ability of $O[BEOV]_2$ to prevent arthritis when administered prior to clinical arthritis onset will be assessed in the CIA rat model (Brahn et al., 1994; Oliver et al., 1994). CIA is a T cell-dependent animal model of the disease that is induced by immunization of the animals with type II collagen.

Syngeneic female Louvain rats weighing 120 to 150 grams are injected intradermally with 0.5 mg of native chick collagen II (Genzyme, Boston, Mass.) solubilized in 0.1M acetic acid and emulsified in FIA (Difco, Detroit, Mich.). Approximately 9 days after immunization, animals develop a polyarthritis with histologic changes of pannus formation and bone/cartilage erosions. Animals are randomized into 2 groups: a control group (n=10) that receives vehicle alone and a $O[BEOV]_2$ treatment group (n=10). In order to evaluate the effect of $O[BEOV]_2$, $O[BEOV]_2$ is administered i.p. or s.c. beginning on day 2 after immunization (prevention protocol). For the prevention protocol (n=10), $O[BEOV]_2$ is given on day 2 with 5 subsequent doses on days 5, 7, 9, 12 and 14. The control and experimental animals are evaluated for disease severity both clinically and radiographically by individuals blinded to treatment groups.

The severity of inflammation for each limb is evaluated daily and scored based on standardized levels of swelling and periarticular erythema (0 being normal and 4 severe). Animals are evaluated radiographically on day 28 of the experiment. The radiographs of both hind limbs are graded by the degree of soft tissue swelling, joint space narrowing, bone destruction, and periosteal new bone formation. A scale of 0–3 is used to quantify each limb (0=normal, 1=soft tissue swelling, 2=early erosions of bone, 3=severe bone destruction and/or ankylosis). Histological assessment of the joints is completed at the conclusion of the experiment.

Delayed-type hypersensitivity (DTH) to CII is determined by a radiometric ear assay completed on day 28. Radiometric ear indices $\geqq 1.4$ represent a significant response to CII. The presence of anti-CII IgG antibodies is determined by enzyme-linked immunosorbent assay (ELISA). Serum samples obtained on day 26 are diluted to 1:2,560, and the results are expressed as the mean optical density at 490 nm, in quadruplicate aliquots. Background levels in normal rat serum at this dilution are 0 and are readily distinguishable from collagen-immunized rat serum.

Example 51

Treatment of Collagen Induced Arthritis with Bis (maltolato)oxovanadium(IV) (BMOV)

Rats given BMOV and NAC demonstrated significant regression of established arthritis compared to controls within two days post arthritis onset ($p<0.05$). Control rats, receiving NAC alone, developed severe arthritis, a result suggesting that the reducing agent per se did not modify arthritis development significantly. The difference between the mean daily arthritis scores of the control and the experimental groups remained significant throughout the rest of the study period ($p<0.005$ on Day 18-post arthritis onset). The mean radiological scores of the experimental group was significantly lower than the control group ($p<0.005$). All experimental rats tolerated the combination of BMOV and NAC without weight loss. Diarrhoea was not observed when BMOV was given at a dose of 10 mg/kg/day. However, when the dose was increased to 15 mg/kg/day on Day 11 post arthritis onset, a several experimental rats manifested minor diarrhoea.

The mean anti-CII IgG titer of the control group was significantly higher than that of the experimental group ($p<0.004$). The biological significance of this difference, however, remained unclear since the magnitude of the difference was minimal and previous experiments have shown that arthritic rats often produce higher titers of anti-CII IgC than non-arthritic rats.

X-rays of control and experimental rat limbs illustrated a typical arthritic control limb as having soft tissue swelling and bone erosion. These features are absent in the vanadate treated experimental limb.

The articular cartilage of control rats was characteristically scabrous with an excessive number of erosion sites, pits and adhering cells. In contrast, the BMOV-treated rats exhibited a normal trochlear surface characterized by scant adhering elements and a smooth articular surface with orderly arranged collagen fibrils. Articular surface was mechanically damaged during dissection.

Transmission electron micrographs show the typical ultrastructure of the native animal as contrasted with that of the arthritic control having its articular surface overgrown with cells and pitted surface. On the other hand, the articular cartilage of BMOV-treated animals appeared indistinguishable from the native animal.

The scanning and transmission electron micrographs demonstrated dramatic cartilage destruction in the control joints with exposed or absent chondrocytes in the denuded cartilage. Joints from BMOV-treated rats demonstrated little cartilage damage and intact cartilage.

Northern blots of collagenase, stromelysin and IL-1 illustrate that synovial expression of collagenase, stromelysin, and to a lesser degree, IL-1, were reduced in the BMOV group compared to the control group. Collagenase, stromelysin, and IL-1 mRNA were readily detected in the vehicle control group. When normalized for RNA loading, expression of all three genes was decreased in the animals in the BMOV-treated group compared to the control group. The percent inhibition of collagenase, stromelysin, and IL-In gene expression were 78%, 58% and 85% respectively.

The results show that the combination of BMOV and NAC significantly regressed established CIA, compared to the control using NAC alone, by both clinical and radiologic criteria. The results indicate that the combination of vanadate and NAC regressed established CIA via decreasing collagenase expression. Collagenase mRNA expression in control arthritic rats were significantly higher than that in combination treated non-arthritic rats. Furthermore, the scanning electron micrographs showed much erosion in the synovium of control joints, with chondrocytes exposed to the synovial surface. In contrast, the surface of combination treated synovium had a smooth appearance without chondrocytes exposed. The single agent NAC had no appreciable effect on the clinical severity of CIA. The combination of vanadate and NAC demonstrated efficacy at regressing established CIA due to at least two molecular mechanisms: decreased collagenase gene expression and decreased hydrogen peroxide concentration.

Example 52

Effects of O[BEOV]$_2$ in an Animal Model of Multiple Sclerosis

The ability of O[BEOV]$_2$ to inhibit the progression of MS symptoms and pathogenesis is examined in a demyelinating transgenic mouse model (Mastronardi et al., 1993; 1996). This transgenic mouse contains 70 copies of the transgene DM20, a myelin proteolipid, and appears normal up to 3 months of age. The signs of MS such as seizures, shaking, hind limb immobility, unsteadiness of gait, limp tail and reduction in the degree of activity appear at this time and increase in severity with time until the animal dies between 6 to 8 months. The progression of the disease is scored from 0 to 4+. Control animals progress from 1+ to a 4+ scoring over the 27 days in a number of symptoms; 3+ characterizes animals with poor balance and extreme mobile deficiencies. The clinical signs correlate with the demyelination and increased fibrous astrocyte proliferation in the brain.

Demyelinating transgenic mice are treated with O[BEOV]$_2$ (n=5) or are left as untreated normal (n=1) or untreated transgenic littermate (n=1). Only one transgenic mouse is used as a control because the course of the disease is well established in the laboratory. The four-month-old animals are injected with O[BEOV]$_2$ after the initial signs of MS reach a score of 1+in the symptoms described above. The course of treatment is spread over 24 days by treating the animals with O[BEOV]$_2$ every three days (or alternate dosing schedule based on maximum tolerated dose studies). The body weight and clinical signs described above are determined on each injection day.

Three days following the tenth injection, the experimental study is terminated and the brain tissues are processed for histological analysis. For light microscopy, tissues are formalin fixed and paraffin embedded. Sections of 5 microns are stained with anti-GFAP antibody (DACO), washed and then reacted with secondary antibody conjugated with HPP. The sections are stained for HPP and counter-stained with haematoxylin. For electron microscopy, tissues are fixed in 2.5% glutaraldehyde and phosphate buffer pH 7.2, and post fixed with 1% ammonium tetroxide in phosphate buffer. Eighty nanometer sections are prepared and viewed with a JEOL 1200 EX II transmission EM.

Example 53

Characterization of Activity of O[BEOV]$_2$ on Human Epidermal Keratinocytes in vitro The time and dose-dependent effects of O[BEOV]$_2$ is determined using actively proliferating normal human keratinocytes and HaCAT keratinocytes (spontaneously immortalized human epidermal keratinocytes).

The effect of O[BEOV]$_2$ on keratinocytes is assessed by determining the cell number and $^3$H-thymidine incorporation by the cells. For thymidine incorporation, keratinocytes plated at low density (in DMEM, supplemented with 10% FCS, glutamine, antibiotics) are treated with O[BEOV]$_2$ concentrations of 0 to $10^{-4}$M for 6 hours during logarithmic growth. $^3$H-thymidine is added to the cells and incubated for a further 6 hours. The cells are harvested and radioactivity determined. To determine the total cell numbers, keratinocytes are plated as described and incubated in the presence and absence of O[BEOV]$_2$ for 4 days. Following incubation, cells are collected and counted by the trypan blue exclusion assay.

Example 54

Development of Topical Formulations of O[BEOV]$_2$ for the Treatment of Psoriasis Keratinocyte mitosis occurs almost exclusively in the basal layer of the epidermis and therefore to combat hyperproliferation O[BEOV]$_2$ must reach the cells of this layer. In vitro testing using an animal skin model will determine the most likely formulation candidates. Mini-pig skin will be used as it most closely approximates the human skin permeation barrier.

The topical formulation comprises the following: Labrafil® M2130CS 25%), Labrasol® (25%), Transcutol® (25%), Arlacel® 165 (12%), isopropyl myristate (10%) and Compritol (3%). O[BEOV]$_2$ is dissolved in the formulation concentration of 0.1 %w/w. A specific weight of formulation is applied to excised, dermis removed mini-pig skin mounted on Franz diffusion cells maintained at 37° C. After 24 hours, the skin is washed clean and removed from the diffusion cells. All fluids are kept and assayed for vanadium via atomic absorbance spectroscopy. The skin is microtomed into sections, and the concentration and distribution of vanadium is determined in each section via atomic absorbance spectroscopy. The sectioned skin is also used to determine where vanadium resides in each section. Both treated and untreated skin samples are examined through light and electron microscopy.

Example 55

Development of Systemic Formulations of O[BEOV]$_2$ for the Treatment of Psoriasis In severe cases of psoriasis, more aggressive treatments are deemed acceptable and therefore the potential toxicities associated with systemic treatment with O[BEOV]$_2$ may be acceptable.

One type of systemic formulation for O[BEOV]$_2$ is comprised of amphiphilic diblock copolymers of micelles consisting of a hydrophobic core and a hydrophilic shell in water. Diblock copolymers of poly(DL-lactide)-block-methoxy polyethylene glycol (PDLLA-MePEG), polycaprolactone-block-methoxy polyethylene glycol (PCL-MePEG) and poly(DL-lactide-co-caprolactone)-block-methoxy polyethylene glycol (PDLLACL-MePEG) can be synthesized using a bulk melt polymerization procedure, or similar methods. Briefly, given amounts of monomers DL-lactide, caprolactone and methoxy polyethylene glycols with different molecular weights are heated (130° C.) to melt under the bubbling of nitrogen and stirring. Catalyst stannous octoate (0.2% w/w) is added to the molten monomers. The polymerization is carried out for 4 hours. The molecular weights, critical micelle concentrations and the maximum O[BEOV]$_2$ loadings are measured with GPC, fluorescence and solubilization testing respectively.

The strong association within the internal core of the polymeric micelles presents a high capacity environment for carrying drugs such as O[BEOV]$_2$. The agents may be coupled to block copolymers to form a micellar structure or can be physically incorporated within the hydrophobic cores of the micelles. The mechanisms of drug release from the micelles include diffusion from the core and the exchange between the single polymer chains and the micelles. The small size of the micelles (normally less than 100 nm) will eliminate the difficulties associated with injecting larger particles.

Example 56

Evaluation of O[BEOV]$_2$ Formulations in Animal Models of Psoriasis

A novel animal model is used to investigate skin-specific angiogenesis.

Immunodeficient SCID mice are used as recipients for surface transplants of human keratinocyte lines transfected with vascular endothelial growth factor (VEGF) in sense or antisense orientation. Keratinocytes are transplanted via use of modified silicon transplantation chamber assay onto the skin of recipient mice. Keratinocytes are allowed to differentiate and to induce skin angiogenesis. O[BEOV]$_2$ is then given either systemically or topically (cream, ointment, solution suspension, lotion, gel), and morphometric measurements of vessel numbers and sizes are performed in untreated and treated groups.

The mouse model for cutaneous delayed type hypersensitivity reactions is used to investigate the effects of O[BEOV]$_2$ on induced skin inflammation. Mice are sensitized to oxazolone by topical application of the compound onto the skin. Five days later, mice are challenged with oxazolone by topical application onto the ear skin (left ear: oxazolone, right ear: vehicle alone), resulting in a cutaneous inflammatory, "delayed-type hypersensitivity" reaction. The extent of inflammation can be quantified by measurements of the resulting ear swelling over a period of 48 hours. Epon-embedded, Giemsa-stained, 1 $\mu$m-tissue sections are evaluated for the presence of inflammatory cells, for the presence of tissue mast cells and their state of activation, and for the degree of epidermal hyperplasia. O[BEOV]$_2$ is given either systemically or topically to quantitate its effect on the cutaneous inflammatory reaction in this in vivo model.

Example 57

Treatment of Atherosclerosis'

Atherosclerotic lesions are created in New Zealand white rabbits by diet only. Briefly, New Zealand white rabbits weighing approximately 1.6 kg are placed on a powdered chow supplemented by 0.25% cholesterol by weight. Total plasma cholesterol is measured on a weekly basis by taking samples from a marginal ear vein after an injection of Innovar (0.1 ml/kg) to dilate blood vessels. Samples are mixed with EDTA to achieve a 0.15% concentration in the sample and placed on ice until separation of plasma by low speed centrifugation.

One week after initiation of the full cholesterol diet, the animals are randomized into 3 groups of 10. After anaesthetic induction with Ketamine 35 mg/kg and Xylazine 7 mg/kg, and then general anesthesia via intubation, the fur is shaved and the skin sterilized over the abdomen. A laparotomy is performed and the abdominal aorta isolated. Using a 22 g needle, ethylene vinyl acetate paste, ethylene vinyl acetate paste containing 5% O[BEOV]$_2$ complex, or ethylene vinyl acetate paste containing 33% O[BEOV]$_2$ complex is placed in a circumferential manner around the proximal half of the infrarenal abdominal aorta. The distal half of the aorta extending to the aortic bifurcation is not treated, In 10 control rabbits, the infrarenal abdominal aorta is isolated, but nothing is injected around it.

The atherogenic chow is continued for 24 weeks. At that time, the animals are anesthetized with an injection of Ketamine (350 mg/kg) and Xylazine (7 mg/kg) intramuscularly and then sacrificed with an intravenous overdose of Euthanol (240 mg/ml; 2 ml/4.5 kg). The animals are then perfusion fixed at 100 mm mercury via the left ventricle by perfusing Hanks' balanced salt solution with 0.15 mmol/liter N-2-hydroxyethylpaparazine-N'-2-ethanesulfonic acid (pH 7.4) containing Heparin (1 IU/mL) for ten minutes followed by dilute Kamovsky's fixative for 15 minutes. The thoracic and abdominal aorta and iliac arteries are removed en bloc and are placed in a similar solution for a further 30 minutes.

Serial thin sections are then performed through the thoracic aorta and particularly through the infrarenal abdominal aorta. Movat, H&E, and Masson stains are performed and histologic analysis made to examined the degree of luminal compromise, the degree of atherosclerotic lesion development, and any perilumenal reaction to the circumferential arterial medications.

Example 58

Treatment of Restenosis

Wistar rats weighing 250–300 g are anesthetized by the intramuscular injection of innovar (0.33 ml/kg). Once they are sedated they are placed under Halothane anesthesia. After general anesthesia is established, the fur over the neck region is shaved and the skin cleansed with Betadine. A vertical incision is made over the left carotid artery and the external carotid artery exposed. Two ligatures are placed around the external carotid artery and a transverse arteriotomy is made between them. A 2 Fr Fogarty balloon catheter is introduced into the external carotid artery and passed into the left common carotid artery and the balloon is inflated with saline. The catheter is passed up and down the carotid artery three times to denude the endothelium. The catheter is removed and the ligatures tied off on the left external carotid artery.

The animals are randomized into groups of 5. Subgroups of 5 rats are control, carrier polymer alone, carrier polymer plus 1, 5, 10, 20, and 33% O[BEOV]$_2$ complex is delivered. There are two carrier polymers to be investigated; EVA and EVA/PLA blend. The polymer mixture is placed in a circumferential manner around the carotid artery. The wound is then closed. Rats in each group are sacrificed at 14 and 28 days. In the interim, the rats are observed for weight loss or other signs of systemic. After 14 or 28 days, the animals are sacrificed by initial sedation with intramuscular Innovar (0.33 ml/kg). The arteries are then examined for histology.

Example 59

Intimal Hyperplasia Causing Graft Stenosis

General anesthesia is induced into domestic swine. The neck region is shaved and the skin sterilized with cleansing solution. Vertical incisions are made on each side of the neck and the carotid artery is exposed and 8 mm PTFE graft inserted by 2 end to side anastomoses, the proximal anastomosis on the common carotid artery and the distal anastomosis on the internal carotid artery bilaterally. The intervening bypassed artery is ligated. The animals are randomized into groups of 10 pigs receiving carrier polymer alone, 10 pigs receiving carrier polymer plus 5% w/w $O[BEOV]_2$ complex, and 10 pigs receiving carrier polymer plus 33% w/w $O[BEOV]_2$ complex adjacent to each surgical created anastamosis on the left side only. The right sided grafts will serve as a control in each pig. The wounds are closed and the pigs recovered.

A second group of pigs are studied. The grafts are created in a similar manner. No vasoactive agent is placed next to the anastamotic sites at the time of operation. The animals are recovered. Two weeks after the graft has been performed, a second general anaesthetic is administered and the left carotid artery is reexplored. Adjacent to the proximal and distal anastamoses, 10 pigs each receive carrier alone, carrier polymer plus 5% w/w $O[BEOV]_2$ complex and carrier polymer plus 33% w/w $O[BEOV]_2$ complex in a circumferential manner adjacent to both proximal and distal anastamoses. The wounds are closed and the pigs recovered. Opposite the right sided graft serves as a control.

At 3 months, all pigs undergo general anesthetic. A cutdown is made on the femoral artery and a pigtail catheter is inserted in the ascending thoracic aorta under fluoroscopic guidance. Arch injection with imaging of the carotid vasculature is performed. Specifically, the degree of stenoses of the proximal and distal grafts and the artery immediately distal to the distal anastamosis of the graft is measured and the % stenosis calculated. If necessary, selective injections of the common carotid arteries are performed.

Five pigs in each group are sacrificed. The animals are then perfusion fixed at 100 mm mercury via the left ventricle by perfusing Hanks' balanced salt solution with 0.15 mmol/liter N-2-hydroxyethylpaparazine-N'-2-ethanesulfonic acid (pH 7.4) containing Heparin (1 IU/mL) for ten minutes followed be dilute Kamovsky's fixative for 15 minutes. The thoracic and abdominal aorta and carotid arteries are removed en bloc and are placed in a similar solution for a further 30 minutes.

Histological sections through the carotid artery immediately proximal to the proximal anastamosis, at the proximal anastamosis, at the distal anastamosis and the carotid artery immediately distal to the distal anastamosis are made. The sections are stained with Movat and H&E and Masson stains. Histologic analysis of intimal and advantitial reaction as well as perivascular reaction are noted. Morphometric analysis with degree of luminal narrowing is calculated.

The remaining pigs are studied at 6 months and a similar angiography sacrifice procedures is performed.

Example 60

Manufacture of "Pastes"

As noted above, the present invention provides a variety of polymeric-containing drug compositions that may be utilized within a variety of clinical situations. For example, compositions may be produced: (1) as a "thermopaste" that is applied to a desired site as a fluid, and hardens to a solid of the desired shape at a specified temperature (e.g., body temperature); (2) as a spray (i.e., "nanospray") which may delivered to a desired site either directly or through a specialized apparatus (e.g., endoscopy), and which subsequently hardens to a solid which adheres to the tissue to which it is applied; (3) as an adherent, pliable, resilient, angiogenesis inhibitor-polymer film applied to a desired site either directly or through a specialized apparatus, and which preferably adheres to the site to which it is applied; and (4) as a fluid composed of a suspension of microspheres in an appropriate carrier medium, which is applied to a desired site either directly or via a specialized apparatus, and which leaves a layer of microspheres at the application site. Representative examples of each of the above embodiments is set forth in more detail below.

A. Procedure for Producing Thermopaste

Reagents and equipment which are utilized within the following experiments include a sterile glass syringe (1 mL), Corning hot plate/stirrer, 20 mL glass scintillation vial, molds (e.g., 50 μl DSC pan or 50 mL centrifuge tube cap inner portion), scalpel and tweezers, Polycaprolactone ("PCL"—mol wt 10,000 to 20,000; Polysciences, Warrington, Pa. USA), and $O[BEOV]_2$.

Weigh 5.00 g of polycaprolactone directly into a 20 mL glass scintillation vial. Place the vial in a 600 mL beaker containing 50 mL of water. Gently heat the beaker to 65° C. and hold it at that temperature for 20 minutes. This allows the polymer to melt. Thoroughly mix a known weight of $O[BEOV]_2$ into the melted polymer at 65° C. Pour the melted polymer into a pre-warmed (60° C. oven) mould. Use a spatula to assist with the pouring process. Allow the mould to cool so the polymer solidifies. Cut or break the polymer into small pieces (approximately 2 mm by 2 mm in size). These pieces must fit into a 1 mL glass syringe. Remove the plunger from the 1 mL glass syringe (do not remove the cap from the tip) and place it on a balance.

Weigh 0.5 g of the pieces directly into the open end of the syringe. Place the glass syringe upright (capped tip downwards) into a 500 mL glass beaker containing distilled water at 65° C. (hot plate) so that no water enters the barrel. The polymer melts completely within 10 minutes in this apparatus. When the polymer pieces have melted, remove the barrel from the water bath, hold it horizontally and remove the cap. Insert the plunger into the barrel and compress the melted polymer into a sticky mass at the tip end of the barrel. Cap the syringe and allow it to cool to room temperature.

For application, the syringe may be reheated to 60° C. and administered as a liquid which solidifies when cooled to body temperature.

B. Procedure for Producing Nanospray

Nanospray is a suspension of small microspheres in saline. If the microspheres are very small (i.e., under 1 μm in diameter) they form a colloid so that the suspension will not sediment under the force of gravity. As is described in more detail below, a suspension of 0.1 μm to 1 μm microparticles may be created suitable for deposition onto tissue through a finger pumped aerosol. Equipment and materials which may be utilized to produce nanospray include 200 mL water jacketed beaker (Kimax or Pyrex), Haake circulating water bath, overhead stirrer and controller with 2 inch diameter (4 blade, propeller type stainless steel stirrer; Fisher brand), 500 mL glass beaker, hot plate/stirrer (Coming brand), 4×50 mL polypropylene centrifuge tubes (Nalgene), glass scintillation vials with plastic insert caps, table top centrifuge (Beckman), high speed centrifuge—floor model (JS 21 Beckman), Mettler analytical balance (AJ 100, 0.1 mg), Mettler digital top loading balance (AE 163, 0.01 mg), automatic pipetter (Gilson), sterile pipette tips, pump action aerosol (Pfeiffer pharmaceuticals) 20 ml, laminar flow hood, polycaprolactone ("PCL"—mol wt 10,000 to 20,000; Polysciences, Warrington, Pa. USA), "washed" (see previous) ethylene vinyl acetate ("EVA"), poly(DL)lactic acid ("PLA" mol wt 15,000 to 25,000; Polysciences), polyvinyl alcohol ("PVA"—mol wt 124,000 to 186,000; 99% hydrolyzed; Aldrich Chemical Co., Milwaukee, Wis. USA), dichloromethane ("DCM" or "methylene chloride;" HPLC grade Fisher scientific), distilled water, sterile saline (Becton and Dickenson or equivalent)

1. Preparation of 5% (w/v) Polymer Solutions

Depending on the polymer solution being prepared, weigh 1.00 g of PCL or PLA or 0.50 g each of PLA and washed EVA directly into a 20 mL glass scintillation vial. Using a measuring cylinder, add 20 mL of DCM and tightly cap the vial. Leave the vial at room temperature (25° C.) for one hour or until all the polymer has dissolved (occasional hand shaking may be used). Dissolving of the polymer can be determined by a visual check; the solution should be clear. Label the vial with the name of the solution and the date it was produced. Store the solutions at room temperature and use within two weeks.

2. Preparation of 3.5% (w/v) Stock Solution of PVA

The solution can be prepared by following the procedure given below, or by diluting the 5% (w/v) PVA stock solution prepared for production of microspheres. Briefly, 17.5 g of PVA is weighed directly into a 600 mL glass beaker, and 500 mL of distilled water is added. Place a 3 inch Teflon coated stir bar in the beaker. Cover the beaker with a cover glass to reduce evaporation losses. Place the beaker in a 2000 mL glass beaker containing 300 mL of water. This will act as a water bath. Stir the PVA at 300 rpm at 85° C. (Coming hot plate/stirrer) for 2 hours or until fully dissolved. Dissolving of the PVA can be determined by a visual check; the solution should be clear. Use a pipette to transfer the solution to a glass screw top storage container and store at 4° C. for a maximum of two months. This solution should be warmed to room temperature before use or dilution.

3. Procedure for Producing Nanospray

Place the stirring assembly in a fume hood. Place 100 mL of the 3.5% PVA solution in the 200 mL water jacketed beaker. Connect the Haake water bath to this beaker and allow the contents to equilibrate at 27° C. (+/−1° C.) for 10 minutes. Set the start speed of the overhead stirrer at 3000 rpm (+/−200 rpm). Place the blade of the overhead stirrer half way down in the PVA solution and start the stirrer. Drip 10 mL of polymer solution (polymer solution used based on type of nanospray being produced) into the stirring PVA over a period of 2 minutes using a 5 mL automatic pipetter. After 3 minutes, adjust the stir speed to 2500 rpm (+/−200 rpm) and leave the assembly for 2.5 hours. After 2.5 hours, remove the stirring blade from the nanospray preparation and rinse with 10 mL of distilled water. Allow the rinse solution to go into the nanospray preparation.

Pour the microsphere preparation into a 500 mL beaker. Wash the jacketed water bath with 70 mL of distilled water. Allow the 70 mL rinse solution to go into the microsphere preparation. Stir the 180 mL microsphere preparation with a glass rod and pour equal amounts of it into four polypropylene 50 mL centrifuge tubes. Cap the tubes. Centrifuge the capped tubes at 10 000 g (+/−1000 g) for 10 minutes. Using a 5 mL automatic pipetter or vacuum suction, draw 45 mL of the PVA solution off of each microsphere pellet and discard it. Add 5 mL of distilled water to each centrifuge tube and use a vortex to resuspend the microspheres in each tube. Using 20 mL of distilled water, pool the four microsphere suspensions into one centrifuge tube. To wash the microspheres, centrifuge the preparation for 10 minutes at 10 000 g (+/−1000 g). Draw the supernatant off of the microsphere pellet. Add 40 mL of distilled water and use a vortex to resuspend the microspheres. Repeat this process two more times for a total of three washes. Do a fourth wash but use only 10 mL (not 40 mL) of distilled water when resuspending the microspheres. After the fourth wash, transfer the microsphere preparation into a preweighed glass scintillation vial.

Cap the vial and let it to sit for 1 hour at room temperature (25° C.) to allow the 2 μm and 3 μm diameter microspheres to sediment out under gravity. After 1 hour, draw off the top 9 mL of suspension using a 5 mL automatic pipetter. Place the 9 mL into a sterile capped 50 mL centrifuge tube. Centrifuge the suspension at 10 000 g (+/−1000 g) for 10 minutes. Discard the supernatant and resuspend the pellet in 20 mL of sterile saline. Centrifuge the suspension at 10 000 g (+/−1000 g) for 10 minutes. Discard the supernatant and resuspend the pellet in sterile saline. The quantity of saline used is dependent on the final required suspension concentration (usually 10% w/v). Thoroughly rinse the aerosol apparatus in sterile saline and add the nanospray suspension to the aerosol.

C. Manufacture of $O[BEOV]_2$ Loaded Nanospray

To manufacture nanospray containing $O[BEOV]_2$, prepare the polymer drug stock solution, weigh the appropriate amount of $O[BEOV]_2$ directly into a 20 mL glass scintillation vial. The appropriate amount is determined based on the percentage of $O[BEOV]_2$ to be in the nanospray. For example, if nanospray containing 5% $O[BEOV]_2$ was required, then the amount of $O[BEOV]_2$ weighed would be 25 mg since the amount of polymer added is 10 mL of a 5% polymer in DCM solution (see next step).

Add 10 mL of the appropriate 5% polymer solution to the vial containing the $O[BEOV]_2$. Cap the vial and vortex or hand swirl it to dissolve the $O[BEOV]_2$ (visual check to ensure $O[BEOV]_2$ dissolved). Label the vial with the date it was produced. This is to be prepared fresh daily.

Follow the procedures as described above, except that polymer/drug (e.g., $O[BEOV]_2$) stock solution is substituted for the polymer solution.

D. Procedure for Producing Film

The term film refers to a polymer formed into one of many geometric shapes. The film may be a thin, elastic sheet of polymer or a 2 mm thick disc of polymer. This film is designed to be placed on exposed tissue so that any encapsulated drug is released from the polymer over a long period of time at the tissue site. Films may be made by several processes, including for example, by casting, and by spraying.

In the casting technique, polymer is either melted and poured into a shape or dissolved in DCM and poured into a shape. The polymer then either solidifies as it cools or solidifies as the solvent evaporates, respectively. In the spraying technique, the polymer is dissolved in solvent and sprayed onto glass, as the solvent evaporates the polymer solidifies on the glass. Repeated spraying enables a build up of polymer into a film that can be peeled from the glass.

Reagents and equipment which were utilized within these experiments include a small beaker, Coming hot plate stirrer, casting molds (e.g., 50 mL centrifuge tube caps) and mold holding apparatus, 20 mL glass scintillation vial with cap (Plastic insert type), TLC atomizer, nitrogen gas tank, polycaprolactone ("PCL"—mol wt 10,000 to 20,000; Polysciences), $O[BEOV]_2$, ethanol, "washed" (see previous) ethylene vinyl acetate ("EVA"), poly(DL)lactic acid ("PLA"—mol wt 15,000 to 25,000; Polysciences), dichloromethane (HPLC grade Fisher Scientific).

1. Procedure for Producing Films—Melt Casting

Weigh a known amount of PCL directly into a small glass beaker. Place the beaker in a larger beaker containing water (to act as a water bath) and put it on the hot plate at 70° C. for 15 minutes or until the polymer has fully melted. Add a known weight of drug to the melted polymer and stir the mixture thoroughly. To aid dispersion of the drug in the melted PCL, the drug may be suspended/dissolved in a small volume (<10% of the volume of the melted PCL) of 100% ethanol. This ethanol suspension is then mixed into the melted polymer. Pour the melted polymer into a mould and let it to cool. After cooling, store the film in a container.

2. Procedure for Producing Films—Solvent Casting

Weigh a known weight of PCL directly into a 20 mL glass scintillation vial and add sufficient DCM to achieve a 10% w/v solution. Cap the vial and mix the solution. Add sufficient $O[BEOV]_2$ to the solution to achieve the desired final $O[BEOV]_2$ concentration. Use hand shaking or vortexing to dissolve the $O[BEOV]_2$ in the solution. Let the solution sit for one hour (to diminish the presence of air bubbles) and then pour it slowly into a mould. The mould used is based on the shape required. Place the mould in the fume hood overnight. This will allow the DCM to evaporate. Either leave the film in the mould to store it or peel it out and store it in a sealed container.

3. Procedure for Producing Films—Sprayed

Weigh sufficient polymer directly into a 20 mL glass scintillation vial and add sufficient DCM to achieve a 2% w/v solution. Cap the vial and mix the solution to dissolve the polymer (hand shaking). Assemble the molds in a vertical orientation in a suitable mold holding apparatus in the fume hood. Position the mold holding apparatus 6 to 12 inches above the fume hood floor on a suitable support (e.g., inverted 2000 mL glass beaker) to enable horizontal spraying. Using an automatic pipette, transfer a suitable volume (minimum 5 mL) of the 2% polymer solution to a separate 20 mL glass scintillation vial. Add sufficient $O[BEOV]_2$ to the solution and dissolve it by hand shaking the capped vial. To prepare for spraying, remove the cap of this vial and dip the barrel (only) of an TLC atomizer into the polymer solution. Note: the reservoir of the atomizer is not used in this procedure—the 20 mL glass vial acts as a reservoir.

Connect the nitrogen tank to the gas inlet of the atomizer. Gradually increase the pressure until atomization and spraying begins. Note the pressure and use this pressure throughout the procedure. To spray the moulds use 5 second oscillating sprays with a 15 second dry time between sprays. During the dry time, finger crimp the gas line to avoid wastage of the spray. Spraying is continued until a suitable thickness of polymer is deposited on the mould. Leave the sprayed films attached to the moulds and store in sealed containers.

E. Procedure for Producing Nanopaste

Nanopaste is a suspension of microspheres suspended in a hydrophilic gel. Within one aspect of the invention, the gel or paste can be smeared over tissue as a method of locating drug-loaded microspheres close to the target tissue. Being water based, the paste will soon become diluted with bodily fluids causing a decrease in the stickiness of the paste and a tendency of the microspheres to be deposited on nearby tissue. A pool of microsphere encapsulated drug is thereby located close to the target tissue.

Reagents and equipment which were utilized within these experiments include glass beakers, Carbopol 925 (pharmaceutical grade, Goodyear Chemical Co.), distilled water, sodium hydroxide (1M) in water solution, sodium hydroxide solution (5M) in water solution, microspheres in the 0.1 lm to 3 lm size range suspended in water at 20% w/v.

1. Preparation of 5% w/v Carbopol Gel

Add a sufficient amount of carbopol to 1M sodium hydroxide to achieve a 5% w/v solution. To dissolve the carbopol in the 1M sodium hydroxide, allow the mixture to sit for approximately one hour. During this time period, stir the mixture using a glass rod. After one hour, take the pH of the mixture. A low pH indicates that the carbopol is not fully dissolved. The pH you want to achieve is 7.4. Use 5M sodium hydroxide to adjust the pH. This is accomplished by slowly adding drops of 5M sodium hydroxide to the mixture, stirring the mixture and taking the pH of the mixture. It usually takes approximately one hour to adjust the pH to 7.4. Once a pH of 7.4 is achieved, cover the gel and let it sit for 2 to 3 hours. After this time period, check the pH to ensure it is still at 7.4. If it has changed, adjust back to pH 7.4 using 5M sodium hydroxide. Allow the gel to sit for a few hours to ensure the pH is stable at 7.4. Repeat the process until the desired pH is achieved and is stable. Label the container with the name of the gel and the date. The gel is to be used to make nanopaste and can be stored for one week.

2. Procedure for Producing Nanopaste

Add sufficient 0.1 μm to 3 μm microspheres to water to produce a 20% suspension of the microspheres. Put 8 mL of the 5% w/v carbopol gel in a glass beaker. Add 2 mL of the 20% microsphere suspension to the beaker. Using a glass rod or a mixing spatula, stir the mixture to thoroughly disperse the microspheres throughout the gel. This usually takes 30 minutes. Once the microspheres are dispersed in the gel, place the mixture in a storage jar. Store the jar at 4° C. It must be used within a one month period.

Example 61

Manufacture of Micropheres

Equipment which is preferred for the manufacture of microspheres described below include: 200 mL water jacketed beaker (Kimax or Pyrex), Haake circulating water bath, overhead stirrer and controller with 2 inch diameter (4 blade, propeller type stainless steel stirrer—Fisher brand), 500 mL glass beaker, hot plate/stirrer (Coming brand), 4×50 mL polypropylene centrifuge tubes (Nalgene), glass scintillation vials with plastic insert caps, table top centrifuge (GPR Beckman), high speed centrifuge—floor model (JS 21 Beckman), Mettler analytical balance (AJ 100, 0.1 mg), Mettler digital top loading balance (AE 163, 0.01 mg), automatic pipetter (Gilson). Reagents include polycaprolactone ("PCL"—mol wt 10,000 to 20,000; Polysciences, Warrington Pa., USA), "washed" (see later method of "washing") ethylene vinyl acetate ("EVA"), poly(DL)lactic acid ("PLA"—mol wt 15,000 to 25,000; Polysciences), polyvinyl alcohol ("PVA"—mol wt 124,000 to 186,000; 99% hydrolyzed; Aldrich Chemical Co., Milwaukee Wis., USA), dichloromethane ("DCM" or "methylene chloride"; HPLC grade Fisher scientific), and distilled water.

A. Preparation of 5% (w/v) Polymer Solutions

Depending on the polymer solution being prepared, 1.00 g of PCL or PLA, or 0.50 g each of PLA and washed EVA is weighed directly into a 20 mL glass scintillation vial. Twenty milliliters of DCM is then added, and the vial tightly capped. The vial is stored at room temperature (25° C.) for one hour (occasional shaking may be used), or until all the polymer has dissolved (the solution should be clear). The solution may be stored at room temperature for at least two weeks.

B. Preparation of 5% (w/v) Stock Solution of PVA

Twenty-five grams of PVA is weighed directly into a 600 mL glass beaker. Five hundred milliliters of distilled water is added, along with a 3 inch Teflon coated stir bar. The beaker is covered with glass to decrease evaporation losses, and placed into a 2000 mL glass beaker containing 300 mL of water (which acts as a water bath). The PVA is stirred at 300 rpm at 85° C. (Coming hot plate/stirrer) for 2 hours or until fully dissolved. Dissolution of the PVA may be determined by a visual check; the solution should be clear. The solution is then transferred to a glass screw top storage container and stored at 4° C. for a maximum of two months. The solution, however should be warmed to room temperature before use or dilution.

C. Procedure for Producing Microspheres

Based on the size of microspheres being made (see Table I), 100 mL of the PVA solution (concentrations given in Table I) is placed into the 200 mL water jacketed beaker. Haake circulating water bath is connected to this beaker and the contents are allowed to equilibrate at 27° C. (+/−1° C.) for 10 minutes. Based on the size of microspheres being made (see Table I), the start speed of the overhead stirrer is set, and the blade of the overhead stirrer placed half way down in the PVA solution. The stirrer is then started, and 10 mL of polymer solution (polymer solution used based on type of microspheres being produced) is then dripped into the stirring PVA over a period of 2 minutes using a 5 mL automatic pipetter. After 3 minutes the stir speed is adjusted (see Table I), and the solution stirred for an additional 2.5 hours. The stirring blade is then removed from the microsphere preparation, and rinsed with 10 mL of distilled water so that the rinse solution drains into the microsphere preparation. The microsphere preparation is then poured into a 500 mL beaker, and the jacketed water bath washed with 70 mL of distilled water, which is also allowed to drain into the microsphere preparation. The 180 mL microsphere preparation is then stirred with a glass rod, and equal amounts are poured into four polypropylene 50 mL centrifuge tubes. The tubes are then capped, and centrifuged for 10 minutes (force given in Table I). A 5 mL automatic pipetter or vacuum suction is then utilised to draw 45 mL of the PVA solution off of each microsphere pellet.

TABLE I

PVA CONCENTRATIONS, STIR SPEEDS, AND CENTRIFUGAL FORCE REQUIREMENTS FOR EACH DIAMETER RANGE OF MICROSPHERES.

| PRODUCTION STAGE | MICROSPHERE DIAMETER RANGES: 30 μm to 100 μm | 10 μm to 30 μm | 0.1 μm to 3 μm |
|---|---|---|---|
| PVA concentration | 2.5% (w/v) (i.e.,) dilute 5% stock with distilled water | 5% (w/v) (i.e., undiluted stock) | 3.5% (w/v) (i.e., dilute 5% stock with distilled water |
| Starting Stir Speed | 500 rpm +/− 50 rpm | 500 rpm +/− 50 rpm | 3000 rpm +/− 200 rpm |
| Adjusted Stir Speed | 500 rpm +/− 50 rpm | 500 rpm +/− 50 rpm | 2500 rpm +/− 200 rpm |
| Centrifuge Force | 1000 g +/− 100 g (Table top model) | 1000 g +/− 100 g (Table top model) | 10000 g +/− 1000 g (High speed model) |

Five milliliters of distilled water is then added to each centrifuge tube, which is then vortexed to re-suspend the microspheres. The four microsphere suspensions are then pooled into one centrifuge tube along with 20 mL of distilled water, and centrifuged for another 10 minutes (force given in Table I). This process is repeated two additional times for a total of three washes. The microspheres are then centrifuged a final time, and re-suspended in 10 mL of distilled water. After the final wash, the microsphere preparation is transferred into a pre-weighed glass scintillation vial. The vial is capped, and left overnight at room temperature (25° C.) in order to allow the microspheres to sediment out under gravity. Microspheres, which fall in the size range of 0.1 μm to 3 μm, do not sediment out under gravity, so they are left in the 10 mL suspension.

D. Drying of 10 μm to 30 μm or 30 μm to 100 μm Diameter Microspheres

After the microspheres have sat at room temperature overnight, a 5 mL automatic pipetter or vacuum suction is used to draw the supernatant off of the sedimented microspheres. The microspheres are allowed to dry in the uncapped vial in a drawer for a period of one week or until they are fully dry (vial at constant weight). Faster drying may be accomplished by leaving the uncapped vial under a slow stream of nitrogen gas (flow approx. 10 ml/min.) in the fume hood. When fully dry (vial at constant weight), the vial is weighed and capped. The labelled, capped vial is stored at room temperature. Microspheres are normally stored no longer than 3 months.

E. Drying of 0.1 μm to 3 μm Diameter Micro spheres

This size range of microspheres will not sediment out, so they are left in suspension at 4° C. for a maximum of four weeks. To determine the concentration of microspheres in the 10 mL suspension, a 200 μl sample of the suspension is pipetted into a 1.5 mL preweighed microfuge tube. The tube is then centrifuged at 10,000 g (Eppendorf table top microfuge), the supernatant removed, and the tube allowed to dry at 50° C. overnight. The tube is then re-weighed in order to determine the weight of dried microspheres within the tube.

F. Manufacture of O[BEOV]$_2$ Loaded Microspheres

In order to prepare O[BEOV]$_2$ containing microspheres, an appropriate amount of weighed O[BEOV]$_2$ (based upon the percentage of O[BEOV]$_2$ to be encapsulated) is placed directly into a 20 mL glass scintillation vial. Ten milliliters of an appropriate polymer solution is then added to the vial containing the O[BEOV]$_2$, which is then vortexed until the O[BEOV]$_2$ has dissolved.

Microspheres containing O[BEOV]$_2$ may then be produced essentially as described above in steps (C) through (E).

Example 62

Surfactant Coated Microspheres

A. Materials and Methods

Microspheres were manufactured from poly (DL) lactic acid (PLA), poly methylmethacrylate (PMMA), polycaprolactone (PCL) and 50:50 ethylene vinyl acetate (EVA):PLA essentially as described in Example 2. Size ranged from 10 to 100 μm with a mean diameter 45μm.

Human blood was obtained from healthy volunteers. Neutrophils (white blood cells) were separated from the blood using dextran sedimentation and Ficoll Hypaque centrifugation techniques. Neutrophils were suspended at 5 million cells per mL in Hanks Buffered Salt Solution ("HBSS").

Neutrophil activation levels were determined by the generation of reactive oxygen species as determined by chemiluminescence. In particular, chemiluminescence was determined by using an LKB luminometer with 1 uM luminol enhancer. Plasma pre-coating (or opsonization) of microspheres was performed by suspending 10 mg of microspheres in 0.5 mL of plasma and tumbling at 37° C. for 30 min.

Microspheres were then washed in 1 mL of HBSS and the centrifuged microsphere pellet added to the neutrophil suspension at 37° C. Microsphere surfaces were modified using a surfactant called Pluronic F127 (BASF) by suspending 10 mg of microspheres in 0.5 mL of 2% w/w solution of F127 in HBSS for 30 min at 37° C. Microspheres were then washed twice in 1 mL of HBSS before adding to neutrophils or to plasma for further pre-coating.

B. Results:

Untreated microspheres give chemiluminescence values less than 50 mV. These values represent low levels of neutrophil activation. By way of comparison, inflammatory microcrystals might give values close to 1000 mV, soluble chemical activators might give values close to 5000 mV. However, when the microspheres are pre-coated with plasma, all chemiluminescence values are amplified to the 100 to 300 mV range. These levels of neutrophil response or activation can be considered mildly inflammatory. PMMA gave the biggest response and could be regarded as the most inflammatory. PLA and PCL both become three to four times more potent in activating neutrophils after plasma pretreatment (or opsonization) but there is little difference between the two polymers in this regard. This effect of plasma is termed opsonization and results from the adsorption of antibodies or complement molecules onto the surface. These adsorbed species interact with receptors on white blood cells and cause an amplified cell activation.

Plasma precoating of PCL, PMMA, PLA and EVA:PLA as well as the effect of pluronic F 127 pre-coating prior to plasma precoating of microspheres all show the same effect: (1) plasma pre-coating amplifies the response; (2) pluronic F127 pre-coating has no effect on its own; (3) the amplified neutrophil response caused by plasma pre-coating can be strongly inhibited by pre-treating the microsphere surface with 2% pluronic F127.

The nature of the adsorbed protein species from plasma was also studied by electrophoresis. Using this method, it was shown that pre-treating the polymeric surface with Pluronic F127 inhibited the adsorption of antibodies to the polymeric surface.

Precoating PCL, PMMA, PLA or EVA:PLA microspheres (respectively) with either IgG (2 mg/mL) or 2% pluronic F127 then IgG (2 mg/mL) affected the amplified response caused by pre-coating microspheres with IgG; this can be inhibited by treatment with pluronic F 127.

This result shows that by pre-treating the polymeric surface of all four types of microspheres with Pluronic F127, the "inflammatory" response of neutrophils to microspheres may be inhibited.

Example 63

Encapsulation of $O[BEOV]_2$

A specified amount of $O[BEOV]_2$ is dissolved in 1 mL of a 50:50 ELVAX:poly-l-lactic acid mixture in DCM. Microspheres are then prepared in a dissolution machine (Six-spindle dissolution tester, VanderKanp, Van Kell Industries Inc., U.S.A.) in triplicate at 200 rpm, 42° C., for 3 hours. Microspheres so prepared are washed twice in water and sized on the microscope.

Determination of $O[BEOV]_2$ encapsulation is undertaken in a uv/vis assay (uv/vis lambda max. at 237 nm, fluorescence assay at excitation 237, emission at 325 nm. After 18 hours of tumbling in an oven at 37° C., the total of $O[BEOV]_2$ released from the microspheres is determined.

Example 64

Therapeutic Agent-loaded Polymeric Films Composed of Ethylene Vinyl Acetate and a Surfactant Two types of films are investigated within this example: pure EVA films loaded with $O[BEOV]_2$ and EVA/surfactant blend films loaded with $O[BEOV]_2$.

The surfactants being examined are two hydrophobic surfactants (Span 80 and Pluronic L101) and one hydrophilic surfactant (Pluronic F127). The pluronic surfactants are themselves polymers, which is an attractive property since they can be blended with EVA to optimize various drug delivery properties. Span 80 is a smaller molecule which is in some manner dispersed in the polymer matrix, and does not form a blend.

Surfactants are useful in modulating the release rates of $O[BEOV]_2$ from films and optimising certain physical parameters of the films. One aspect of the surfactant blend films, which indicates that drug release rates can be controlled, is the ability to vary the rate and extent to which the compound will swell in water. Diffusion of water into a polymer-drug matrix is critical to the release of drug from the carrier. Pure EVA films do not swell to any significant extent in over 2 months. However, by increasing the level of surfactant added to the EVA it is possible to increase the degree of swelling of the compound, and by increasing hydrophilicity swelling can also be increased.

Physical strength and elasticity of the films is assessed by stress/strain curves for pure EVA and EVA-surfactant blend films. This crude measurement of stress demonstrates that the elasticity of films is increased with the addition of Pluronic F127, and that the tensile strength (stress on breaking) is increased in a concentration dependent manner with the addition of Pluronic F127. Elasticity and strength are important considerations in designing a film which can be manipulated for particular peritubular clinical applications without causing permanent deformation of the compound.

Certain surfactant additives can be used to control drug release rates and to alter the physical characteristics of the vehicle.

Example 65

Incorporating Methoxypolyethylene Glycol 350 (MEPEG) into Poly(E-caprolactone to Develop a Formulation for the Controlled Delivery of Therapeutic Agents from a Paste Reagents and equipment that were utilised within these experiments include methoxypolyethylene glycol 350 ("MePEG"—Union Carbide, Danbury, Conn.). MePEG is liquid at room temperature, and has a freezing point of 10° C. to −5° C.

A. Preparation of a MePEG/PCL $O[BEOV]_2$-Containing Paste

MePEG/PCL paste is prepared by first dissolving a quantity of $O[BEOV]_2$ into MePEG, and then incorporating this into melted PCL. One advantage with this method is that no DCM is required.

B. Analysis of Melting Point

The melting point of PCL/MePEG polymer blends may be determined by differential scanning calorimetry from 30° C. to 70° C. at a heating rate of 2.5° C. per minute. Briefly, MePEG (as determined by thermal analysis) decreases the melting point of the polymer blend in a concentration dependent manner. This lower melting point also translates into an increased time for the polymer blends to solidify from melt. A 30:70 blend of MePEG:PCL takes more than twice as long to solidify from the fluid melt than does PCL alone.

C. Measurement of Brittleness

Incorporation of MePEG into PCL appears to produce a less brittle solid, as compared to PCL alone. As a "rough"

way of quantitating this, a weighted needle is dropped from an equal height into polymer blends containing from 0% to 30% MePEG in PCL, and the distance that the needle penetrates into the solid is then measured.

For purposes of comparison, a sample of paraffin wax is also tested and the needle penetrated into this a distance of 7.25 mm +/−0.3 mm.

D. Strength Analysis of Various MePEG/PCL Blends

A CT-40 mechanical strength tester is used to measure the strength of solid polymer "tablets" of diameter 0.88 cm and an average thickness of 0.560 cm. The polymer tablets are blends of MePEG at concentrations of 0%, 5%, 10% or 20% in PCL.

Both the tensile strength and the time to failure are plotted as a function of %MePEG in the blend. The addition of MePEG into PCL decreased the hardness of the resulting solid.

Example 66

Alteration of Therapeutic Agent Release from Thermopaste Using Low Molecular Weight Poly(D, L-lactic acid)

As discussed above, depending on the desired therapeutic effect, either quick release or slow release polymeric carriers may be desired. For example, polycaprolactone (PCL) and mixtures of PCL with poly(ethylene glycol) (PEG) produce compositions which release agents over a period of several months.

On the other hand, low molecular weight poly(DL-lactic acid) (PDLLA) gives fast degradation, ranging from one day to a few months depending on its initial molecular weight. The release of drug, in this case, is dominated by polymer degradation. Another feature of low mol. wt.PDLLA is its low melting temperature, (i.e., 40° C.–60° C.), which makes it suitable material for making thermopaste. As described in more detail below, several different methods can be utilized in order to control the polymer degradation rate, including, for example, by changing mol. wt. of the PDLLA, and/or by mixing it with high mol. wt. PCL, PDLLA, or poly(lactide-co-glyocide) (PLGA).

A. Experimental Materials

D,L-lactic acid was purchased from Sigma Chemical Co., St. Louis, Mo., mol. wt. 10–20,000, was obtained from Polysciences, Warrington, Pa., mol. wt.PDLLA (intrinsic viscosity 0.60 dl/g) and PLGA (50:50 composition, viscosity 0.58 dl/g) were from Birmingham Polymers.

B. Synthesis of Low Molecular weight PDLLA

Low mol. wt.PDLLA was synthesized from DL-lactic acid through polycondensation. Briefly, DL-lactic acid was heated in a glass beaker at 200° C. with nitrogen purge and magnetic stirring for a desired time. The viscosity increased during the polymerization, due to the increase of mol. wt. Three batches were obtained with different polymerization times, i.e., 40 min (mol. wt. 800), 120 min, 160 min.

C. Formulation of $O[BEOV]_2$ Thermopastes

To make the thermopastes, it is anticipated that $O[BEOV]_2$ will be loaded into the following materials by hand mixing at a temperature about 60° C.

1) low mol. wt.PDLLA with polymerization time of 40 min.
2) low mol. wt.PDLLA with polymerization time of 120 min.
3) low mol. wt.PDLLA with polymerization time of 160 min.
4) a mixture of 50:50 high mol. wt.PDLLA and low mol. wt.PDLLA 40 min.
5) a mixture of 50:50 high mol. wt.PLGA and low molecular weight PDLLA 40 min.
6) mixtures of high mol. wt.PCL and low mol. wt. PDLLA 40 min with PCL:PDLLA of 10:90, 20:80, 40:60, 60:40, and 20:80.

Mixtures of high mol. wt.PDLLA or PLGA with low mol. wt. PDLLA obtained by dissolving the materials in acetone or other solvent followed by drying.

D. Results

Low mol. wt.PDLLA 40 min was a soft material with light yellow color. The color is perhaps due to the oxidation during the polycondensation. Low mol. wt.PDLLA 120 min (yellow) and 160 min (brown) were brittle solids at room temperature. They all melt at 60° C. Mixtures of 50:50 high molecular weight PDLLA or PLGA with low molecular weight PDLLA 40 min also melt about 60° C.

During the release, low molecular weight PDLLA 40 min and 120 min broke up into fragments within one day.

Although not specifically set forth above, a wide variety of other polymeric carriers may be manufactured, including for example, (1) low mol. wt. (500–10,000) poly(D,L-lactic acid), poly(L-lactic acid), poly(glycolic acid), poly(6-hydroxycaproic acid), poly(5-hydroxyvaleric acid), poly(4-hydroxybutyric acid), and their copolymers; (2) blends of above (#1) above; (3) blends of (#1) above with high mol. wt.poly(DL-lactic acid), poly(L-lactic acid), poly(glycolic acid), poly(6-hydroxycaproic acid), poly(5-hydroxyvaleric acid), poly(4-hydroxybutyric acid), and their copolymers; and (4) copolymers of poly(ethylene glycol) and pluronics with poly(D,L-lactic acid), poly(L-lactic acid), poly (glycolic acid), poly(6-hydroxycaproic acid), poly(5-hydroxyvaleric acid), poly(4-hydroxybutyric acid), and their copolymers.

Example 67

Preparation of Polymeric Compositions Containing Water Soluble Additives and $O[BEOV]_2$ A. Preparation of Polymeric Compositions It is anticipated that microparticles of co-precipitates of $O[BEOV]_2$/additive can be prepared and subsequently added to PCL to form pastes. Briefly, $O[BEOV]_2$ is and mixed with the additive (100 mg) previously dissolved or dispersed in 1.0 mL of distilled water. The mixture is triturated until a smooth paste is formed. The paste is spread on a Petri dish and air-dried overnight at 37° C. The dried mass is pulverized using a mortar and pestle and passed through a mesh #140 (106 μm) sieve (Endecotts Test Sieves Ltd., London, England). The microparticles (40%) are then incorporated into molten PCL (60%) at 65° C. The additives that can be used in the study are gelatin (Type B, 100 bloom, Fisher Scientific), methylcellulose, (British Drug Houses), dextran, T500 (Pharmacia, Sweden), albumin (Fisher Scientific), and sodium chloride (Fisher Scientific). Microparticles of $O[BEOV]_2$ and gelatin or albumin are prepared as described above but are passed through a mesh # 60 (270 lm) sieve (Endecotts Test Sieves Ltd., London, England) to evaluate the effect of microparticle size on the release of the complex from the paste.

B. Drug release studies

Approximately 2.5 mg pellet of $O[BEOV]_2$-loaded paste is suspended in 50 mL of 10 mM phosphate buffered saline, pH 7.4 (PBS) in screw-capped tubes. The tubes are tumbled end-over-end at 37° C. and at given time intervals 49.5 mL of supernatant is removed, filtered through a 0.45 μm membrane filter and can be retained for $O[BEOV]_2$ analysis. An equal volume of PBS is replaced in each tube to maintain sink conditions throughout the study. For analysis, the filtrates are extracted with 3×1 mL dichloromethane (DCM), the DCM extracts evaporated to dryness under a stream of nitrogen and redissolved in 1 mL acetonitrile.

C. Swelling Studies

It is anticipated that O[BEOV]$_2$/additive/PCL pastes will be prepared using O[BEOV]$_2$-additive microparticles of mesh size # 140 (and #60 for gelatin only). They are then extruded to form cylinders, pieces were cut, weighed and the diameter and length of each piece measured using a micrometer (Mitutoyo Digimatic). The pieces are suspended in distilled water (10 mL) at 37° C. and at predetermined intervals the water is discarded and the diameter and the length of the cylindrical pieces are measured and the samples weighed. The morphology of the samples (before and after suspending in water) is examined using scanning electron microscopy (SEM) (Hitachi F-2300). The samples are coated with 60% Au and 40% Pd (thickness 10–15 nm) using a Hummer Instrument (Technics, USA).

Osmotic or swellable, hydrophilic agents embedded as discrete particles in the hydrophobic polymer result in drug release by a combination of the erosion of the matrix, diffusion of drug through the polymer matrix, and/or diffusion and/or convective flow through pores created in the matrix by the dissolution of the water soluble additives. Osmotic agents and swellable polymers dispersed in a hydrophobic polymer would imbibe water (acting as wicking agents), dissolve or swell and exert a turgor pressure which could rupture the septa (the polymer layer) between adjacent particles, creating microchannels and thus facilitate the escape of the drug molecules into the surrounding media by diffusion or convective flow. The swelling and cracking of the paste matrix likely resulted in the formation of microchannels throughout the interior of the matrix.

D. In vivo Anti-Tumor Activity

Pastes, prepared as described above (using mesh size 140 fractions of the O[BEOV]$_2$-gelatin microparticles) are filled into 8×1 mL syringes (BD Insulin Syringe, ½ cc) each syringe containing 150 mg of the paste. Ten week old DBA/2 female mice (16) weighing 18–20 g are acclimatized for 4 days after arrival and each mouse is injected in the posteriolateral flank with MDAY-D2 tumor cells, ($10\times10^6$ $ml^{-1}$) in 100 $\mu$L of phosphate buffered saline on day 1. On day 6, the mice are divided into two groups of eight, the tumor site opened under anesthesia and 150 mg of the paste, previously heated to about 60° C. is extruded at the tumor site and the wound closed. One group is implanted with the O[BEOV]$_2$-loaded paste and the other group with control paste containing gelatin and PCL only. On day 16, the mice are sacrificed and the weight of the mice and the excised tumor are measured.

Example 68

O[BEOV]$_2$ Release From Thermopaste Using PDLLA-PEG-PDLLA and Low Molecular Weight Poly(D,L-lactic acid)

A. Preparation of PDLLA-PEG-PDLLA and low molecular weight PDLLA

DL-lactide is purchased from Aldrich. Polyethylene glycol (PEG) with molecular weight 8,000, stannous octoate, and DL-lactic acid are obtained from Sigma. Poly-ϵ-caprolactone (PCL) with molecular weight 20,000 is obtained from Birmingham Polymers (Birmingham, Ala.). Polystyrene standards with narrow molecular weight distributions are purchased from Polysciences (Warrington, Pa.). Acetonitrile and methylene chloride are HPLC grade (Fisher Scientific).

The triblock copolymer of PDLLA-PEG-PDLLA is synthesized by a ring opening polymerization. Monomers of DL-lactide and PEG in different ratios are mixed and 0.5 wt % stannous octoate is added. The polymerization is carried out at 150° C. for 3.5 hours. Low molecular weight PDLLA is synthesized through polycondensation of DL-lactic acid. The reaction is performed in a glass flask under the conditions of gentle nitrogen purge, mechanical stirring, and heating at 180° C. for 1.5 hours. The PDLLA molecular weight was about 800 measured by titrating the carboxylic acid end groups.

B. Manufacture of paste formulations

It is anticipated that O[BEOV]$_2$ at different loading concentrations will be thoroughly mixed into either the PDLLA-PEG-PDLLA copolymers or blends of PDLLA:PCL 90:10, 80:20 and 70:30 melted at about 60° C. (The temperature may be reduced depending on the stability of O[BEOV]$_2$ The O[BEOV]$_2$ loaded pastes will be weighed into 1 mL syringes and stored at 4° C.

C. Characterization of PDLLA-PEG-PDLLA and the Paste Blends

The molecular weights and distributions of the PDLLA-PEG-PDLLA copolymers are determined at ambient temperature by GPC using a Shimadzu LC-10AD HPLC pump and a Shimadzu RID-6A refractive index detector (Kyoto, Japan) coupled to a $10^4$ Å Hewlett Packard Plgel column. (Other suitable equipment may be substituted.) The mobile phase is chloroform with a flow rate of 1 ml/min. The injection volume of the sample is 20 $\mu$l at a polymer concentration of 0.2% (w/v). The molecular weights of the polymers are determined relative to polystyrene standards. The intrinsic viscosity of PDLLA-PEG-PDLLA in $CHCl_3$ at 25° C. is measured with a Cannon-Fenske viscometer.

Thermal analysis of the copolymers is carried out by differential scanning calorimetry (DSC) using a TA Instruments 2000 controller and DuPont 910OS DSC (Newcastle, Del.). The heating rate is 10° C./min and the copolymer and O[BEOV]$_2$/copolymer matrix samples are weighed (3–5 mg) into crimped open aluminum sample pans.

$^1H$ Nuclear magnetic resonance (NMR) is used to determine the chemical composition of the polymer. $^1H$ NMR spectra of O[BEOV]$_2$ loaded PDLLA-PEG-PDLLA is obtained in $CDCl_3$ using a NMR instrument (Bruker, AC-200E) at 200 MHz.

The morphology of the O[BEOV]$_2$/PDLLA-PEG-PDLLA paste is investigated using scanning electron microscopy (SEM) (Hitachi F-2300). The sample is coated with 60% Au and 40% Pd (thickness 10–15 nm) using a Hummer instrument (Technics, USA).

D. In vitro Release of O[BEOV]$_2$

It is anticipated that a small pellet of O[BEOV]$_2$ loaded PDLLA:PCL paste (about 2 mg) or a cylinder (made by extrusion melten paste through a syringe without needle) of O[BEOV]$_2$ loaded PDLLA-PEG-PDLLA paste will be put into capped 14 mL glass tubes containing 10 mL phosphate buffered saline (PBS, pH 7.4) with 0.4 g/L albumin. The tube will then be incubated at 37° C. with gentle rotational mixing. The supernatant will be withdrawn periodically for O[BEOV]$_2$ analysis and replaced with fresh PBS/albumin buffer. The supernatant (10 mL) is extracted with 1 DCM. The water phase is decanted and the DCM phase is dried under a stream of nitrogen at 60° C. The dried residue is reconstituted in a 40:60 water:acetonitrile mixture and centrifuged at 10,000g for about 1 min. The amount of the O[BEOV]$_2$ in the supernatant is then analyzed.

E. In vivo Animal Studies

Ten week old DBA/2j female mice are acclimatized for 3–4 days after arrival. Each mouse is injected subcutaneously in the posterior lateral flank with $10\times10^5$ tumor cells (MDAY-D2 or other suitable cancer tumor cells) in 100 $\mu$l of PBS on day 1. On day 6, the mice are randomly divided into two groups. Group 1 are implanted with paste alone (control), and group 2 are implanted with paste loaded with $O[BEOV]_2$. A subcutaneous pocket near the tumor is surgically formed under anesthesia and approximately 100 mg of molten paste (warmed to 50° C.–60° C.) is placed in the pocket and the wound closed. On day 16, the mice are sacrificed, and the tumors are removed and weighed. Day 16 is selected to allow the tumor growing into a easily measurable size within the ethical limit.

F. Results

The molecular weight and molecular weight distribution of PDLLA-PEG-PDLLA, relative to polystyrene standards, were measured by GPC. The intrinsic viscosity of the copolymer in $CHCl_3$ at 25° C. was determined using a Canon-Fenske viscometer. The molecular weight and intrinsic viscosity decreased with increasing PEG content. The polydispersity of PDLLA-PEG-PDLLA with PEG contents of 10% –40% were from 2.4 to 3.5. However, the copolymer with 70% PEG had a narrow molecular weight distribution with a polydispersity of 1.21. This might be due to a high PEG content reduced the chance of side reactions such as transesterification that results in a wide distribution of polymer molecular weight. Alternatively, a coiled structure of the hydrophobic-hydrophilic block copolymers may result in an artificial low polydispersity value.

DSC scans of pure PEG and PDLLA-PEG-PDLLA copolymers were made. The PEG and PDLLA-PEG-PDLLA with PEG contents of 70% and 40% showed endothermic peaks with decreasing enthalpy and temperature as the PEG content of the copolymer decreased. The endothermic peaks in the copolymers of 40% and 70% PEG were probably due to the melting of the PEG region, indicating the occurrence of phase separation. While pure PEG had a sharp melting peak, the copolymers of both 70% and 40% PEG showed broad peaks with a distinct shoulder in the case of 70% PEG. The broad melting peaks may have resulted from the interference of PDLLA with the crystallization of PEG. The shoulder in the case of 70% PEG might represent the glass transition of the PDLLA region. No thermal changes occurred in the copolymers with PEG contents of 10%, 20% and 30% in a temperature range of 10–250° C., indicating that no significant crystallization had occurred.

Example 69

Manufacture of Polymeric Compositions Containing PCL and MEPEG

A. $O[BEOV]_2$ Release from PCL

Polycaprolactone containing various concentrations of $O[BEOV]_2$ is prepared as described previously. The release of $O[BEOV]_2$ over time is measured.

B. Tensile Strength of MePEG Containing PCL

PCL containing MePEG at various concentrations can be tested for tensile strength and time to fail by a CT-40 Mechanical Strength Tester.

Example 70

Preparation of Pcl Microspheres Scale Up Studies

Microspheres (50 g) were prepared using PCL (nominal molecular weight 80,000) using the solvent evaporation method described below.

A. Method:

A preparation of 500 mL of 10% PCL in DCM and a 4000 mL solution of 1% PVA (mol. Wt 13,000–23,000; 99% hydrolyzed) were emulsified using the Homo Mixer controlled with a rheostat at 40 setting for 10 hours. The mixture was strained using sieve #140 until the microspheres settled at the bottom and then supernatant was decanted. The preparation was then washed 3× with distilled water (using the sedimentation followed by decanting method) and then re-suspended in 250 mL of distilled water and filtered. The microspheres were then air-dried overnight at 37° C.

B. Results:

Microsphere yields were as follows:

| | |
|---|---|
| Initial wt of PCL | =50.1 g |
| Wt. Of microspheres obtained | =41.2g |
| % yield | =(43.2/50.0) × 100 |
| | =86.4 |

Yield (10–50 $\mu$m) about 72%

Mean size 21.4 $\mu$m, median 22.0 $\mu$m mode 24.7 $\mu$m.

Narrower size ranges (20–40 $\mu$m) can be obtained by sieving or by separation using the sedimentation method.

Example 71

Manufacture of PLGA Microspheres

Microspheres were manufactured from (PLLA) lactic acid-glycolic acid (GA) copolymers.

A. Method:

Microspheres were manufactured in the size ranges 0.5–10 $\mu$m, 10–20 $\mu$m and 30–100$\mu$m using standard methods (polymer was dissolved in dichloromethane and emulsified in a polyvinyl alcohol solution with stirring as previously described in PCL or PDLLA microspheres manufacture methods). Various ratio's of PLLA to GA were used as the polymers with different molecular weights [given as Intrinsic Viscosity (I.Vis.)].

B. Result:

Microspheres were manufactured successfully from the following starting polymers:

| PLLA | : | GA | I.Vis. |
|---|---|---|---|
| 50 | : | 50 | 0.74 |
| 50 | : | 50 | 0.78 |
| 50 | : | 50 | 1.06 |
| 65 | : | 35 | 0.55 |
| 75 | : | 25 | 0.55 |
| 85 | : | 15 | 0.56 |

Example 72

Di-block Copolymers

Diblock copolymers of poly(DL-lactide)-block-methoxy polyethylene glycol (PDLLA-MePEG), polycaprolactone-block-methoxy polyethylene glycol (PCL-MePEG) and poly (DL-lactide-co-caprolactone)-block-methoxy polyethylene glycol (PDLLACL-MePEG) were synthesized using a bulk melt polymerization procedure. Briefly, given amounts of monomers DL-lactide, caprolactone, and methoxy polyethylene glycols with different molecular weights were heated (130° C.) to melt under the bubbling of nitrogen and stirring. The catalyst stannous octoate (0.2% w/w) was added to the molten monomers. The polymerization was carried out for 4 hours. The molecular weights, critical micelle concentrations, and the maximum drug loadings are measured with GPC, fluorescence, and solubilization testing, respectively.

Example 73

Encapsulation of $O[BEOV]_2$ in Nylon Microcapsules

A. Preparation of $O[BEOV]_2$-Loaded Microcapsules

It is anticipated that $O[BEOV]_2$ can be encapsulated into nylon microcapsules using the interfacial polymerization techniques. Briefly, a specified amount of $O[BEOV]_2$ and 100 mg of Pluronic F-127 will be dissolved in 1 mL of dichloromethane (DCM) or other suitable solvent and 0.4 mL (about 500 mg) of adipoyl chloride (ADC) is added. This solution is homogenized into 2% PVA solution using the Polytron homogenizer (1 setting) for 15 seconds. A solution of 1,6-hexane-diamine (HMD) in 5 mL of distilled water is added dropwise while homogenizing. The mixture is homogenized for a further 10 seconds after the addition of HMD solution. The mixture is transferred to a beaker and stirred with a magnetic stirrer for 3 hours. The mixture is centrifuged, collected and resuspended in 1 mL distilled water.

Example 74

Polymeric Compositions with Increased Concentrations of $O[BEOV]_2$

PDLLA-MePEG and PDLLA-PEG-PDLLA are block copolymers with hydrophobic (PDLLA) and hydrophilic (PEG or MePEG) regions. At appropriate molecular weights and chemical composition, they may form tiny aggregates of hydrophobic PDLLA core and hydrophilic MePEG shell. It is anticipated that $O[BEOV]_2$ can be loaded into the hydrophobic core, thereby providing $O[BEOV]_2$ with an increased "solubility".

A. Materials and Methods

D,L-lactide was purchased from Aldrich, Stannous octoate, poly (ethylene glycol) (mol. wt. 8,000), MePEG (mol. wt. 2,000 and 5,000) were from Sigma. MePEG (mol. wt. 750) was from Union Carbide. The copolymers were synthesized by a ring opening polymerization procedure using stannous octoate as a catalyst (Deng et al., *J. Polym. Sci. Polym. Lett.* 28:411–416, 1990; Cohn et al., *J. Biomed, Mater. Res.* 22:993–1009, 1988).

For synthesizing PDLLA-MePEG, a mixture of DL-lactide/MePEG/stannous octoate was added to a 10 milliliter glass ampoule. The ampoule was connected to a vacuum and sealed with flame. Polymerization was accomplished by incubating the ampoule in a 1 50° C. oil bath for 3 hours. For synthesizing PDLLA-PEG-PDLLA, a mixture of D,L-lactide/PEG/stannous octoate was transferred into a glass flask, sealed with a rubber stopper, and heated for 3 hours in a 150° C. oven. In all the cases, the amount of stannous octoate was 0.5%–0.7%.

The polymers are dissolved in acetonitrile or other suitable solvent and centrifuged at 10,000 g for 5 minutes to discard any non-dissolvable impurities. It is anticipated that $O[BEOV]_2$ acetonitrile (or other solvent) solution will then be added to each polymer solution to give a solution with $O[BEOV]_2$. The solvent will then be removed to obtain a clear $O[BEOV]_2$/PDLLA-MePEG matrix, under a stream of nitrogen and 60° C. warming. Distilled water, 0.9% NaCl saline, or 5% dextrose is added at four times weight of the matrix. The matrix is finally "dissolved" with the help of vortex mixing and periodic warming at 60° C.

Example 75

Analysis of Drug Release

A known weight of a polymer (typically a 2.5 mg pellet) is added to a 15 mL test tube containing 14 mL of a buffer containing 10 mm $Na_2HPO_4$—$NaH_2PO_4$, 0.145 m NaCl and 0.4 g/l bovine serum albumin. The tubes are capped and tumbled at 37° C. At specific times all the 14 mL of the liquid buffer are removed and replaced with fresh liquid buffer.

The liquid buffer is added to 1 milliliter of methylene chloride or other suitable solvent and shaken for 1 minute to extract all the $O[BEOV]_2$ into the methylene chloride (or other suitable solvent). The aqueous phase is then removed and the solvent phase is dried under nitrogen. The residue is then dissolved in 60% acetonitrile: 40% water and the solution is analysed using the appropriate assay.

For $O[BEOV]_2$ it is anticipated that the liquid buffer will be analyzed directly using a UVNVIS spectrometer.

Example 76

Bioadhesive Microspheres

A. Preparation of Bioadhesive Microspheres

Microspheres were made from 100k g/mol PLLA with a particle diameter range of 10–60 $\mu$m. The microspheres were incubated in a sodium hydroxide solution to produce carboxylic acid groups on the surface by hydrolysis of the polyester.

The reaction was characterized with respect to sodium hydroxide concentration and incubation time by measuring surface charge. The reaction reached completion after 45 minutes of incubation in 0.1M sodium hydroxide. Following base treatment, the microspheres were coated with dimethylaminoproylcarbodiimide (DEC), a cross-linking agent by suspending the microspheres in an alcoholic solution of DEC and allowing the mixture to dry into a dispersible powder. The weight ratio of microspheres to DEC was 9:1. After the microspheres ere dried, they were dispersed with stirring into a 2% w/v solution of poly (acrylic acid) and the DEC allowed to react with PAA to produce a water insoluble network of cross-linked PAA on the microspheres surface. Scanning electron microscopy was used to confirm the presence of PAA on the surface of the microspheres.

Example 77

The Effect of $O[BEOV]_2$ in the Treatment of Bacterial Infections $O[BEOV]_2$ is incubated at various concentrations in vitro with isolated strains of bacteria such as *Streptococcus pneumoniae.* The minimum inhibitory concentration is determined from these studies of $O[BEOV]_2$ to determine the sensitivity of the bacterial strains to the compounds. Examination for inhibition of incorporation of thymidine, uridine, leucine various ions and glucose into the cells of the bacteria is determined to understand the effect of $O[BEOV]_2$ on the transport of substrates and ions through the membrane and thus the mechanism of inhibition of $O[BEOV]_2$.

Example 78

The Effect of $O[BEOV]_2$ in the Treatment of Joint Prostheses Failure

The process of cellular recruitment in aseptic loosening of prosthetic joint implants involves the association of macrophages with particulate debris from the cement mantle consisting of polymethylmethacrylate (PMMA) at the joint-tissue interface. This involvement eventually leads to further cellular recruitment, bone resorption and loosening of the joint. As part of this process, cytokines released by osteoblasts stimulate the recruitment of macrophages and osteoclasts into sites of inflammation at the bone-cement interface. Thus experiments designed to test the efficacy of O[BEOV]$_2$ in the treatment of joint prostheses failure involve exposure of macrophages to PMMA particles with and without OH[BEOV]$_2$ followed by measure of tumor necrosis factor (TNF), prostaglandin E2 and interleukin 1 (Perry et al., *British Journal of Rheumatology,* 34: 1127–1134, 1995), (Horowitz et al., *Calcif Tissue Int.,* 57: 301–305, 1995). Furthermore, the effects of O[BEOV]$_2$ on cytokine release of osteoblasts in vitro are then tested. Osteoblasts are incubated with conditioned medium from macrophages exposed to PMMA with and without O[BEOV]$_2$ followed by measure of granulocyte macrophage colony stimulating factor (GM-CSF), interleukin 6 (IL-6) and prostaglandin E2 (PGE-2). These studies will demonstrate the effectiveness of O[BEOV]$_2$ in the presence of PMMA on factors which are responsible for aseptic loosening of prosthetic joint implants. Bone resorption will then be measured in an animal model according to the methods of Aspenberg et al., *J. Bone Joint Surg,* 78-B: 641–646, 1996, with and without the incorporation of OH[BEOV]$_2$ in the PMMA cement.

Example 79

Effect of O[BEOV]$_2$ for Treatment or Prevention of Periodontal Disease

Periodontitis, defined as an inflammation of the supporting tissue of the teeth is a progressively destructive disease leading to loss of bone and periodontal ligament. It is characterized by resorption of the alveolar bone and loss of soft tissue attachment to the tooth and is a major cause of tooth loss in the adult. To determine the effect of O[BEOV]$_2$ administration on periodontal disease, subjects are treated with O[BEOV]$_2$ at weekly intervals and the degree of bone density assessed over time and prevalence of subgingival bacteria including *Porphyromonas gingivalis, Prevotella intermedia, Bacteroides forsythus,* and *Actinobacillus actinomycetemcomitans* evaluated. Methods to assess the degree of osteopenia include various measures of bone density through one or more of the following single photon absorptiometry, dual photon absorptiometry, duel energy X-ray absorptiometry, quantitative computerized tomography or, but not limited to, digital subtraction radiography. Methods to assess the degree of periodontitis include oral measurements such as alveolar crest height, clinical attachment loss, and residual ridge resorption as well as clinical outcomes including tooth loss, bleeding and edentulousness. Assessment of these key areas over time will determine the efficaciousness of O[BEOV]$_2$ in the treatment of this disease.

Example 80

O[BEOV]$_2$ in the Treatment of Inflammatory Bowel Disease (IBD)

Inflammatory bowel disease (IBD), namely Crohn's disease and ulcerative colitis, is characterized by periods of relapse and remission. The best available model of IBD is produced in the rat by the intracolonic injection of 2,4,6-trinitrobenzene sulphonic acid (TNB) in a solution of ethanol and saline (Morris et al., *Gastroenterology,* 96: 795–803, 1989). A single administration initiates an acute and chronic inflammation that persists for several weeks. However, pharmacologically, the rabbit colon has been shown to resemble the human colon more so than does the rat (*Gastroenterology,* 99: 13424–1332, 1990).

Female New Zealand white rabbits are used in all experiments. The animals are anesthetized intravenously (i.v.) with phenobarbitol. An infants' feeding tube is inserted rectally, so that the tip is 20 cm proximal to the anus, for injection of the TNB (0.6 ml; 40 mg in 25% ethanol in saline). One week following TNB administration, the rabbits are randomized into 3 treatment groups. At this time, the animals receive either no treatment, vehicle alone (i.v.) or O[BEOV]$_2$ (i.v.). This is repeated every 4 days for a total of 4 treatments.

During the course of the study, rabbits are examined weekly by endoscopy using a pediatric bronchoscope under general anesthesia, induced as above.

Damage is scored by an endoscopist (blinded) according to the following scale: 0, no abnormality; 1, inflammation, but no ulceration; 2, inflammation and ulceration at 1 site (<1 cm); 3, two or more sites of inflammation and ulceration or one major site of inflammation and ulceration (>1 cm) along the length of the colon.

Following the last treatment, the rabbits are sacrificed with Euthanol at 24 hours and 1, 2, 4 and 6 weeks. The entire colon is isolated, resected and opened along the anti-mesenteric border, washed with saline and placed in Hank's balanced salt solution containing antibiotics. The colon is examined with a stereomicroscope and scored according to the same criteria as at endoscopy. As well, specimens of colon are selected at autopsy, both from obviously inflammed and ulcerated regions and from normal colon throughout the entire length from anus to ascending colon. The tissues are fixed in 10% formaldehyde and processed for embedding in paraffin; 5 mm sections are cut and stained with hemotoxylin and eosin. The slides are examined for the presence or absence of IBD histopathology.

The initial experiment can be modified for the use of oral O[BEOV]$_2$ following induction of colitis in rabbits by the intracolonic injection of TNB. The animals are randomized into 3 groups receiving no treatment, vehicle alone or orally formulated OH[BEOV]$_2$.

Example 81

Effects of O[BEOV]$_2$ in an Animal Model of Surgical Adhesions

The use of O[BEOV]$_2$-loaded films to reduce adhesion formation is examined in the rabbit uterine horn model.

New Zealand female white rabbits are anesthetized and a laparotomy is performed through a midline incision. The uterine horns are exposed and a 5 cm long segment off each is abraded using a scalpel blade. This abrasion is sufficient to remove the serosa, resulting in punctate bleeding. Rabbits are randomly assigned to the control or paclitaxel treated groups and to post-operative evaluation periods of two, four and eight weeks. In the paclitaxel treated group, each uterine horn is completely wrapped with O[BEOV]$_2$-loaded film following abrasion. The musculoperitoneal layer is closed with sutures and the cutaneous layer with skin staples.

Animals are evaluated for adhesion formation two, four or eight weeks after surgery. The animals are euthanized humanely and necropsies performed. The uterine horns are examined grossly and histologically using standard microscopic techniques. Grossly, the adhesions are graded using a standard scoring system which is based on the fact that 5 cm of the uterine horn is traumatized; thus, the extent of adhesion formation is determined by measuring the length of the area containing adhesions. The following grading system is used: 0=no adhesions, 1=adhesion on 25% of the area, 2 =adhesions on 50% of the area and 3 =total adhesion involvement. The severity of the adhesions is measured as follows: 0=no resistance to separation, 0.5=some resistance (moderate force needed), and 1=sharp dissection required. The total grade is additive, with an adhesion score range of 0–4 which represents both extent and severity.

All publications and patent applications mentioned in this specification are herein incorporated by reference to the same extent as if each individual publication or patent application was specifically and individually incorporated by reference.

From the foregoing it will be appreciated that, although specific embodiments of the invention have been described herein for purposes of illustration, various modifications may be made without deviating from the spirit and scope of the invention.

What is claimed is:

1. A vanadium(V) complex and pharmaceutically acceptable salts thereof, of the formula:

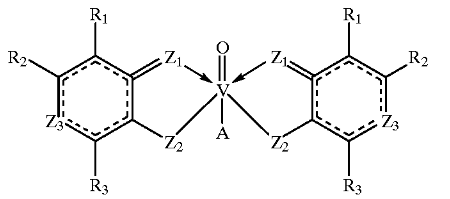

wherein, $Z_1$ is independently selected from O and $NR_4$;

$Z_2$ is independently selected from O and $NR_5$;

$Z_3$ is independently selected from O, NR, and $C(R_7)_2$;

$R_1$, $R_2$, $R_3$, $R_4$, $R_5$, $R_6$ and $R_7$ are each independently selected from $C_1$–$C_{10}$alkyl, substituted $C_1$–$C_{10}$alkyl, $C_7$–$C_{15}$aralkyl, substituted $C_7$–$C_{15}$aralkyl, $C_7$–$C_{15}$alkylaryl, substituted $C_7$–$C_{15}$alkylaryl, $C_6$–$C_{10}$aryl, substituted $C_6$–$C_{10}$aryl and H, provided that $R_3$ is not methyl; and independently $R_1$ and $R_2$, or $R_1$ and $R_4$, may together form a $C_7$–$C_{15}$alkylaryl, substituted $C_7$–$C_{15}$alkylaryl, $C_6$–$C_{10}$aryl, and substituted $C_6$–$C_{10}$aryl, wherein a substituted alkyl, aralkyl, alkylaryl or aryl contains at least one substituent selected from hydroxyl and halide;

A is selected from —OH, =O and

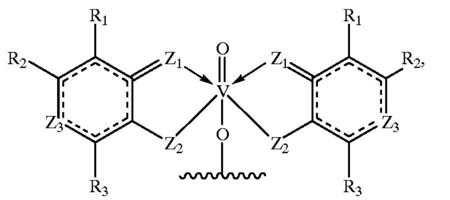

wherein $Z_1$, $Z_2$, $Z_3$, $R_1$, $R_2$, $R_3$, $R_4$, $R_5$, $R_6$ and $R_7$ are each defined as above; and a ring which includes $Z_3$ also contains two normalized bonds.

2. The complex of claim 1 wherein A is =O.

3. The complex of claim 1 wherein A is —OH.

4. The complex of claim 1 wherein A is

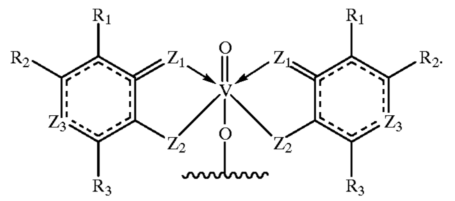

5. The complex of claim 1 wherein $Z_1$ and $Z_2$ are oxygen.

6. The complex of claim 1 wherein vanadium is complexed to an α-hydroxypyrone of the formula

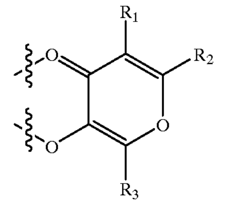

wherein $Z_1$, $Z_2$ and $Z_3$ are oxygen.

7. The complex of claim 6 wherein A is =O.

8. The complex of claim 6 wherein A is —OH.

9. The complex of claim 6 wherein A is

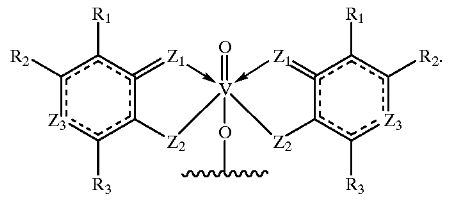

10. The complex of claim 6 wherein $R_1$ and $R_2$ are each hydrogen.

11. The complex of claim 6 wherein $R_3$ is selected from $C_1$–$C_{10}$alkyl and substituted $C_1$–$C_{10}$alkyl.

12. The complex of claim 6 wherein $R_1$ and $R_2$ are each hydrogen and $R_3$ is $C_1$–$C_5$alkyl.

13. The complex of claim 12 wherein $R_3$ is $C_2$alkyl.

14. The complex of claim 13 wherein A is =O.

15. The complex of claim 13 wherein A is —OH.

16. The complex of claim 13 wherein A is

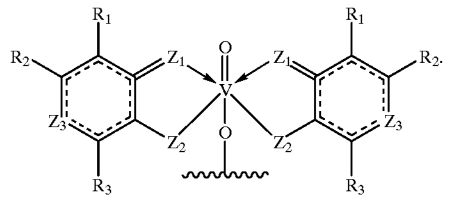

17. A composition comprising a complex of claim 1 and a pharmaceutically acceptable carrier, excipient or diluent.

18. The composition of claim 17 is the form of a paste.

19. A composition of claim 17 comprising microspheres.

20. A composition of claim 17 comprising ethyl vinyl acetate copolymer.

21. A composition of claim 17 comprising polyester.

22. A composition of claim 17 comprising poly (alkyleneoxide).

23. The composition of claim 17 wherein A in the vanadium(V) complex is —OH.

24. The composition of claim 17 wherein A in the vanadium (V) complex is =O.

25. The composition of claim 17 wherein A in the vanadium(V) complex is

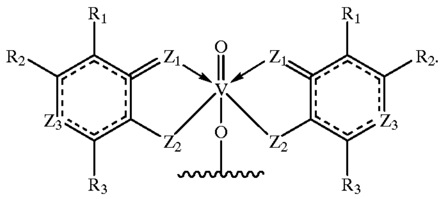

26. A method of providing therapeutic treatment to an animal subject in need thereof, comprising administering to the subject a therapeutically effective amount of a complex according to claim 1, where the subject has a condition selected from the group consisting of a proliferative disorder, a bone destruction disorder, metastases, a persistent tumor, an arthritis, psoriasis, multiple sclerosis, atherosclerosis, diabetes, occular abnormalities secondary to diabetes, nephropathy, vasculopathy, hypertension, obesity, chronic inflammation, chronic inflammatory autoimmune disease, cardiovascular abnormalities, respiratory abnormalities, lymphatic abnormalities, inflammation, periodontitis, bacterial infection, surgical adhesion, prostheses failure and cancer.

27. The method of claim 26 for the treatment of a proliferative disorder.

28. The method of claim 26 for the treatment of a bone destruction disorder.

29. The method of claim 26 for the treatment of metastases.

30. The method of claim 26 where the persistent tumor is a drug resistant tumor.

31. The method of claim 26 for the treatment of arthritis.

32. The method of claim 26 for the treatment of psoriasis.

33. The method of claim 26 for the treatment of multiple sclerosis.

34. The method of claim 26 where the cardiovascular abnormalities, the respiratory abnormalities and the lymphatic abnormalities are vessel obstructive abnormalities.

35. The method of claim 26 for the treatment of diabetes.

36. The method of claim 26 where the ocular abnormality secondary to diabetes is retinopathy, cataracts or neuropathy.

37. The method of claim 26 for the treatment of a diabetes-related metabolic complication selected from retinopathy, nephropathy and vasculopathy.

38. The method of claim 26 for the treatment of hypertension.

39. The method of claim 26 for the treatment of obesity.

40. The method of claim 26 for the treatment of chronic inflammatory autoimmune disease.

41. The method of claim 26 for the treatment of cardiovascular disease.

42. The method of claim 26 for the treatment of lupus.

43. The method of claim 26 where the bacterial infection is from an anaerobic or aerobic bacterium.

44. The method of claim 26 for the treatment of joint prostheses failure.

45. The method of claim 26 for the treatment of periodontal disease.

46. The method of claim 26 for the treatment or prevention of surgical adhesions.

47. The method of claim 26 for the treatment of Inflammatory Bowel Disease (IBD).

* * * * *

UNITED STATES PATENT AND TRADEMARK OFFICE

CERTIFICATE OF CORRECTION

PATENT NO. : 6,232,340 B1 
DATED : May 15, 2001
INVENTOR(S) : Zaihui Zhang et al.

It is certified that error appears in the above-identified patent and that said Letters Patent is hereby corrected as shown below:

Column 55, claim 1,
Line 39, "O,NR, and" should read -- O, $NR_6$ and --.

Signed and Sealed this

Nineteenth Day of February, 2002

Attest:

JAMES E. ROGAN

*Attesting Officer* *Director of the United States Patent and Trademark Office*